US008865428B2

(12) United States Patent
Sakai et al.

(10) Patent No.: US 8,865,428 B2
(45) Date of Patent: Oct. 21, 2014

(54) PROTEIN PRODUCTION METHOD, FUSION PROTEIN, AND ANTISERUM

(75) Inventors: Hiroshi Sakai, Okayama (JP); Toru Hayakawa, Okayama (JP)

(73) Assignees: National University Corporation Okayama University, Okayama (JP); Japan Lamb Co., Ltd., Hiroshima (JP)

( * ) Notice: Subject to any disclaimer, the term of this patent is extended or adjusted under 35 U.S.C. 154(b) by 402 days.

(21) Appl. No.: 13/056,944

(22) PCT Filed: Jul. 30, 2009

(86) PCT No.: PCT/JP2009/063603
§ 371 (c)(1),
(2), (4) Date: May 9, 2011

(87) PCT Pub. No.: WO2010/013789
PCT Pub. Date: Feb. 4, 2010

(65) Prior Publication Data
US 2011/0223686 A1    Sep. 15, 2011

(30) Foreign Application Priority Data
Aug. 1, 2008 (JP) ................................. 2008-199166

(51) Int. Cl.
*C12P 21/06* (2006.01)
*C12P 21/02* (2006.01)
*C07K 14/47* (2006.01)
*C12N 15/62* (2006.01)

(52) U.S. Cl.
CPC ............ *C12N 15/62* (2013.01); *C07K 2319/35* (2013.01); *C12P 21/02* (2013.01); *C07K 14/4737* (2013.01)
USPC ... 435/69.1; 435/69.7; 424/192.1; 424/236.1; 424/246.1

(58) Field of Classification Search
None
See application file for complete search history.

(56) References Cited

FOREIGN PATENT DOCUMENTS

JP    58 211659    12/1983
JP    61 243363    10/1986

OTHER PUBLICATIONS

Carmona, A. A. et al., "Expression and crystallization of a Cry3Aa-Cry1Ac chimerical protein of *Bacillus thuringiensis*,"World Journal of Microbiology & Biotechnology, 1999, vol. 15, pp. 455-463.
Chang, J. H. et al., "An improved baculovirus insecticide producing occlusion bodies that contain *Bacillus thuringiensis* insect toxin," Journal of Invertebrate Pathology, 2003, vol. 84, pp. 30-37.

English Translation of Hayakawa et al., Heisei 21 Nendo Sanshi-Konchu Kino Riyo Gakujutsu Koenkai—Nippon Sanshi Gakkai 79 Kai Taikai Koen Yoshishu, Jun. 16, 2009, vol. 79, pp. 21.
English Translation of Ishida et al., Nippon Nogei Kagakukai Taikai Koen Yoshishu, Mar. 5, 2009, 2P0945B, pp. 118.
English Translation of Sakai et al., Nippon Nogei Kagakukai Taikai Koen Yoshishu, Mar. 5, 2009, 2P0946B, pp. 118.
English Translation of Sakai et al., Seikagaku, Nov. 25, 2008, vol. 80, No. 11, 2P-1450.
English Translation of Sato et al., Seikagaku, Nov. 25, 2008, vol. 80, No. 11, 2P-1451.
Grochulski, P. et al., "*Bacillus thuringiensis* CrylA(a) Insecticidal Toxin: Crystal Structure and Channel Formation," J. Mol. Biol. 1995, vol. 254, pp. 447-464.
Hayakawa et al., Heisei 21 Nendo Sanshi-Konchu Kino Riyo Gakujutsu Koenkai—Nippon Sanshi Gakkai 79 Kai Taikai Koen Yoshishu, Jun. 16, 2009, vol. 79, pp. 21.
Hayakawa et al., Seikagaku, Nov. 25, 2008, vol. 80, No. 11, 2P-1449.
International Search Report for PCT/JP2009/063603 dated Sep. 1, 2009.
Ishida et al., Nippon Nogei Kagakukai Taikai Koen Yoshishu, Mar. 5, 2009, 2P0945B, pp. 118.
Milne, R. et al., "Purification and characterization of a trypsin-like digestive enzyme from spruce budworm (*Choristoneura fumiferana*) responsible for the activation of delta-endotoxin from *Bacillus thuringiensis*," Insect. Biochem. Molec. Biol., 1993, vol. 23, No. 6, pp. 663-673.
Nitsusui Seiyaku KK, "Handy and quick assay of serum crp by immunological nephelometry," Patent Abstracts of Japan, Publication Date: Dec. 9, 1983; English Abstract of JP-58 211659.
Nitsusui Seiyaku KK, "Highly sensitive assay of CRP," Patent Abstracts of Japan, Publication Date: Oct. 29, 1986; English Abstract of JP-61 243363.
Park, H. et al., "Domain I plays an Important Role in the Crystallization of Cry3A in *Bacillus thuringiensis*," Molecular Biotechnology, 2000.
Roh, J. Y. et al., "Expression and characterization of a recombinant Cry11Ac crystal protein with enhanced green fluorescent protein in acrystalliferous *Bacillus thuringiensis*," Letters in Applied Microbiology, 2004, vol. 38, pp. 393-399.
Sakai et al., Nippon Nogei Kagakukai Taikai Koen Yoshishu, Mar. 5, 2009, 2P0946B, pp. 118.
Sakai et al., Seikagaku, Nov. 25, 2008, vol. 80, No. 11, 2P-1450.
Sato et al., Seikagaku, Nov. 25, 2008, vol. 80, No. 11, 2P-1451.

(Continued)

*Primary Examiner* — Jennifer Graser
(74) *Attorney, Agent, or Firm* — Millen, White, Zelano & Branigan, P.C.

(57) ABSTRACT

Disclosed are a highly efficient method for production of heterologous proteins performed by utilizing microorganisms, as well as fusion proteins, and an antiserum. The method includes a method for production of a protein (A) in the form of a fusion protein, comprising the steps of (a) preparing a DNA which codes for a fusion protein comprising the peptide chain forming the protein (A) and the C-terminal peptide or its fragment (B) of the Cry proteins produced by *Bacillus thuringiensis*, and (b) introducing the DNA into a host bacterium to transform the same, and (c) allowing the fusion protein to be expressed in the transformed host bacterium, as well as a method for production of the protein (A) itself comprising a further step of removing the peptide chain (B) from the fusion protein obtained.

9 Claims, 19 Drawing Sheets

(56) References Cited

OTHER PUBLICATIONS

Schnepf, E. et al., "*Bacillus thuringiensis* and its pesticidal crystal proteins," Microbiology and Molecular Biology Reviews, Sep. 1998, pp. 775-806.

Vazquez-Padron, R. I. et al., "Cryptic endotoxic nature of *Bacillus thuringiensis* CryIАb insecticidal crystal protein," FEBS Letters, 2004, vol. 570, pp. 30-36.

Wabiko, H. et al., "Only part of the protoxin gene of *Bacillus thuringiensis* subsp. berliner 1715 is necessary for Insecticidal Activity," Applied and Environmental Microbiology, Mar. 1985, pp. 706-708.

Yamagiwa, M. et al., "Activation process of dipteran-specific Insecticidal Protein Produced by *Bacillus thuringiensis* subsp. *israelensis*," Applied and Environmental Microbiology, Aug. 1999, pp. 3464-3469.

C1-1-f    EcoRV
caagaattgatATCATCAACACCCTTCTACGCAAACCCTGATCAAGAACACCCTGCAATCGGAACTGACC
    EcoRI                                                         1-2
C1-1&2-r
GGTACAACTCTTCGCTAATACATTCCACCAGATTTGCCGCTTGGTCGATGTCGTAGTCGGTCAGTTCCGATTCGCAGG
    (2-3)                                                                (1-2)
C1-2&3-f
GGAATGTATTAGCGAAGAGTTGTACCCGAAAGAAAGATGCTGTTGTTGGACGAAGTGAAGAACGCAAAGC
                  2-3                                               3-4
C1-3&4-r
CGTAGCCGATTCGAAGTCGCCCGTTTTGCAGCACGTTACGCGCGATTGGCTCAGTTGCTTTGCGTTCTTCACTTCG
    (4-5)                                                          (3-4)
C1-4&5-f
CGACTTCGAATCGGCTACGCTGGGTTGGACCACGAGCGACAATATCACCATTCAAGAAGACGATCCG
                4-5                                             5-6
C1-5&6-r
CGGGAAGATGGTACCATCGATGTCACGCGCCGGACATGTGCAGGTAATGGCCTTTGAAAATCGGATCGTCTTCTTGAATGG
    (6-7)                                                                  (5-6)
C1-6&7-f
CGATGGTACCATCTTCCCGACCTACATCTTCCAAAAGATCGATGAATCGAAATTGAAGCCGTACACC
    6-7                                                    7-8
C1-7&8-r
CGACGTCCTTGCTGCTACCCACGAAACCACGCCACCAGGTAACGGGTGTACGGCTTCAATTTCG
    (8-9)                                                (7-8)
C1-8&9-f
GGTAGCCAGCAAGGACGTCGAACTGGTGGTCTCGCGCTACGGCGAAGAAATCGATGCAATCATGAATGTGC
                8-9                                                9
C1-9-r                 NaeI
gtcgaaggtcacgggtacaggtagttcaagtctgcCGGCACATTCATGATTGCATCG
    SalI                                 (9)

Figure 1

X-Syn4A-C1-f

GG<u>CTCGAG</u><u>ATCATCAACACCTTCTAC</u>

X-S-Syn4A-C1-r

GG<u>CTCGAG</u>CCCGGGCC<u>GGCACATTCATGATT</u>

4AaCter-MM29kD    MM29kD-4AaCter

4AaCter-MM29kD    MM29kD-4AaCter

1: 4AaCter-CRP    2: native CRP

Primary antibody    : anti-4AaCter-CRP goat antiserum
Secondary antibody: anti-goat IgG antibody

SEQUENCE LISTING

```
<160> NUMBER OF SEQ ID NOS: 112

<210> SEQ ID NO 1
<211> LENGTH: 156
<212> TYPE: PRT
<213> ORGANISM: Bacillus thuringiensis

<400> SEQUENCE: 1

Ala Val Asn Glu Leu Phe Thr Ser Ser Asn Gln Ile Gly Leu Lys Thr
1               5                   10                  15

Asp Val Thr Asp Tyr His Ile Asp Gln Val Ser Asn Leu Val Glu Cys
            20                  25                  30

Leu Ser Asp Glu Phe Cys Leu Asp Glu Lys Gln Glu Leu Ser Glu Lys
        35                  40                  45

Val Lys His Ala Lys Arg Leu Ser Asp Glu Arg Asn Leu Leu Gln Asp
    50                  55                  60

Pro Asn Phe Arg Gly Ile Asn Arg Gln Leu Asp Arg Gly Trp Arg Gly
65                  70                  75                  80

Ser Thr Asp Ile Thr Ile Gln Gly Gly Asp Asp Val Phe Lys Glu Asn
                85                  90                  95

Tyr Val Thr Leu Leu Gly Thr Phe Asp Glu Cys Tyr Pro Thr Tyr Leu
            100                 105                 110

Tyr Gln Lys Ile Asp Glu Ser Lys Leu Lys Ala Tyr Thr Arg Tyr Gln
        115                 120                 125

Leu Arg Gly Tyr Ile Glu Asp Ser Gln Asp Leu Glu Ile Tyr Leu Ile
    130                 135                 140

Arg Tyr Asn Ala Lys His Glu Thr Val Asn Val Pro
145                 150                 155

<210> SEQ ID NO 2
<211> LENGTH: 156
<212> TYPE: PRT
<213> ORGANISM: Bacillus thuringiensis
```

<400> SEQUENCE: 2

Ala Val Asn Glu Leu Phe Thr Ser Ser Asn Gln Ile Gly Leu Lys Thr
1               5                   10                  15

Asp Val Thr Asp Tyr His Ile Asp Gln Val Ser Asn Leu Val Glu Cys
            20                  25                  30

Leu Ser Asp Glu Phe Cys Leu Asp Glu Lys Lys Glu Leu Ser Glu Lys
        35                  40                  45

Val Lys His Ala Lys Arg Leu Ser Asp Glu Arg Asn Leu Leu Gln Asp
    50                  55                  60

Pro Asn Phe Arg Gly Ile Asn Arg Gln Leu Asp Arg Gly Trp Arg Gly
65                  70                  75                  80

Ser Thr Asp Ile Thr Ile Gln Gly Gly Asp Val Phe Lys Glu Asn
                85                  90                  95

Tyr Val Thr Leu Leu Gly Thr Phe Asp Glu Cys Tyr Pro Thr Tyr Leu
                100                 105                 110

Tyr Gln Lys Ile Asp Glu Ser Lys Leu Lys Ala Tyr Thr Arg Tyr Gln
            115                 120                 125

Leu Arg Gly Tyr Ile Glu Asp Ser Gln Asp Leu Glu Ile Tyr Leu Ile
        130                 135                 140

Arg Tyr Asn Ala Lys His Glu Thr Val Asn Val Pro
145                 150                 155

<210> SEQ ID NO 3
<211> LENGTH: 156
<212> TYPE: PRT
<213> ORGANISM: Bacillus thuringiensis

<400> SEQUENCE: 3

Ala Val Asn Glu Leu Phe Thr Ser Ser Asn Gln Ile Gly Leu Lys Thr
1               5                   10                  15

Asp Val Thr Asp Tyr His Ile Asp Gln Val Ser Asn Leu Val Glu Cys
            20                  25                  30

Leu Ser Asp Glu Phe Cys Leu Asp Glu Lys Lys Glu Leu Ser Glu Lys
        35                  40                  45

Val Lys His Ala Lys Arg Leu Ser Asp Glu Arg Asn Leu Leu Gln Asp
    50                  55                  60

Pro Asn Phe Arg Gly Ile Asn Arg Gln Leu Asp Arg Gly Trp Arg Gly
65                  70                  75                  80

Asn Thr Asp Ile Thr Ile Gln Gly Gly His Asp Val Phe Lys Glu Asn
                85                  90                  95

Tyr Val Thr Leu Leu Gly Thr Phe Asp Glu Cys Tyr Pro Thr Tyr Leu
                100                 105                 110

Tyr Gln Lys Ile Asp Glu Ser Lys Leu Lys Ala Tyr Thr Arg Tyr Gln
            115                 120                 125

Leu Arg Gly Tyr Ile Glu Asp Ser Gln Asp Leu Glu Ile Tyr Leu Ile
        130                 135                 140

Arg Tyr Asn Ala Lys His Glu Thr Val Asn Val Pro
145                 150                 155

<210> SEQ ID NO 4
<211> LENGTH: 156
<212> TYPE: PRT
<213> ORGANISM: Bacillus thuringiensis

<400> SEQUENCE: 4

Ala Val Asn Ala Leu Phe Thr Ser Thr Asn Gln Leu Gly Leu Lys Thr

```
                1               5                   10                  15
            Asn Val Thr Asp Tyr His Ile Asp Gln Val Ser Asn Leu Val Thr Tyr
                            20                  25                  30
            Leu Ser Asp Glu Phe Cys Leu Asp Glu Lys Arg Glu Leu Ser Glu Lys
                        35                  40                  45
            Val Lys His Ala Lys Arg Leu Ser Asp Glu Arg Asn Leu Leu Gln Asp
                    50                  55                  60
            Ser Asn Phe Lys Asp Ile Asn Arg Gln Pro Glu Arg Gly Trp Gly Gly
            65                  70                  75                  80
            Ser Thr Gly Ile Thr Ile Gln Gly Gly Asp Val Phe Lys Glu Asn
                            85                  90                  95
            Tyr Val Thr Leu Ser Gly Thr Phe Asp Glu Cys Tyr Pro Thr Tyr Leu
                            100                 105                 110
            Tyr Gln Lys Ile Asp Glu Ser Lys Leu Lys Ala Phe Thr Arg Tyr Gln
                            115                 120                 125
            Leu Arg Gly Tyr Ile Glu Asp Ser Gln Asp Leu Glu Ile Tyr Leu Ile
                            130                 135                 140
            Arg Tyr Asn Ala Lys His Glu Thr Val Asn Val Pro
            145                 150                 155
```

<210> SEQ ID NO 5
<211> LENGTH: 156
<212> TYPE: PRT
<213> ORGANISM: Bacillus thuringiensis

<400> SEQUENCE: 5

```
            Ala Val Asn Ala Leu Phe Thr Ser Thr Asn Gln Leu Gly Leu Lys Thr
            1               5                   10                  15
            Asn Val Thr Asp Tyr His Ile Asp Gln Val Ser Asn Leu Val Thr Cys
                            20                  25                  30
            Leu Ser Asp Glu Phe Cys Leu Asp Glu Lys Arg Glu Leu Ser Glu Lys
                        35                  40                  45
            Val Lys His Ala Lys Arg Leu Ser Asp Glu Arg Asn Leu Leu Gln Asp
                    50                  55                  60
            Ser Asn Phe Lys Asp Ile Asn Arg Gln Pro Glu Arg Gly Trp Gly Gly
            65                  70                  75                  80
            Ser Thr Gly Ile Thr Ile Gln Gly Gly Asp Val Phe Lys Glu Asn
                            85                  90                  95
            Tyr Val Thr Leu Ser Gly Thr Phe Asp Glu Cys Tyr Pro Thr Tyr Leu
                            100                 105                 110
            Tyr Gln Lys Ile Asp Glu Ser Lys Leu Lys Ala Phe Thr Arg Tyr Gln
                            115                 120                 125
            Leu Arg Gly Tyr Ile Glu Asp Ser Gln Asp Leu Glu Ile Tyr Leu Ile
                            130                 135                 140
            Arg Tyr Asn Ala Lys His Glu Thr Val Asn Val Pro
            145                 150                 155
```

<210> SEQ ID NO 6
<211> LENGTH: 156
<212> TYPE: PRT
<213> ORGANISM: Bacillus thuringiensis

<400> SEQUENCE: 6

```
            Ile Ile Asn Thr Phe Tyr Ala Asn Pro Ile Lys Asn Thr Leu Gln Ser
            1               5                   10                  15
            Glu Leu Thr Asp Tyr Asp Ile Asp Gln Ala Ala Asn Leu Val Glu Cys
```

```
                    20                  25                  30
Ile Ser Glu Glu Leu Tyr Pro Lys Glu Lys Met Leu Leu Asp Glu
            35                  40                  45

Val Lys Asn Ala Lys Gln Leu Ser Gln Ser Arg Asn Val Leu Gln Asn
        50                  55                  60

Gly Asp Phe Glu Ser Ala Thr Leu Gly Trp Thr Thr Ser Asp Asn Ile
65                  70                  75                  80

Thr Ile Gln Glu Asp Asp Pro Ile Phe Lys Gly His Tyr Leu His Met
                85                  90                  95

Ser Gly Ala Arg Asp Ile Asp Gly Thr Ile Phe Pro Thr Tyr Ile Phe
            100                 105                 110

Gln Lys Ile Asp Glu Ser Lys Leu Lys Pro Tyr Thr Arg Tyr Leu Val
        115                 120                 125

Arg Gly Phe Val Gly Ser Ser Lys Asp Val Glu Leu Val Val Ser Arg
    130                 135                 140

Tyr Gly Glu Glu Ile Asp Ala Ile Met Asn Val Pro
145                 150                 155

<210> SEQ ID NO 7
<211> LENGTH: 29
<212> TYPE: PRT
<213> ORGANISM: Bacillus thuringiensis

<400> SEQUENCE: 7

Ile Phe Pro Thr Tyr Ile Phe Gln Lys Ile Asp Glu Ser Lys Leu Lys
1               5                   10                  15

Pro Tyr Thr Arg Tyr Leu Val Arg Gly Phe Val Gly Ser
                20                  25

<210> SEQ ID NO 8
<211> LENGTH: 156
<212> TYPE: PRT
<213> ORGANISM: Bacillus thuringiensis

<400> SEQUENCE: 8

Val Val Asn Ala Leu Phe Thr Asn Asp Ala Lys Asp Ala Leu Asn Ile
1               5                   10                  15

Gly Thr Thr Asp Tyr Asp Ile Asp Gln Ala Ala Asn Leu Val Glu Cys
                20                  25                  30

Ile Ser Glu Glu Leu Tyr Pro Lys Glu Lys Met Leu Leu Asp Glu
            35                  40                  45

Val Lys Asn Ala Lys Gln Leu Ser Gln Ser Arg Asn Val Leu Gln Asn
        50                  55                  60

Gly Asp Phe Glu Ser Ala Thr Leu Gly Trp Thr Thr Ser Asp Asn Ile
65                  70                  75                  80

Thr Ile Gln Glu Asp Asp Pro Ile Phe Lys Gly His Tyr Leu His Met
                85                  90                  95

Ser Gly Ala Arg Asp Ile Asp Gly Thr Ile Phe Pro Thr Tyr Ile Phe
            100                 105                 110

Gln Lys Ile Asp Glu Ser Lys Leu Lys Pro Tyr Thr Arg Tyr Leu Val
        115                 120                 125

Arg Gly Phe Val Gly Ser Ser Lys Asp Val Glu Leu Val Val Ser Arg
    130                 135                 140

Tyr Gly Glu Glu Ile Asp Ala Ile Met Asn Val Pro
145                 150                 155
```

```
<210> SEQ ID NO 9
<211> LENGTH: 29
<212> TYPE: PRT
<213> ORGANISM: Bacillus thuringiensis

<400> SEQUENCE: 9

Ile Phe Pro Thr Tyr Ile Phe Gln Lys Ile Asp Glu Ser Lys Leu Lys
1               5                   10                  15

Pro Tyr Thr Arg Tyr Leu Val Arg Gly Phe Val Gly Ser
            20                  25

<210> SEQ ID NO 10
<211> LENGTH: 156
<212> TYPE: PRT
<213> ORGANISM: Bacillus thuringiensis

<400> SEQUENCE: 10

Val Val Asn Ala Leu Phe Thr Asn Asp Ala Lys Asp Ala Leu Asn Ile
1               5                   10                  15

Gly Thr Thr Asp Tyr Asp Ile Asp Gln Ala Ala Asn Leu Val Glu Cys
            20                  25                  30

Ile Ser Glu Glu Leu Tyr Pro Lys Glu Lys Met Leu Leu Leu Asp Glu
        35                  40                  45

Val Lys Asn Ala Lys Gln Leu Ser Gln Ser Arg Asn Val Leu Gln Asn
    50                  55                  60

Gly Asp Phe Glu Ser Ala Thr Leu Gly Trp Thr Thr Ser Asp Asn Ile
65                  70                  75                  80

Thr Ile Gln Glu Asp Asp Pro Ile Phe Lys Gly His Tyr Leu His Met
                85                  90                  95

Ser Gly Ala Arg Asp Ile Asp Gly Thr Ile Phe Pro Thr Tyr Ile Phe
            100                 105                 110

Gln Lys Ile Asp Glu Ser Lys Leu Lys Pro Tyr Thr Arg Tyr Leu Val
        115                 120                 125

Arg Gly Phe Val Gly Ser Ser Lys Asp Val Leu Val Val Ser Arg
    130                 135                 140

Tyr Gly Glu Glu Ile Asp Ala Ile Met Asn Val Pro
145                 150                 155

<210> SEQ ID NO 11
<211> LENGTH: 29
<212> TYPE: PRT
<213> ORGANISM: Bacillus thuringiensis

<400> SEQUENCE: 11

Ile Phe Pro Thr Tyr Ile Phe Gln Lys Ile Asp Glu Ser Lys Leu Lys
1               5                   10                  15

Pro Tyr Thr Arg Tyr Leu Val Arg Gly Phe Val Gly Ser
            20                  25

<210> SEQ ID NO 12
<211> LENGTH: 156
<212> TYPE: PRT
<213> ORGANISM: Bacillus thuringiensis

<400> SEQUENCE: 12

Val Val Asn Ala Leu Phe Thr Asn Asp Ala Lys Asp Ala Leu Asn Ile
1               5                   10                  15

Gly Thr Thr Asp Tyr Asp Ile Asp Gln Ala Ala Asn Leu Val Glu Cys
            20                  25                  30
```

```
Ile Ser Glu Gly Ile Ile Ser Lys Glu Lys Met Leu Leu Asp Glu
             35                  40                  45

Val Lys Asn Ala Lys Gln Leu Ser Gln Ser Arg Asn Val Leu Gln Asn
 50                  55                  60

Gly Asp Phe Glu Ser Arg Thr Leu Gly Trp Thr Thr Ser Asp Asn Ile
 65                  70                  75                  80

Thr Ile Gln Glu Asp Asp Pro Ile Phe Lys Gly His Tyr Leu His Met
                 85                  90                  95

Ser Gly Ala Arg Asp Ile Asp Gly Thr Ile Phe Pro Thr Tyr Ile Phe
                100                 105                 110

Gln Lys Ile Asp Glu Ser Lys Leu Lys Pro Tyr Thr Arg Tyr Leu Val
                115                 120                 125

Arg Gly Phe Val Gly Ser Ser Lys Asp Val Glu Leu Val Val Ser Arg
                130                 135                 140

Tyr Gly Glu Glu Ile Asp Ala Ile Met Asn Val Pro
145                 150                 155

<210> SEQ ID NO 13
<211> LENGTH: 29
<212> TYPE: PRT
<213> ORGANISM: Bacillus thuringiensis

<400> SEQUENCE: 13

Ile Phe Pro Thr Tyr Ile Phe Gln Lys Ile Asp Glu Ser Lys Leu Lys
1               5                   10                  15

Pro Tyr Thr Arg Tyr Leu Val Arg Gly Phe Val Gly Ser
                20                  25

<210> SEQ ID NO 14
<211> LENGTH: 158
<212> TYPE: PRT
<213> ORGANISM: Bacillus thuringiensis

<400> SEQUENCE: 14

Lys Lys Ala Val Asn Gly Leu Phe Thr Asn Glu Lys Asp Ala Leu Gln
1               5                   10                  15

Thr Ser Val Thr Asp Tyr Gln Val Asn Gln Ala Ala Asn Leu Ile Glu
                20                  25                  30

Cys Leu Ser Asp Glu Leu Tyr Pro Asn Glu Lys Arg Met Leu Trp Asp
                35                  40                  45

Ala Val Lys Glu Ala Lys Arg Leu Val Gln Ala Arg Asn Leu Leu Gln
 50                  55                  60

Asp Thr Gly Phe Asn Arg Ile Asn Gly Glu Asn Gly Trp Thr Gly Ser
 65                  70                  75                  80

Thr Gly Ile Glu Val Val Glu Gly Asp Val Leu Phe Lys Asp Arg Ser
                 85                  90                  95

Leu Arg Leu Thr Ser Ala Arg Glu Ile Asp Thr Glu Thr Tyr Pro Thr
                100                 105                 110

Tyr Leu Tyr Gln Gln Ile Asp Glu Ser Leu Leu Lys Pro Tyr Thr Arg
                115                 120                 125

Tyr Lys Leu Lys Gly Phe Ile Gly Ser Ser Gln Asp Leu Glu Ile Lys
                130                 135                 140

Leu Ile Arg His Arg Ala Asn Gln Ile Val Lys Asn Val Pro
145                 150                 155

<210> SEQ ID NO 15
<211> LENGTH: 69
```

```
<212> TYPE: DNA
<213> ORGANISM: Artificial
<220> FEATURE:
<223> OTHER INFORMATION: Primer C1-1-f

<400> SEQUENCE: 15
caagaattcg atatcatcaa caccttctac gcaaacccga tcaagaacac cctgcaatcg    60
gaactgacc                                                            69

<210> SEQ ID NO 16
<211> LENGTH: 77
<212> TYPE: DNA
<213> ORGANISM: Artificial
<220> FEATURE:
<223> OTHER INFORMATION: Primer C1-1&2-r

<400> SEQUENCE: 16
ggtacaactc ttcgctaata cattccacca gatttgccgc ttggtcgatg tcgtagtcgg    60
tcagttccga ttgcagg                                                   77

<210> SEQ ID NO 17
<211> LENGTH: 71
<212> TYPE: DNA
<213> ORGANISM: Artificial
<220> FEATURE:
<223> OTHER INFORMATION: Primer C1-2&3-f

<400> SEQUENCE: 17
ggaatgtatt agcgaagagt tgtacccgaa agaaaagatg ctgttgttgg acgaagtgaa    60
gaacgcaaag c                                                         71

<210> SEQ ID NO 18
<211> LENGTH: 73
<212> TYPE: DNA
<213> ORGANISM: Artificial
<220> FEATURE:
<223> OTHER INFORMATION: Primer C1-3&4-r

<400> SEQUENCE: 18
cgtagccgat tcgaagtcgc cgttttgcag cacgttacgc gattggctca gttgctttgc    60
gttcttcact tcg                                                       73

<210> SEQ ID NO 19
<211> LENGTH: 67
<212> TYPE: DNA
<213> ORGANISM: Artificial
<220> FEATURE:
<223> OTHER INFORMATION: Primer C1-4&5-f

<400> SEQUENCE: 19
cgacttcgaa tcggctacgc tgggttggac cacgagcgac aatatcacca ttcaagaaga    60
cgatccg                                                              67

<210> SEQ ID NO 20
<211> LENGTH: 83
<212> TYPE: DNA
<213> ORGANISM: Artificial
<220> FEATURE:
<223> OTHER INFORMATION: Primer C1-5&6-r

<400> SEQUENCE: 20
cgggaagatg gtaccatcga tgtcacgcgc gccggacatg tgcaggtaat ggcctttgaa    60
```
aatcggatcg tcttcttgaa tgg         83

<210> SEQ ID NO 21
<211> LENGTH: 67
<212> TYPE: DNA
<213> ORGANISM: Artificial
<220> FEATURE:
<223> OTHER INFORMATION: Primer C1-6&7-f

<400> SEQUENCE: 21
cgatggtacc atcttcccga cctacatctt ccaaaagatc gatgaatcga aattgaagcc         60
gtacacc         67

<210> SEQ ID NO 22
<211> LENGTH: 63
<212> TYPE: DNA
<213> ORGANISM: Artificial
<220> FEATURE:
<223> OTHER INFORMATION: Primer C1-7&8-r

<400> SEQUENCE: 22
cgacgtcctt gctgctaccc acgaaaccac gcaccaggta acgggtgtac ggcttcaatt         60
tcg         63

<210> SEQ ID NO 23
<211> LENGTH: 70
<212> TYPE: DNA
<213> ORGANISM: Artificial
<220> FEATURE:
<223> OTHER INFORMATION: Primer C1-8&9-f

<400> SEQUENCE: 23
ggtagcagca aggacgtcga actggtggtc tcgcgctacg gcgaagaaat cgatgcaatc         60
atgaatgtgc         70

<210> SEQ ID NO 24
<211> LENGTH: 58
<212> TYPE: DNA
<213> ORGANISM: Artificial
<220> FEATURE:
<223> OTHER INFORMATION: Primer C1-9-r

<400> SEQUENCE: 24
gtcgaaggtc gacgggtaca ggtagttcaa gtctgccggc acattcatga ttgcatcg         58

<210> SEQ ID NO 25
<211> LENGTH: 468
<212> TYPE: DNA
<213> ORGANISM: Artificial
<220> FEATURE:
<223> OTHER INFORMATION: 4ACter(696-851) coding DNA

<400> SEQUENCE: 25
atcatcaaca ccttctacgc aaacccgatc aagaacaccc tgcaatcgga actgaccgac         60
tacgacatcg accaagcggc aaatctggtg gaatgtatta gcgaagagtt gtacccgaaa        120
gaaaagatgc tgttgttgga cgaagtgaag aacgcaaagc aactgagcca atcgcgtaac        180
gtgctgcaaa acggcgactt cgaatcggct acgctgggtt ggaccacgag cgacaatatc        240
accattcaag aagacgatcc gattttcaaa ggccattacc tgcacatgtc cggcgcgcgt        300
gacatcgatg gtaccatctt cccgacctac atcttccaaa agatcgatga atcgaaattg        360
aagccgtaca cccgttacct ggtgcgtggt ttcgtgggta gcagcaagga cgtcgaactg        420

```
gtggtctcgc gctacggcga agaaatcgat gcaatcatga atgtgccg            468
```

<210> SEQ ID NO 26
<211> LENGTH: 3543
<212> TYPE: DNA
<213> ORGANISM: Artificial
<220> FEATURE:
<223> OTHER INFORMATION: syn4A ORF

<400> SEQUENCE: 26

```
atgaacccgt accaaaacaa gaacgaatac gaaaccctga cgcgagccga agaaactg     60
aacatcagca caactacac  ccgttacccg atcgaaaaca gcccgaaaca actgctgcaa  120
agcaccaact acaagactg  gctgaacatg tgccaacaaa ccaacaata cggcggcgac   180
ttcgaaacct tcatcgacag cggtgaactg agcgcgtaca ccatcgtggt cggcaccgtg  240
ctgaccggtt tcggcttcac caccccgctg ggcctggcgc tgatcggttt cggtacccctg 300
atcccggtgc tgttcccggc gaagaccaa  agcaacacct ggagcgactt catcacccaa  360
accaaaaaca tcatcaaaaa agaaatcgca agcacctaca tcagcaacgc gaacaaaatc  420
ctgaaccgta gcttcaacgt gatcagcacc taccacaacc acctgaaaac ctgggaaaac  480
aacccgaacc cgcaaaacac ccaagacgtg cgtacccaaa tccaactggt gcactaccac  540
ttccaaaacg tcatcccgga actggtgaac agctgcccgc cgaacccgag cgactgcgac  600
tactacaaca tcctggtgct gagcagctac gcgcaagcag cgaacctgca cctgaccgtg  660
ctgaaccaag cggtcaaatt cgaggcttac ctgaaaaaca ccgccaattt cgactacctc  720
gagccgctgc cgaccgcaat cgactactac ccggtgctga ccaaagcaat cgaagactac  780
accaactact gcgtgaccac ctacaaaaaa ggcctgaacc tgatcaaaac cacccccggac 840
agcaacctgg acggcaacat caactggaac acctacaaca cctaccgcac caaaatgacc  900
accgcggtgc tggacctggt ggcactgttc ccgaactacg acgtcggtaa atacccgatc  960
ggtgtccaaa gcgaactgac ccgggaaatc taccaagtcc tgaacttcga agaaagcccg 1020
tacaaatact acgacttcca ataccaagaa gacagcctga cccgtcgccc gcacctgttc 1080
acctggctgg acagcctgaa cttctacgaa aaagcgcaaa ccaccccgaa caacttcttc 1140
accagccact acaacatgtt ccactacacc ctggacaaca tcagccaaaa aagcagcgtg 1200
ttcggcaacc acaacgtgac cgacaaactg aaaagcctgg gtctggcaac caacatctac 1260
atcttcctgc tgaacgtcat cagcctggac aacaaatacc tgaacgacta caacaacatc 1320
agcaaaatgg acttcttcat caccaacggt acccgcctgc tggaaaaaga actgaccgca 1380
ggcagcggcc aaatcaccta cgacgtgaac aaaaacatct tcggcctgcc gatcctgaaa 1440
cgtcgcgaaa accaaggcaa cccgaccctg ttcccgacct acgacaacta cagccacatc 1500
ctgagcttca tcaaaagcct gagcatcccg gcaacctaca aacccaagt gtacaccttc 1560
gcgtggaccc cagcagcgt cgacccgaaa acaccatct acacccacct gaccacccaa 1620
atcccggcgg tgaaagcgaa cagcctgggc accgcgagca agtggtccaa ggtccgggt  1680
cacaccggcg gtgacctgat cgacttcaaa gaccacttca aaatcacctg ccaacacagc 1740
aacttccaac aaagctactt catccgcatc cgttacgcga gcaacggcag cgcaaacacc 1800
cgcgcggtga tcaacctgag catccctggc gtggcagaac tgggtatggc actgaacccg 1860
accttcagcg gtaccgacta caccaacctg aaatacaaag acttccaata cctggagttc 1920
agcaacgaag tgaaattcgc gccgaaccaa acatcagcc tggtgttcaa ccgtagcgac 1980
```

```
gtgtacacca acaccaccgt gctgatcgac aaaatcgagt tcctgccgat cacccgtagc    2040
atccgcgaag accgtgaaaa acaaaaactg gaaaccgtgc aacaaatcat caacaccttc    2100
tacgcaaacc cgatcaagaa caccctgcaa tcggaactga ccgactacga catcgaccaa    2160
gcggcaaatc tggtggaatg tattagcgaa gagttgtacc cgaaagaaaa gatgctgttg    2220
ttggacgaag tgaagaacgc aaagcaactg agccaatcgc gtaacgtgct gcaaaacggc    2280
gacttcgaat cggctacgct gggttggacc acgagcgaca atatcaccat tcaagaagac    2340
gatccgattt tcaaaggcca ttacctgcac atgtccggcg cgcgtgacat cgatggtacc    2400
atcttcccga cctacatctt ccaaaagatc gatgaatcga aattgaagcc gtacacccgt    2460
tacctggtgc gtggtttcgt gggtagcagc aaggacgtcg aactggtggt ctcgcgctac    2520
ggcgaagaaa tcgatgcaat catgaatgtg ccggcagact tgaactacct gtacccgtcg    2580
accttcgact gcgaaggctc gaaccgttgc gagaccagcg ctgtcccggc aaacatcggc    2640
aacacctctg acatgctgta ctcgtgccaa tacgacaccg gcaagaaaca cgtcgtgtgc    2700
caggactccc atcagttcag cttcaccatc gacaccggtg cactggacac gaacgaaaac    2760
atcggcgtgt gggtcatgtt caaaatcagc tcgccggacg gctacgcatc cttggacaac    2820
ctggaagtga tcgaggaagg cccgatcgac ggcgaagcgc tgtcgcgcgt gaaacacatg    2880
gagaagaaat ggaacgacca aatggaagcg aaacgttcgg aaacccagca agcatacgac    2940
gtggcgaaac aagccatcga cgctctgttc accaacgtgc aagacgaggc tctgcagttc    3000
gacaccaccc tggctcaaat ccaatacgct gaatacttgg tgcaatcgat tccatatgtg    3060
tacaacgact ggctgtcgga cgtgccgggt atgaactacg acatctacgt ggagctggac    3120
gcacgtgtgg cacaagcgcg ttacctgtac gacacccgta acatcatcaa gaacggtgac    3180
ttcacccaag cgtcatggg ttggcatgtg accggcaacg cagacgtgca acaaatcgac    3240
ggtgtgtcgg tgctggtgct gagcaactgg agcgcaggcg tctcgcaaaa cgtccatctg    3300
caacataacc atggctacgt cttgcgtgtg atcgcgaaaa aggaaggccc gggcaacggc    3360
tacgtcaccc tgatggactg cgaggagaac caagaaaaac tgaccttcac ctcgtgcgaa    3420
gaaggctaca tcaccaagac cgtggacgtg ttcccggaca ccgaccgtgt gcgtatcgaa    3480
atcggcgaaa ccgaaggttc gttctacatc gaaagcatcg aattgatctg catgaacgaa    3540
tga                                                                  3543
```

<210> SEQ ID NO 27
<211> LENGTH: 26
<212> TYPE: DNA
<213> ORGANISM: Artificial
<220> FEATURE:
<223> OTHER INFORMATION: Primer X-Syn4A-C1-f

<400> SEQUENCE: 27
ggctcgagat catcaacacc ttctac                                          26

<210> SEQ ID NO 28
<211> LENGTH: 31
<212> TYPE: DNA
<213> ORGANISM: Artificial
<220> FEATURE:
<223> OTHER INFORMATION: Primer X-S-Syn4A-C1-r

<400> SEQUENCE: 28
ggctcgagcc cgggccggca cattcatgat t                                    31

```
<210> SEQ ID NO 29
<211> LENGTH: 66
<212> TYPE: DNA
<213> ORGANISM: Artificial
<220> FEATURE:
<223> OTHER INFORMATION: pGEX-6P-1 cloning site
<220> FEATURE:
<221> NAME/KEY: CDS
<222> LOCATION: (1)..(66)
<223> OTHER INFORMATION:

<400> SEQUENCE: 29 ctg gaa gtt ctg ttc cag ggg ccc ctg gga tcc ccg gaa ttc ccg ggt    48
Leu Glu Val Leu Phe Gln Gly Pro Leu Gly Ser Pro Glu Phe Pro Gly
1               5                   10                  15 cga ctc gag cgg ccg cat                                            66
Arg Leu Glu Arg Pro His
            20

<210> SEQ ID NO 30
<211> LENGTH: 22
<212> TYPE: PRT
<213> ORGANISM: Artificial
<220> FEATURE:
<223> OTHER INFORMATION: pGEX-6P-1 cloning site

<400> SEQUENCE: 30

Leu Glu Val Leu Phe Gln Gly Pro Leu Gly Ser Pro Glu Phe Pro Gly
1               5                   10                  15

Arg Leu Glu Arg Pro His
            20

<210> SEQ ID NO 31
<211> LENGTH: 34
<212> TYPE: PRT
<213> ORGANISM: Bacillus thuringiensis

<400> SEQUENCE: 31

Ile Phe Pro Thr Tyr Ile Phe Gln Lys Ile Asp Glu Ser Lys Leu Lys
1               5                   10                  15

Pro Tyr Thr Arg Tyr Leu Val Arg Gly Phe Val Gly Ser Ser Lys Asp
            20                  25                  30

Val Glu

<210> SEQ ID NO 32
<211> LENGTH: 915
<212> TYPE: DNA
<213> ORGANISM: Bacillus thuringiensis
<220> FEATURE:
<221> NAME/KEY: CDS
<222> LOCATION: (1)..(915)
<223> OTHER INFORMATION:

<400> SEQUENCE: 32 atg tat tat act acc caa gta aca ggt gga ttt caa gct gat ttg aat    48
Met Tyr Tyr Thr Thr Gln Val Thr Gly Gly Phe Gln Ala Asp Leu Asn
1               5                   10                  15 aat caa gta gtg gaa aca ttt caa cca agt aca aat gtt att caa gaa    96
Asn Gln Val Val Glu Thr Phe Gln Pro Ser Thr Asn Val Ile Gln Glu
            20                  25                  30 tac ctt acg ttt aat gac tta cca gca tta ggt tca gtc cca caa agt    144
Tyr Leu Thr Phe Asn Asp Leu Pro Ala Leu Gly Ser Val Pro Gln Ser
        35                  40                  45 gta cgc tct aga ttt tca tct att tat ggt acc aat cca gat ggt att    192
Val Arg Ser Arg Phe Ser Ser Ile Tyr Gly Thr Asn Pro Asp Gly Ile
```

```
                  50                  55                  60
gca tta aat aat gaa aca tat ttt agc gct gta caa cca cca att act       240
Ala Leu Asn Asn Glu Thr Tyr Phe Ser Ala Val Gln Pro Pro Ile Thr
 65                  70                  75                  80 gtt caa tat gga cac tat tgt tat aaa aat gtt ggg act gtt cag tac       288
Val Gln Tyr Gly His Tyr Cys Tyr Lys Asn Val Gly Thr Val Gln Tyr
                     85                  90                  95 gta aat aga ccc act gat att aac cca aac gtt att ctc gct caa gac       336
Val Asn Arg Pro Thr Asp Ile Asn Pro Asn Val Ile Leu Ala Gln Asp
                100                 105                 110 aca tta aca aac aat act aat gag cca ttt act acg acc ata act tta       384
Thr Leu Thr Asn Asn Thr Asn Glu Pro Phe Thr Thr Thr Ile Thr Leu
                115                 120                 125 aca gga tct tgg acc aaa tca tcc acg gtt aca tct agt aca aca aca       432
Thr Gly Ser Trp Thr Lys Ser Ser Thr Val Thr Ser Ser Thr Thr Thr
                130                 135                 140 ggt ctt aaa att acc act aaa cta tcg att aaa aaa gtc ttt gaa att       480
Gly Leu Lys Ile Thr Thr Lys Leu Ser Ile Lys Lys Val Phe Glu Ile
145                 150                 155                 160 ggt gga gaa gtt tca ttc tct act aca att gga tca tct gaa gca act       528
Gly Gly Glu Val Ser Phe Ser Thr Thr Ile Gly Ser Ser Glu Ala Thr
                    165                 170                 175 tca gaa aca ttt act gta tcg aaa gcc gtg acg gtc aca gtt cca gct       576
Ser Glu Thr Phe Thr Val Ser Lys Ala Val Thr Val Thr Val Pro Ala
                180                 185                 190 caa agt aga agg aat att caa tta aca gca aaa ata gca aga gaa tct       624
Gln Ser Arg Arg Asn Ile Gln Leu Thr Ala Lys Ile Ala Arg Glu Ser
                195                 200                 205 gca gat ttt agt gct cct att act gtg gat ggt tac ttt ggt gct aat       672
Ala Asp Phe Ser Ala Pro Ile Thr Val Asp Gly Tyr Phe Gly Ala Asn
                210                 215                 220 ttt cct cgt cga gta ggt ccg gga gga cat tac ttt tgg ttt aat cct       720
Phe Pro Arg Arg Val Gly Pro Gly Gly His Tyr Phe Trp Phe Asn Pro
225                 230                 235                 240 gct aga gat gtt tta aat gct acc tcc ggt aca cta aga ggt acc gtg       768
Ala Arg Asp Val Leu Asn Ala Thr Ser Gly Thr Leu Arg Gly Thr Val
                    245                 250                 255 acg aat gta tct agt ttc gac ttc caa act gta gta caa cca gca tat       816
Thr Asn Val Ser Ser Phe Asp Phe Gln Thr Val Val Gln Pro Ala Tyr
                260                 265                 270 agt tta ctg gct gaa cag caa gaa gct tta gaa tct gcc ata tct gga       864
Ser Leu Leu Ala Glu Gln Gln Glu Ala Leu Glu Ser Ala Ile Ser Gly
                275                 280                 285 gat cct tct gag gaa caa ttg aaa caa ata caa caa aca att gga tta       912
Asp Pro Ser Glu Glu Gln Leu Lys Gln Ile Gln Gln Thr Ile Gly Leu
                290                 295                 300 taa                                                                   915

<210> SEQ ID NO 33
<211> LENGTH: 304
<212> TYPE: PRT
<213> ORGANISM: Bacillus thuringiensis

<400> SEQUENCE: 33

Met Tyr Tyr Thr Thr Gln Val Thr Gly Gly Phe Gln Ala Asp Leu Asn
1               5                   10                  15

Asn Gln Val Val Glu Thr Phe Gln Pro Ser Thr Asn Val Ile Gln Glu
            20                  25                  30

Tyr Leu Thr Phe Asn Asp Leu Pro Ala Leu Gly Ser Ser Pro Gln Ser
```

-continued

```
                    35                   40                   45
Val Arg Ser Arg Phe Ser Ser Ile Tyr Gly Thr Asn Pro Asp Gly Ile
 50                   55                   60

Ala Leu Asn Asn Glu Thr Tyr Phe Ser Ala Val Gln Pro Pro Ile Thr
 65                   70                   75                   80

Val Gln Tyr Gly His Tyr Cys Tyr Lys Asn Val Gly Thr Val Gln Tyr
                 85                   90                   95

Val Asn Arg Pro Thr Asp Ile Asn Pro Asn Val Ile Leu Ala Gln Asp
                100                  105                  110

Thr Leu Thr Asn Asn Thr Asn Glu Pro Phe Thr Thr Ile Thr Leu
            115                  120                  125

Thr Gly Ser Trp Thr Lys Ser Ser Thr Val Thr Ser Ser Thr Thr Thr
            130                  135                  140

Gly Leu Lys Ile Thr Thr Lys Leu Ser Ile Lys Lys Val Phe Glu Ile
145                  150                  155                  160

Gly Gly Glu Val Ser Phe Ser Thr Thr Ile Gly Ser Ser Glu Ala Thr
                165                  170                  175

Ser Glu Thr Phe Thr Val Ser Lys Ala Val Thr Val Thr Val Pro Ala
                180                  185                  190

Gln Ser Arg Arg Asn Ile Gln Leu Thr Ala Lys Ile Ala Arg Glu Ser
            195                  200                  205

Ala Asp Phe Ser Ala Pro Ile Thr Val Asp Gly Tyr Phe Gly Ala Asn
210                  215                  220

Phe Pro Arg Arg Val Gly Pro Gly His Tyr Phe Trp Phe Asn Pro
225                  230                  235                  240

Ala Arg Asp Val Leu Asn Ala Thr Ser Gly Thr Leu Arg Gly Thr Val
                245                  250                  255

Thr Asn Val Ser Ser Phe Asp Phe Gln Thr Val Val Gln Pro Ala Tyr
                260                  265                  270

Ser Leu Leu Ala Glu Gln Gln Glu Ala Leu Glu Ser Ala Ile Ser Gly
            275                  280                  285

Asp Pro Ser Glu Glu Gln Leu Lys Gln Ile Gln Gln Thr Ile Gly Leu
290                  295                  300
```

<210> SEQ ID NO 34
<211> LENGTH: 759
<212> TYPE: DNA
<213> ORGANISM: Bacillus thuringiensis
<220> FEATURE:
<221> NAME/KEY: CDS
<222> LOCATION: (1)

```
Thr Val Gln Tyr Val Asn Arg Pro Thr Asp Ile Asn Pro Asn Val Ile
 65                  70                  75                  80 ctc gct caa gac aca tta aca aac aat act aat gag cca ttt act acg   288
Leu Ala Gln Asp Thr Leu Thr Asn Asn Thr Asn Glu Pro Phe Thr Thr
                 85                  90                  95 acc ata act tta aca gga tct tgg acc aaa tca tcc acg gtt aca tct   336
Thr Ile Thr Leu Thr Gly Ser Trp Thr Lys Ser Ser Thr Val Thr Ser
            100                 105                 110 agt aca aca aca ggt ctt aaa att acc act aaa cta tcg att aaa aaa   384
Ser Thr Thr Thr Gly Leu Lys Ile Thr Thr Lys Leu Ser Ile Lys Lys
        115                 120                 125 gtc ttt gaa att ggt gga gaa gtt tca ttc tct act aca att gga tca   432
Val Phe Glu Ile Gly Gly Glu Val Ser Phe Ser Thr Thr Ile Gly Ser
    130                 135                 140 tct gaa gca act tca gaa aca ttt act gta tcg aaa gcc gtg acg gtc   480
Ser Glu Ala Thr Ser Glu Thr Phe Thr Val Ser Lys Ala Val Thr Val
145                 150                 155                 160 aca gtt cca gct caa agt aga agg aat att caa tta aca gca aaa ata   528
Thr Val Pro Ala Gln Ser Arg Arg Asn Ile Gln Leu Thr Ala Lys Ile
                165                 170                 175 gca aga gaa tct gca gat ttt agt gct cct att act gtg gat ggt tac   576
Ala Arg Glu Ser Ala Asp Phe Ser Ala Pro Ile Thr Val Asp Gly Tyr
            180                 185                 190 ttt ggt gct aat ttt cct cgt cga gta ggt ccg ggg gga cat tac ttt   624
Phe Gly Ala Asn Phe Pro Arg Arg Val Gly Pro Gly Gly His Tyr Phe
        195                 200                 205 tgg ttt aat cct gct aga gat gtt tta aat gct acc tcc ggt aca cta   672
Trp Phe Asn Pro Ala Arg Asp Val Leu Asn Ala Thr Ser Gly Thr Leu
    210                 215                 220 aga ggt acc gtg acg aat gta tct agt ttc gac ttc caa act gta gta   720
Arg Gly Thr Val Thr Asn Val Ser Ser Phe Asp Phe Gln Thr Val Val
225                 230                 235                 240 caa cca gca tat agt tta ctg gct gaa cag caa gaa gct                759
Gln Pro Ala Tyr Ser Leu Leu Ala Glu Gln Gln Glu Ala
                245                 250

<210> SEQ ID NO 35
<211> LENGTH: 253
<212> TYPE: PRT
<213> ORGANISM: Bacillus thuringiensis

<400> SEQUENCE: 35

Val Ile Gln Glu Tyr Leu Thr Phe Asn Asp Leu Pro Ala Leu Gly Ser
1               5                   10                  15

Ser Pro Gln Ser Val Arg Ser Arg Phe Ser Ser Ile Tyr Gly Thr Asn
            20                  25                  30

Pro Asp Gly Ile Ala Leu Asn Asn Glu Thr Tyr Phe Ser Ala Val Gln
        35                  40                  45

Pro Pro Ile Thr Val Gln Tyr Gly His Tyr Cys Tyr Lys Asn Val Gly
    50                  55                  60

Thr Val Gln Tyr Val Asn Arg Pro Thr Asp Ile Asn Pro Asn Val Ile
65                  70                  75                  80

Leu Ala Gln Asp Thr Leu Thr Asn Asn Thr Asn Glu Pro Phe Thr Thr
                85                  90                  95

Thr Ile Thr Leu Thr Gly Ser Trp Thr Lys Ser Ser Thr Val Thr Ser
            100                 105                 110

Ser Thr Thr Thr Gly Leu Lys Ile Thr Thr Lys Leu Ser Ile Lys Lys
        115                 120                 125
```

```
Val Phe Glu Ile Gly Gly Glu Val Ser Phe Ser Thr Thr Ile Gly Ser
        130                 135                 140

Ser Glu Ala Thr Ser Glu Thr Phe Thr Val Ser Lys Ala Val Thr Val
145                 150                 155                 160

Thr Val Pro Ala Gln Ser Arg Arg Asn Ile Gln Leu Thr Ala Lys Ile
                165                 170                 175

Ala Arg Glu Ser Ala Asp Phe Ser Ala Pro Ile Thr Val Asp Gly Tyr
            180                 185                 190

Phe Gly Ala Asn Phe Pro Arg Arg Val Gly Pro Gly His Tyr Phe
        195                 200                 205

Trp Phe Asn Pro Ala Arg Asp Val Leu Asn Ala Thr Ser Gly Thr Leu
210                 215                 220

Arg Gly Thr Val Thr Asn Val Ser Ser Phe Asp Phe Gln Thr Val Val
225                 230                 235                 240

Gln Pro Ala Tyr Ser Leu Leu Ala Glu Gln Gln Glu Ala
                245                 250
```

<210> SEQ ID NO 36
<211> LENGTH: 36
<212> TYPE: DNA
<213> ORGANISM: Artificial
<220> FEATURE:
<223> OTHER INFORMATION: Primer Cytox-N-f-Bam

<400> SEQUENCE: 36
gtggatccgt tattcaagaa taccttacgt ttaatg                36

<210> SEQ ID NO 37
<211> LENGTH: 27
<212> TYPE: DNA
<213> ORGANISM: Artificial
<220> FEATURE:
<223> OTHER INFORMATION: Primer Cytox-r-999-Eco

<400> SEQUENCE: 37
aggaattcaa gcttcttgct gttcagc                         27

<210> SEQ ID NO 38
<211> LENGTH: 63
<212> TYPE: DNA
<213> ORGANISM: Artificial
<220> FEATURE:
<223> OTHER INFORMATION: pGEX-4T-3 multi cloning site
<220> FEATURE:
<221> NAME/KEY: CDS
<222> LOCATION: (1)..(63)
<223> OTHER INFORMATION:

<400> SEQUENCE: 38

```
ctg gtt ccg cgt gga tcc ccg aat tcc cgg gtc gac tcg agc ggc cgc    48
Leu Val Pro Arg Gly Ser Pro Asn Ser Arg Val Asp Ser Ser Gly Arg
1               5                   10                  15 atc gtg act gac tga                                                63
Ile Val Thr Asp
            20
```

<210> SEQ ID NO 39
<211> LENGTH: 20
<212> TYPE: PRT
<213> ORGANISM: Artificial
<220> FEATURE:
<223> OTHER INFORMATION: pGEX-4T-3 multi cloning site

<400> SEQUENCE: 39

Leu Val Pro Arg Gly Ser Pro Asn Ser Arg Val Asp Ser Ser Gly Arg
1               5                   10                  15

Ile Val Thr Asp
            20

<210> SEQ ID NO 40
<211> LENGTH: 36
<212> TYPE: DNA
<213> ORGANISM: Artificial
<220> FEATURE:
<223> OTHER INFORMATION: p-delta-GST-4T-3

<400> SEQUENCE: 40
caggaaacag tattcatggg atccccgaat tcccgg                                36

<210> SEQ ID NO 41
<211> LENGTH: 18
<212> TYPE: DNA
<213> ORGANISM: Artificial
<220> FEATURE:
<223> OTHER INFORMATION: Forward primer for one day mutagenesis

<400> SEQUENCE: 41
ggatccccga attcccgg                                                    18

<210> SEQ ID NO 42
<211> LENGTH: 18
<212> TYPE: DNA
<213> ORGANISM: Artificial
<220> FEATURE:
<223> OTHER INFORMATION: Reverse primer for one day mutagenesis

<400> SEQUENCE: 42
catgaatact gtttcctg                                                    18

<210> SEQ ID NO 43
<211> LENGTH: 15
<212> TYPE: DNA
<213> ORGANISM: Artificial
<220> FEATURE:
<223> OTHER INFORMATION: Region around the 5' end of MM29kD

<400> SEQUENCE: 43
atgggatccg ttatt                                                       15

<210> SEQ ID NO 44
<211> LENGTH: 21
<212> TYPE: DNA
<213> ORGANISM: Artificial
<220> FEATURE:
<223> OTHER INFORMATION: Primer 1Aa3-C1-f

<400> SEQUENCE: 44
ggatccgcgg tgaatgagct g                                                21

<210> SEQ ID NO 45
<211> LENGTH: 21
<212> TYPE: DNA
<213> ORGANISM: Artificial
<220> FEATURE:
<223> OTHER INFORMATION: Primer 1Aa3-C1-r

<400> SEQUENCE: 45
ctcgagaccc acatttactg t                                                21

<210> SEQ ID NO 46
<211> LENGTH: 480
<212> TYPE: DNA
<213> ORGANISM: Artificial
<220> FEATURE:
<223> OTHER INFORMATION: 1AaCter(622-777) coding DNA with attached
      restriction sites

<400> SEQUENCE: 46

```
ggatccgcgg tgaatgagct gtttacttct tccaatcaaa tcggggttaaa aacagatgtg    60 acggattatc atattgatca agtatccaat ttagttgagt gtttatcaga tgaattttgt   120
ctggatgaaa acaagaatt gtccgagaaa gtcaaacatg cgaagcgact tagtgatgag    180
cggaatttac ttcaagatcc aaacttcaga gggatcaata dacaactaga ccgtggctgg   240
agaggaagta cggatattac catccaagga ggcgatgacg tattcaaaga gaattacgtt   300
acgctattgg gtacctttga tgagtgctat ccaacgtatt tatatcaaaa aatagatgag   360
tcgaaattaa aagcctatac ccgttatcaa ttaagagggt atatcgaaga tagtcaagac   420
ttagaaatct atttaattcg ctacaatgca aaacatgaaa cagtaaatgt gggtctcgag   480
```

<210> SEQ ID NO 47
<211> LENGTH: 21
<212> TYPE: DNA
<213> ORGANISM: Artificial
<220> FEATURE:
<223> OTHER INFORMATION: Primer 1Ac1-C1-f

<400> SEQUENCE: 47

```
ggatccgcgg tgaatgcgct g                                               21
```

<210> SEQ ID NO 48
<211> LENGTH: 21
<212> TYPE: DNA
<213> ORGANISM: Artificial
<220> FEATURE:
<223> OTHER INFORMATION: Primer 1Ac1-C1-r

<400> SEQUENCE: 48

```
ctcgagtggc acatttactg t                                               21
```

<210> SEQ ID NO 49
<211> LENGTH: 480
<212> TYPE: DNA
<213> ORGANISM: Artificial
<220> FEATURE:
<223> OTHER INFORMATION: 1AcCter(624-779) coding DNA with attached
      restriction sites

<400> SEQUENCE: 49

```
ggatccgcgg tgaatgcgct gtttacgtct acaaaccaac tagggctaaa acaaatgta     60 acggattatc atattgatca agtgtccaat ttagttacgt atttatcgga tgaattttgt   120
ctggatgaaa agcgagaatt gtccgagaaa gtcaaacatg cgaagcgact cagtgatgaa   180
cgcaatttac tccaagattc aaatttcaaa gacattaata ggcaaccaga acgtgggtgg   240
ggcggaagta cagggattac catccaagga ggggatgacg tatttaaaga aaattacgtc   300
acactatcag gtacctttga tgagtgctat ccaacatatt tgtatcaaaa aatcgatgaa   360
tcaaaattaa aagcctttac ccgttatcaa ttaagagggt atatcgaaga tagtcaagac   420
ttagaaatct atttaattcg ctacaatgca aaacatgaaa cagtaaatgt gccactcgag   480
```

```
<210> SEQ ID NO 50
<211> LENGTH: 1176
<212> TYPE: PRT
<213> ORGANISM: Bacillus thuringiensis

<400> SEQUENCE: 50

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Pro Val Gln Ile
 65                  70                  75                  80

Glu Gln Leu Ile Asn Gln Arg Ile Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380
```

```
Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
            405                 410                 415

Gln Asp Asn Ser Val Pro Pro Arg Ala Gly Phe Ser His Arg Leu Ser
        420                 425                 430

His Val Thr Met Leu Ser Gln Ala Ala Gly Ala Val Tyr Thr Leu Arg
    435                 440                 445

Ala Pro Thr Phe Ser Trp Gln His Arg Ser Ala Glu Phe Asn Asn Ile
450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
            485                 490                 495

Asp Ile Leu Arg Arg Thr Ser Pro Gly Gln Ile Ser Thr Leu Arg Val
        500                 505                 510

Asn Ile Thr Ala Pro Leu Ser Gln Arg Tyr Arg Val Arg Ile Arg Tyr
    515                 520                 525

Ala Ser Thr Thr Asn Leu Gln Phe His Thr Ser Ile Asp Gly Arg Pro
530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
            565                 570                 575

Ser Asn Gly Ser Ser Val Phe Thr Leu Ser Ala His Val Phe Asn Ser
        580                 585                 590

Gly Asn Glu Val Tyr Ile Asp Arg Ile Glu Phe Val Pro Ala Glu Val
    595                 600                 605

Thr Phe Glu Ala Glu Tyr Asp Leu Glu Arg Ala Gln Lys Ala Val Asn
610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
            645                 650                 655

Glu Phe Cys Leu Asp Glu Lys Gln Glu Leu Ser Glu Lys Val Lys His
        660                 665                 670

Ala Lys Arg Leu Ser Asp Glu Arg Asn Leu Leu Gln Asp Pro Asn Phe
    675                 680                 685

Arg Gly Ile Asn Arg Gln Leu Asp Arg Gly Trp Arg Gly Ser Thr Asp
690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
            725                 730                 735

Ile Asp Glu Ser Lys Leu Lys Ala Tyr Thr Arg Tyr Gln Leu Arg Gly
        740                 745                 750

Tyr Ile Glu Asp Ser Gln Asp Leu Glu Ile Tyr Leu Ile Arg Tyr Asn
    755                 760                 765

Ala Lys His Glu Thr Val Asn Val Pro Gly Thr Gly Ser Leu Trp Pro
770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
```

```
                805                 810                 815
Gly Glu Lys Cys Ala His His Ser His His Phe Ser Leu Asp Ile Asp
        820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
        850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
                900                 905                 910

Asn Ser Gln Tyr Asp Gln Leu Gln Ala Asp Thr Asn Ile Ala Met Ile
                915                 920                 925

His Ala Ala Asp Lys Arg Val His Ser Ile Arg Glu Ala Tyr Leu Pro
                930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
                980                 985                 990

Gly His Val Asp Val Glu Glu Gln Asn Asn Gln Arg Ser Val Leu Val
                995                 1000                1005

Leu Pro Glu Trp Glu Ala Glu Val Ser Gln Glu Val Arg Val Cys
        1010                1015                1020

Pro Gly Arg Gly Tyr Ile Leu Arg Val Thr Ala Tyr Lys Glu Gly
        1025                1030                1035

Tyr Gly Glu Gly Cys Val Thr Ile His Glu Ile Glu Asn Asn Thr
        1040                1045                1050

Asp Glu Leu Lys Phe Ser Asn Cys Val Glu Glu Glu Ile Tyr Pro
        1055                1060                1065

Asn Asn Thr Val Thr Cys Asn Asp Tyr Thr Val Asn Gln Glu Glu
        1070                1075                1080

Tyr Gly Gly Ala Tyr Thr Ser Arg Asn Arg Gly Tyr Asn Glu Ala
        1085                1090                1095

Pro Ser Val Pro Ala Asp Tyr Ala Ser Val Tyr Glu Glu Lys Ser
        1100                1105                1110

Tyr Thr Asp Gly Arg Arg Glu Asn Pro Cys Glu Phe Asn Arg Gly
        1115                1120                1125

Tyr Arg Asp Tyr Thr Pro Leu Pro Val Gly Tyr Val Thr Lys Glu
        1130                1135                1140

Leu Glu Tyr Phe Pro Glu Thr Asp Lys Val Trp Ile Glu Ile Gly
        1145                1150                1155

Glu Thr Glu Gly Thr Phe Ile Val Asp Ser Val Glu Leu Leu Leu
        1160                1165                1170

Met Glu Glu
        1175

<210> SEQ ID NO 51
<211> LENGTH: 934
<212> TYPE: PRT
<213> ORGANISM: Bacillus thuringiensis
```

<400> SEQUENCE: 51

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Arg Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
```

-continued

```
                405                 410                 415
Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830
```

-continued

```
Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
        850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Arg Leu Gln Ala Asp Thr Asn Ile Ala Met Ile
        915                 920                 925

His Ala Ala Asp Lys Arg
    930

<210> SEQ ID NO 52
<211> LENGTH: 1176
<212> TYPE: PRT
<213> ORGANISM: Bacillus thuringiensis

<400> SEQUENCE: 52

Met Asp Asn Asn Pro Asn Ile Asn Glu Cys Ile Pro Tyr Asn Cys Leu
1               5                   10                  15

Ser Asn P

```
            260                 265                 270
Leu Glu Asn Phe Asp Gly Ser Phe Arg Gly Met Ala Gln Arg Ile Glu
            275                 280                 285

Gln Asn Ile Arg Gln Pro His Leu Met Asp Ile Leu Asn Ser Ile Thr
            290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
            340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
            370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Glu Phe Asn Asn Ile
            450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
            530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
            595                 600                 605

Thr Phe Glu Ala Glu Tyr Asp Leu Glu Arg Ala Gln Lys Ala Val Asn
            610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
            675                 680                 685
```

-continued

```
Arg Gly Ile Asn Arg Gln Leu Asp Arg Gly Trp Arg Gly Ser Thr Asp
    690                 695                 700
Ile Thr Ile Gln Gly Gly Asp Asp Val Phe Lys Glu Asn Tyr Val Thr
705                 710                 715                 720
Leu Leu Gly Thr Phe Asp Glu Cys Tyr Pro Thr Tyr Leu Tyr Gln Lys
                725                 730                 735
Ile Asp Glu Ser Lys Leu Lys Ala Tyr Thr Arg Tyr Gln Leu Arg Gly
            740                 745                 750
Tyr Ile Glu Asp Ser Gln Asp Leu Glu Ile Tyr Leu Ile Arg Tyr Asn
        755                 760                 765
Ala Lys His Glu Thr Val Asn Val Pro Gly Thr Gly Ser Leu Trp Pro
770                 775                 780
Leu Ser Ala Gln Ser Pro Ile Gly Lys Cys Gly Glu Pro Asn Arg Cys
785                 790                 795                 800
Ala Pro His Leu Glu Trp Asn Pro Asp Leu Asp Cys Ser Cys Arg Asp
                805                 810                 815
Gly Glu Lys Cys Ala His His Ser His Phe Ser Leu Asp Ile Asp
            820                 825                 830
Val Gly Cys Thr Asp Leu Asn Glu Asp Leu Gly Val Trp Val Ile Phe
        835                 840                 845
Lys Ile Lys Thr Gln Asp Gly His Ala Arg Leu Gly Asn Leu Glu Phe
850                 855                 860
Leu Glu Glu Lys Pro Leu Val Gly Glu Ala Leu Ala Arg Val Lys Arg
865                 870                 875                 880
Ala Glu Lys Lys Trp Arg Asp Lys Arg Glu Lys Leu Glu Trp Glu Thr
                885                 890                 895
Asn Ile Val Tyr Lys Glu Ala Lys Glu Ser Val Asp Ala Leu Phe Val
            900                 905                 910
Asn Ser Gln Tyr Asp Gln Leu Gln Ala Asp Thr Asn Ile Ala Met Ile
        915                 920                 925
His Ala Ala Asp Lys Arg Val His Ser Ile Arg Glu Ala Tyr Leu Pro
930                 935                 940
Glu Leu Ser Val Ile Pro Gly Val Asn Ala Ala Ile Phe Glu Glu Leu
945                 950                 955                 960
Glu Gly Arg Ile Phe Thr Ala Phe Ser Leu Tyr Asp Ala Arg Asn Val
                965                 970                 975
Ile Lys Asn Gly Asp Phe Asn Asn Gly Leu Ser Cys Trp Asn Val Lys
            980                 985                 990
Gly His Val Asp Val Glu Glu Gln Asn Asn Gln Arg Ser Val Leu Val
        995                 1000                1005
Val Pro Glu Trp Glu Ala Glu Val Ser Gln Glu Val Arg Val Cys
    1010                1015                1020
Pro Gly Arg Gly Tyr Ile Leu Arg Val Thr Ala Tyr Lys Glu Gly
    1025                1030                1035
Tyr Gly Glu Gly Cys Val Thr Ile His Glu Ile Glu Asn Asn Thr
    1040                1045                1050
Asp Glu Leu Lys Phe Ser Asn Cys Val Glu Glu Glu Ile Tyr Pro
    1055                1060                1065
Asn Asn Thr Val Thr Cys Asn Asp Tyr Thr Val Asn Gln Glu Glu
    1070                1075                1080
Tyr Gly Gly Ala Tyr Thr Ser Arg Asn Arg Gly Tyr Asn Glu Ala
    1085                1090                1095
```

```
Pro Ser Val Pro Ala Asp Tyr Ala Ser Val Tyr Glu Glu Lys Ser
    1100                1105                1110

Tyr Thr Asp Gly Arg Arg Glu Asn Pro Cys Glu Phe Asn Arg Gly
    1115                1120                1125

Tyr Arg Asp Tyr Thr Pro Leu Pro Val Gly Tyr Val Thr Lys Glu
    1130                1135                1140

Leu Glu Tyr Phe Pro Glu Thr Asp Lys Val Trp Ile Glu Ile Gly
    1145                1150                1155

Glu Thr Glu Gly Thr Phe Ile Val Asp Ser Val Glu Leu Leu Leu
    1160                1165                1170

Met Glu Glu
    1175

<210> SEQ ID NO 53
<211> LENGTH: 1176
<212> TYPE: PRT
<213> ORGANISM: Bacillus thuringiensis

<400> SEQUENCE: 53

Met Asp Asn Asn Pro Asn Ile Asn Glu Cys Ile Pro Tyr Asn Cys Leu
1                5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285
```

```
Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
                340                 345                 350

Thr Gly Leu Gly Ile Phe Arg Thr Leu Ser Ser Pro Leu Tyr Arg Arg
                355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
                435                 440                 445

Ala Pro Thr Phe Ser Trp Gln His Arg Ser Ala Glu Phe Asn Asn Ile
450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
                500                 505                 510

Asn Ile Thr Ala Pro Leu Ser Gln Arg Tyr Arg Val Arg Ile Arg Tyr
                515                 520                 525

Ala Ser Thr Thr Asn Leu Gln Phe His Thr Ser Ile Asp Gly Arg Pro
530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
                595                 600                 605

Thr Phe Glu Ala Glu Tyr Asp Leu Glu Arg Ala Gln Lys Ala Val Asn
610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
                675                 680                 685

Arg Gly Ile Asn Arg Gln Leu Asp Arg Gly Trp Arg Gly Ser Thr Asp
690                 695                 700
```

-continued

Ile Thr Ile Gln Gly Gly Asp Asp Val Phe Lys Glu Asn Tyr Val Thr
705                     710                     715                     720

Leu Leu Gly Thr Phe Asp Glu Cys Tyr Pro Thr Tyr Leu Tyr Gln Lys
              725                     730                     735

Ile Asp Glu Ser Lys Leu Lys Ala Tyr Thr Arg Tyr Gln Leu Arg Gly
              740                     745                     750

Tyr Ile Glu Asp Ser Gln Asp Leu Glu Ile Tyr Leu Ile Arg Tyr Asn
              755                     760                     765

Ala Lys His Glu Thr Val Asn Val Pro Gly Thr Gly Ser Leu Trp Pro
770                     775                     780

Leu Ser Ala Gln Ser Pro Ile Gly Lys Cys Gly Glu Pro Asn Arg Cys
785                     790                     795                     800

Ala Pro His Leu Glu Trp Asn Pro Asp Leu Asp Cys Ser Cys Arg Asp
              805                     810                     815

Gly Glu Lys Cys Ala His His Ser His His Phe Ser Leu Asp Ile Asp
              820                     825                     830

Val Gly Cys Thr Asp Leu Asn Glu Asp Leu Gly Val Trp Val Ile Phe
              835                     840                     845

Lys Ile Lys Thr Gln Asp Gly His Ala Arg Leu Gly Asn Leu Glu Phe
850                     855                     860

Leu Glu Glu Lys Pro Leu Val Gly Glu Ala Leu Ala Arg Val Lys Arg
865                     870                     875                     880

Ala Glu Lys Lys Trp Arg Asp Lys Arg Glu Lys Leu Glu Trp Glu Thr
              885                     890                     895

Asn Ile Val Tyr Lys Glu Ala Lys Glu Ser Val Asp Ala Leu Phe Val
              900                     905                     910

Asn Ser Gln Tyr Asp Gln Leu Gln Ala Asp Thr Asn Ile Ala Met Ile
              915                     920                     925

His Ala Ala Asp Lys Arg Val His Ser Ile Arg Glu Ala Tyr Leu Pro
930                     935                     940

Glu Leu Ser Val Ile Pro Gly Val Asn Ala Ala Ile Phe Glu Glu Leu
945                     950                     955                     960

Glu Gly Arg Ile Phe Thr Ala Phe Ser Leu Tyr Asp Ala Arg Asn Val
              965                     970                     975

Ile Lys Asn Gly Asp Phe Asn Asn Gly Leu Ser Cys Trp Asn Val Lys
              980                     985                     990

Gly His Val Asp Val Glu Glu Gln Asn Asn Gln Arg Ser Val Leu Val
              995                    1000                    1005

Val Pro Glu Trp Glu Ala Glu Val Ser Gln Glu Val Arg Val Cys
     1010                   1015                    1020

Pro Gly Arg Gly Tyr Ile Leu Arg Val Thr Ala Tyr Lys Glu Gly
     1025                   1030                    1035

Tyr Gly Glu Gly Cys Val Thr Ile His Glu Ile Glu Asn Asn Thr
     1040                   1045                    1050

Asp Glu Leu Lys Phe Ser Asn Cys Val Glu Glu Glu Ile Tyr Pro
     1055                   1060                    1065

Asn Asn Thr Val Thr Cys Asn Asp Tyr Thr Val Asn Gln Glu Glu
     1070                   1075                    1080

Tyr Gly Gly Ala Tyr Thr Ser Arg Asn Arg Gly Tyr Asn Glu Ala
     1085                   1090                    1095

Pro Ser Val Pro Ala Asp Tyr Ala Ser Val Tyr Glu Glu Lys Ser
     1100                   1105                    1110

Tyr Thr Asp Gly Arg Arg Glu Asn Pro Cys Glu Phe Asn Arg Gly

```
            1115                1120                1125

Tyr Arg Asp Tyr Thr Pro Leu Pro Val Gly Tyr Val Thr Lys Glu
            1130                1135                1140

Leu Glu Tyr Phe Pro Glu Thr Asp Lys Val Trp Ile Glu Ile Gly
            1145                1150                1155

Glu Thr Glu Gly Thr Phe Ile Val Asp Ser Val Glu Leu Leu Leu
            1160                1165                1170

Met Glu Glu
    1175

<210> SEQ ID NO 54
<211> LENGTH: 1176
<212> TYPE: PRT
<213> ORGANISM: Bacillus thuringiensis

<400> SEQUENCE: 54

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300
```

-continued

```
Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Phe Gly Asn Ala Gly Asn Ala Ala Pro Val Leu Val Ser Leu
        340                 345                 350

Thr Gly Leu Gly Ile Phe Arg Thr Leu Ser Ser Pro Leu Tyr Arg Arg
    355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
            405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
```

```
              725                 730                 735
Ile Asp Glu Ser Lys Leu Lys Ala Tyr Thr Arg Tyr Gln Leu Arg Gly
                740                 745                 750

Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
                820                 825                 830

Val Gly Cys Thr Asp Leu Asn Glu Asp Leu Gly Val Trp Val Ile Phe
                835                 840                 845

Lys Ile Lys Thr Gln Asp Gly His Ala Arg Leu Gly Asn Leu Glu Phe
850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
                900                 905                 910

Asn Ser Gln Tyr Asp Gln Leu Gln Ala Asp Thr Asn Ile Ala Met Ile
            915                 920                 925

His Ala Ala Asp Lys Arg Val His Ser Ile Arg Glu Ala Tyr Leu Pro
930                 935                 940

Glu Leu Ser Val Ile Pro Gly Val Asn Ala Ala Ile Phe Glu Glu Leu
945                 950                 955                 960

Glu Gly Arg Ile Ser Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
                980                 985                 990

Gly His Val Asp Val Glu Glu Gln Asn Asn Gln Arg Ser Val Leu Val
            995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Glu Ile Tyr Pro
    1055                1060                1065

Asn Asn Thr Val Thr Cys Asn Asp Tyr Thr Val Asn Gln Glu Glu
    1070                1075                1080

Tyr Gly Gly Ala Tyr Thr Ser Arg Asn Arg Gly Tyr Asn Glu Ala
    1085                1090                1095

Pro Ser Val Pro Ala Asp Tyr Ala Ser Val Tyr Glu Glu Lys Ser
    1100                1105                1110

Tyr Thr Asp Gly Arg Arg Glu Asn Pro Cys Glu Phe Asn Arg Gly
    1115                1120                1125

Tyr Arg Asp Tyr Thr Pro Leu Pro Val Gly Tyr Val Thr Lys Glu
    1130                1135                1140
```

```
Leu Glu Tyr Phe Pro Glu Thr Asp Lys Val Trp Ile Glu Ile Gly
    1145                 1150                1155

Glu Thr Glu Gly Thr Phe Ile Val Asp Ser Val Glu Leu Leu Leu
    1160                 1165                1170

Met Glu Glu
    1175

<210> SEQ ID NO 55
<211> LENGTH: 1176
<212> TYPE: PRT
<213> ORGANISM: Bacillus thuringiensis

<400> SEQUENCE: 55

Met Asp Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65              70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
```

```
                    325                 330                 335
Leu Phe Gly Asn Ala Gly Asn Ala Ala Pro Val Leu Val Ser Leu
                340                 345                 350
Thr Gly Leu Gly Ile Phe Arg Thr Leu Ser Ser Pro Leu Tyr Arg Arg
                355                 360                 365
Ile Ile Leu Gly Ser Gly Pro Asn Asn Gln Glu Leu Phe Val Leu Asp
            370                 375                 380
Gly Thr Glu Phe Ser Phe Ala Ser Leu Thr Thr Asn Leu Pro Ser Thr
385                 390                 395                 400
Ile Tyr Arg Gln Arg Gly Thr Val Asp Ser Leu Asp Val Ile Pro Pro
                405                 410                 415
Gln Asp Asn Ser Val Pro Pro Arg Ala Gly Phe Ser His Arg Leu Ser
                420                 425                 430
His Val Thr Met Leu Ser Gln Ala Ala Gly Ala Val Tyr Thr Leu Arg
                435                 440                 445
Ala Pro Thr Phe Ser Trp Gln His Arg Ser Ala Glu Phe Asn Asn Ile
            450                 455                 460
Ile Pro Ser Ser Gln Ile Thr Gln Ile Pro Leu Thr Lys Ser Thr Asn
465                 470                 475                 480
Leu Gly Ser Gly Thr Ser Val Val Lys Gly Pro Gly Phe Thr Gly Gly
                485                 490                 495
Asp Ile Leu Arg Arg Thr Ser Pro Gly Gln Ile Ser Thr Leu Arg Val
                500                 505                 510
Asn Ile Thr Ala Pro Leu Ser Gln Arg Tyr Arg Val Arg Ile Arg Tyr
                515                 520                 525
Ala Ser Thr Thr Asn Leu Gln Phe His Thr Ser Ile Asp Gly Arg Pro
                530                 535                 540
Ile Asn Gln Gly Asn Phe Ser Ala Thr Met Ser Ser Gly Ser Asn Leu
545                 550                 555                 560
Gln Ser Gly Ser Phe Arg Thr Val Gly Phe Thr Thr Pro Phe Asn Phe
                565                 570                 575
Ser Asn Gly Ser Ser Val Phe Thr Leu Ser Ala His Val Phe Asn Ser
                580                 585                 590
Gly Asn Glu Val Tyr Ile Asp Arg Ile Glu Phe Val Pro Ala Glu Val
                595                 600                 605
Thr Phe Glu Ala Glu Tyr Asp Leu Glu Arg Ala Gln Lys Ala Val Asn
                610                 615                 620
Glu Leu Phe Thr Ser Ser Asn Gln Ile Gly Leu Lys Thr Asp Val Thr
625                 630                 635                 640
Asp Tyr His Ile Asp Gln Val Ser Asn Leu Val Glu Cys Leu Ser Asp
                645                 650                 655
Glu Phe Cys Leu Asp Glu Lys Gln Glu Leu Ser Glu Lys Val Lys His
                660                 665                 670
Ala Lys Arg Leu Ser Asp Glu Arg Asn Leu Leu Gln Asp Pro Asn Phe
                675                 680                 685
Arg Gly Ile Asn Arg Gln Leu Asp Arg Gly Trp Arg Gly Ser Thr Asp
            690                 695                 700
Ile Thr Ile Gln Gly Gly Asp Asp Val Phe Lys Glu Asn Tyr Val Thr
705                 710                 715                 720
Leu Leu Gly Thr Phe Asp Glu Cys Tyr Pro Thr Tyr Leu Tyr Gln Lys
                725                 730                 735
Ile Asp Glu Ser Lys Leu Lys Ala Tyr Thr Arg Tyr Gln Leu Arg Gly
            740                 745                 750
```

```
Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
            805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
            850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
            915                 920                 925

His Ala Ala Asp Lys Arg Val His Ser Ile Arg Glu Ala Tyr Leu Pro
930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn Gln Arg Ser Val Leu Val
            995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Glu Ile Tyr Pro
    1055                1060                1065

Asn Asn Thr Val Thr Cys Asn Asp Tyr Thr Val Asn Gln Glu Glu
    1070                1075                1080

Tyr Gly Gly Ala Tyr Thr Ser Arg Asn Arg Gly Tyr Asn Glu Ala
    1085                1090                1095

Pro Ser Val Pro Ala Asp Tyr Ala Ser Val Tyr Glu Glu Lys Ser
    1100                1105                1110

Tyr Thr Asp Gly Arg Arg Glu Asn Pro Cys Glu Phe Asn Arg Gly
    1115                1120                1125

Tyr Arg Asp Tyr Thr Pro Leu Pro Val Gly Tyr Val Thr Lys Glu
    1130                1135                1140

Leu Glu Tyr Phe Pro Glu Thr Asp Lys Val Trp Ile Glu Ile Gly
    1145                1150                1155
```

Glu Thr Glu Gly Thr Phe Ile Val Asp Ser Val Glu Leu Leu Leu
1160                1165                1170

Met Glu Glu
    1175

<210> SEQ ID NO 56
<211> LENGTH: 1180
<212> TYPE: PRT
<213> ORGANISM: Bacillus thuringiensis

<400> SEQUENCE: 56

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Arg Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

```
Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
        370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
                435                 440                 445

Ala Pro Thr Phe Ser Trp Gln His Arg Ser Ala Glu Phe Asn Asn Ile
        450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
                500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
        530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
        610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
        690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
                740                 745                 750

Tyr Ile Glu Asp Ser Gln Asp Leu Glu Ile Tyr Leu Ile Arg Tyr Asn
        755                 760                 765
```

```
Ala Lys His Glu Thr Val Asn Val Pro Gly Thr Gly Ser Leu Trp Pro
770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
            805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
            885                 890                 895

Asn Ile Val Tyr Lys Glu Ala Lys Glu Ser Val Asp Ala Leu Phe Val
            900                 905                 910

Asn Ser Gln Tyr Asp Arg Leu Gln Ala Asp Thr Asn Ile Ala Met Ile
            915                 920                 925

His Ala Ala Asp Lys Arg Val His Ser Ile Arg Glu Ala Tyr Leu Pro
930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
            965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn His Arg Ser Val Leu Val
            995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Glu Val Tyr Pro
    1055                1060                1065

Asn Asn Thr Val Thr Cys Asn Asp Tyr Thr Ala Thr Gln Glu Glu
    1070                1075                1080

Tyr Glu Gly Thr Tyr Thr Ser Arg Asn Arg Gly Tyr Asp Gly Ala
    1085                1090                1095

Tyr Glu Ser Asn Ser Ser Val Pro Ala Asp Tyr Ala Ser Ala Tyr
    1100                1105                1110

Glu Glu Lys Ala Tyr Thr Asp Gly Arg Arg Asp Asn Pro Cys Glu
    1115                1120                1125

Ser Asn Arg Gly Tyr Gly Asp Tyr Thr Pro Leu Pro Ala Gly Tyr
    1130                1135                1140

Val Thr Lys Glu Leu Glu Tyr Phe Pro Glu Thr Asp Lys Val Trp
    1145                1150                1155

Ile Glu Ile Gly Glu Thr Glu Gly Thr Phe Ile Val Asp Ser Val
    1160                1165                1170

Glu Leu Leu Leu Met Glu Glu
```

1175          1180

<210> SEQ ID NO 57
<211> LENGTH: 1176
<212> TYPE: PRT
<213> ORGANISM: Bacillus thuringiensis

<400> SEQUENCE: 57

Met Asp Asn Asn Pro Asn Ile Asn Glu Cys Ile Pro Tyr Asn Cys Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Thr Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

```
Ile Ile Leu Gly Ser Gly Pro Asn Asn Gln Glu Leu Phe Val Leu Asp
    370             375             380
Gly Thr Glu Phe Ser Phe Ala Ser Leu Thr Thr Asn Leu Pro Ser Thr
385             390             395             400
Ile Tyr Arg Gln Arg Gly Thr Val Asp Ser Leu Asp Val Ile Pro Pro
            405             410             415
Gln Asp Asn Ser Val Pro Pro Arg Ala Gly Phe Ser His Arg Leu Gly
            420             425             430
His Val Thr Met Leu Ser Gln Ala Gly Ala Val Tyr Thr Leu Arg
            435             440             445
Ala Pro Thr Phe Ser Trp Gln His Arg Ser Ala Glu Phe Asn Asn Ile
450             455             460
Ile Pro Ser Ser Gln Ile Thr Gln Ile Pro Leu Thr Lys Ser Thr Asn
465             470             475             480
Leu Gly Ser Gly Thr Ser Val Val Lys Gly Pro Gly Phe Thr Gly Gly
            485             490             495
Asp Ile Leu Arg Arg Thr Ser Pro Gly Gln Ile Ser Thr Leu Arg Val
            500             505             510
Asn Ile Thr Ala Pro Leu Ser Gln Arg Tyr Arg Val Arg Ile Arg Tyr
            515             520             525
Ala Ser Thr Thr Asn Leu Gln Phe His Thr Ser Ile Asp Gly Arg Pro
            530             535             540
Ile Asn Gln Gly Asn Phe Ser Ala Thr Met Ser Ser Gly Ser Asn Leu
545             550             555             560
Gln Ser Gly Ser Phe Arg Thr Val Gly Phe Thr Thr Pro Phe Asn Phe
            565             570             575
Ser Asn Gly Ser Ser Val Phe Thr Leu Ser Ala His Val Phe Asn Ser
            580             585             590
Gly Asn Glu Val Tyr Ile Asp Arg Ile Glu Phe Val Pro Ala Glu Val
            595             600             605
Thr Phe Glu Ala Glu Tyr Asp Leu Glu Arg Ala Gln Lys Ala Val Asn
            610             615             620
Glu Leu Phe Thr Ser Ser Asn Gln Ile Gly Leu Lys Thr Asp Val Thr
625             630             635             640
Asp Tyr His Ile Asp Gln Val Ser Asn Leu Val Glu Cys Leu Ser Asp
            645             650             655
Glu Phe Cys Leu Asp Glu Lys Gln Glu Leu Ser Glu Lys Val Lys His
            660             665             670
Ala Lys Arg Leu Ser Asp Glu Arg Asn Leu Leu Gln Asp Pro Asn Phe
            675             680             685
Arg Gly Ile Asn Arg Gln Leu Asp Arg Gly Trp Arg Gly Ser Thr Asp
            690             695             700
Ile Thr Ile Gln Gly Gly Asp Asp Val Phe Lys Glu Asn Tyr Val Thr
705             710             715             720
Leu Leu Gly Thr Phe Asp Glu Cys Tyr Pro Thr Tyr Leu Tyr Gln Lys
            725             730             735
Ile Asp Glu Ser Lys Leu Lys Ala Tyr Thr Arg Tyr Gln Leu Arg Gly
            740             745             750
Tyr Ile Glu Asp Ser Gln Asp Leu Glu Ile Tyr Leu Ile Arg Tyr Asn
            755             760             765
Ala Lys His Glu Thr Val Asn Val Pro Gly Thr Gly Ser Leu Trp Pro
            770             775             780
Leu Ser Ala Gln Ser Pro Ile Gly Lys Cys Gly Glu Pro Asn Arg Cys
```

```
                785                 790                 795                 800
Ala Pro His Leu Glu Trp Asn Pro Asp Leu Asp Cys Ser Cys Arg Asp
                    805                 810                 815
Gly Glu Lys Cys Ala His His Ser His His Phe Ser Leu Asp Ile Asp
                    820                 825                 830
Val Gly Cys Thr Asp Leu Asn Glu Asp Leu Gly Val Trp Val Ile Phe
                    835                 840                 845
Lys Ile Lys Thr Gln Asp Gly His Ala Arg Leu Gly Asn Leu Glu Phe
                    850                 855                 860
Leu Glu Glu Lys Pro Leu Val Gly Glu Ala Leu Ala Arg Val Lys Ile
865                 870                 875                 880
Ala Glu Lys Lys Trp Arg Asp Lys Arg Glu Lys Leu Glu Trp Glu Thr
                    885                 890                 895
Asn Ile Val Tyr Lys Glu Ala Lys Glu Ser Val Asp Ala Leu Phe Val
                    900                 905                 910
Asn Ser Gln Tyr Asp Gln Leu Gln Ala Asp Thr Asn Ile Ala Met Ile
                    915                 920                 925
His Ala Ala Asp Lys Arg Val His Ser Ile Arg Glu Ala Tyr Leu Pro
            930                 935                 940
Glu Leu Ser Val Ile Pro Gly Val Asn Ala Ala Ile Phe Glu Glu Leu
945                 950                 955                 960
Glu Gly Arg Ile Phe Thr Ala Phe Ser Leu Tyr Asp Ala Arg Asn Val
                    965                 970                 975
Ile Lys Asn Gly Asp Phe Asn Asn Gly Leu Ser Cys Trp Asn Val Lys
                    980                 985                 990
Gly His Val Asp Val Glu Glu Gln Asn Asn Gln Arg Ser Val Leu Val
            995                 1000                1005
Val Pro Glu Trp Glu Ala Glu Val Ser Gln Glu Val Arg Val Cys
    1010                1015                1020
Pro Gly Arg Gly Tyr Ile Leu Arg Val Thr Ala Tyr Lys Glu Gly
    1025                1030                1035
Tyr Gly Glu Gly Cys Val Thr Ile His Glu Ile Glu Asn Asn Thr
    1040                1045                1050
Asp Glu Leu Lys Phe Ser Asn Cys Val Glu Glu Glu Ile Tyr Ser
    1055                1060                1065
Asn Asn Thr Val Thr Cys Asn Asp Tyr Thr Val Asn Gln Glu Glu
    1070                1075                1080
Tyr Gly Gly Ala Tyr Thr Ser Arg Asn Arg Gly Tyr Asn Glu Ala
    1085                1090                1095
Pro Ser Val Pro Ala Asp Tyr Ala Ser Val Tyr Glu Glu Lys Ser
    1100                1105                1110
Tyr Thr Asp Gly Arg Arg Glu Asn Pro Cys Glu Phe Asn Arg Gly
    1115                1120                1125
Tyr Arg Asp Tyr Thr Pro Leu Pro Val Gly Tyr Val Thr Lys Glu
    1130                1135                1140
Leu Glu Tyr Phe Pro Glu Thr Asp Lys Val Trp Ile Glu Ile Gly
    1145                1150                1155
Glu Thr Glu Gly Thr Phe Ile Val Asp Ser Val Glu Leu Leu Leu
    1160                1165                1170
Met Glu Glu
    1175

<210> SEQ ID NO 58
```

<211> LENGTH: 1176
<212> TYPE: PRT
<213> ORGANISM: Bacillus thuringiensis

<400> SEQUENCE: 58

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
```

```
            385                 390                 395                 400
Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
                435                 440                 445

Ala Pro Thr Phe Ser Trp Gln His Arg Ser Ala Glu Phe Asn Asn Ile
            450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
                500                 505                 510

Asn Ile Thr Ala Pro Leu Ser Gln Arg Tyr Arg Val Arg Ile Arg Tyr
                515                 520                 525

Ala Ser Thr Thr Asn Leu Gln Phe His Thr Ser Ile Asp Gly Arg Pro
            530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
                595                 600                 605

Thr Phe Glu Ala Glu Tyr Asp Leu Glu Arg Ala Gln Lys Ala Val Asn
            610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
            675                 680                 685

Arg Gly Ile Asn Arg Gln Leu Asp Arg Gly Trp Arg Gly Ser Thr Asp
690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
                755                 760                 765

Ala Lys His Glu Thr Val Asn Val Pro Gly Thr Gly Ser Leu Trp Pro
            770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815
```

```
Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
    850                 855                 860

Leu Glu Glu Lys Pro Leu Val Gly Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn Gln Arg Ser Val Leu Val
        995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Ile Tyr Pro
    1055                1060                1065

Asn Asn Thr Val Thr Cys Asn Asp Tyr Thr Val Asn Gln Glu Glu
    1070                1075                1080

Tyr Gly Gly Ala Tyr Thr Ser Arg Asn Arg Gly Tyr Asn Glu Ala
    1085                1090                1095

Pro Ser Val Pro Ala Asp Tyr Ala Ser Val Tyr Glu Glu Lys Ser
    1100                1105                1110

Tyr Thr Asp Gly Arg Arg Glu Asn Pro Cys Glu Phe Asn Arg Gly
    1115                1120                1125

Tyr Arg Asp Tyr Thr Pro Leu Pro Val Gly Tyr Val Thr Lys Glu
    1130                1135                1140

Leu Glu Tyr Phe Pro Glu Thr Asp Lys Val Trp Ile Glu Ile Gly
    1145                1150                1155

Glu Thr Glu Gly Thr Phe Ile Val Asp Ser Val Glu Leu Leu Leu
    1160                1165                1170

Met Glu Glu
    1175

<210> SEQ ID NO 59
<211> LENGTH: 1176
<212> TYPE: PRT
<213> ORGANISM: Bacillus thuringiensis
```

```
<400> SEQUENCE: 59

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415
```

```
Gln Asp Asn Ser Val Pro Pro Arg Ala Gly Phe Ser His Arg Leu Ser
            420             425             430

His Val Thr Met Leu Ser Gln Ala Ala Gly Ala Val Tyr Thr Leu Arg
            435             440             445

Ala Pro Thr Phe Ser Trp Gln His Arg Ser Ala Glu Phe Asn Asn Ile
    450             455             460

Ile Pro Ser Ser Gln Ile Thr Gln Ile Pro Leu Thr Lys Ser Thr Asn
465             470             475             480

Leu Gly Ser Gly Thr Ser Val Val Lys Gly Pro Gly Phe Thr Gly Gly
                485             490             495

Asp Ile Leu Arg Arg Thr Ser Pro Gly Gln Ile Ser Thr Leu Arg Val
            500             505             510

Asn Ile Thr Ala Pro Leu Ser Gln Arg Tyr Arg Val Arg Ile Arg Tyr
            515             520             525

Ala Ser Thr Thr Asn Leu Gln Phe His Thr Ser Ile Asp Gly Arg Pro
    530             535             540

Ile Asn Gln Gly Asn Phe Ser Ala Thr Met Ser Ser Gly Ser Asn Leu
545             550             555             560

Gln Ser Gly Ser Phe Arg Thr Val Gly Phe Thr Thr Pro Phe Asn Phe
                565             570             575

Ser Asn Gly Ser Ser Val Phe Thr Leu Ser Ala His Val Phe Asn Ser
            580             585             590

Gly Asn Glu Val Tyr Ile Asp Arg Ile Glu Phe Val Pro Ala Glu Val
            595             600             605

Thr Phe Glu Ala Glu Tyr Asp Leu Glu Arg Ala Gln Lys Ala Val Asn
    610             615             620

Glu Leu Phe Thr Ser Ser Asn Gln Ile Gly Leu Lys Thr Asp Val Thr
625             630             635             640

Asp Tyr His Ile Asp Gln Val Ser Asn Leu Val Glu Cys Leu Ser Asp
                645             650             655

Glu Phe Cys Leu Asp Glu Lys Gln Glu Leu Ser Glu Lys Val Lys His
            660             665             670

Ala Lys Arg Leu Ser Asp Glu Arg Asn Leu Leu Gln Asp Pro Asn Phe
            675             680             685

Arg Gly Ile Asn Arg Gln Leu Asp Arg Gly Trp Arg Gly Ser Thr Asp
    690             695             700

Ile Thr Ile Gln Gly Gly Asp Asp Val Phe Lys Glu Asn Tyr Val Thr
705             710             715             720

Leu Leu Gly Thr Phe Asp Glu Cys Tyr Pro Thr Tyr Leu Tyr Gln Lys
                725             730             735

Ile Asp Glu Ser Lys Leu Lys Ala Tyr Thr Arg Tyr Gln Leu Arg Gly
            740             745             750

Tyr Ile Glu Asp Ser Gln Asp Leu Glu Ile Tyr Leu Ile Arg Tyr Asn
    755             760             765

Ala Lys His Glu Thr Val Asn Val Pro Gly Thr Gly Ser Leu Trp Pro
    770             775             780

Leu Ser Ala Gln Ser Pro Ile Gly Lys Cys Gly Glu Pro Asn Arg Cys
785             790             795             800

Ala Pro His Leu Glu Trp Asn Pro Asp Leu Asp Cys Ser Cys Arg Asp
            805             810             815

Gly Glu Lys Cys Ala His His Ser His His Phe Ser Leu Asp Ile Asp
            820             825             830
```

-continued

```
Val Gly Cys Thr Asp Leu Asn Glu Asp Leu Gly Val Trp Val Ile Phe
        835                 840                 845
Lys Ile Lys Thr Gln Asp Gly His Ala Arg Leu Gly Asn Leu Glu Phe
    850                 855                 860
Leu Glu Glu Lys Pro Leu Val Gly Ala Leu Ala Arg Val Lys Arg
865                 870                 875                 880
Ala Glu Lys Lys Trp Arg Asp Lys Arg Glu Lys Leu Glu Trp Glu Thr
                885                 890                 895
Asn Ile Val Tyr Lys Glu Ala Lys Glu Ser Val Asp Ala Leu Phe Val
                900                 905                 910
Asn Ser Gln Tyr Asp Gln Leu Gln Ala Asp Thr Asn Ile Ala Met Ile
            915                 920                 925
His Ala Ala Asp Lys Arg Val His Ser Ile Arg Glu Ala Tyr Leu Pro
        930                 935                 940
Glu Leu Ser Val Ile Pro Gly Val Asn Ala Ala Ile Phe Glu Glu Leu
945                 950                 955                 960
Glu Gly Arg Ile Phe Thr Ala Phe Ser Leu Tyr Asp Ala Arg Asn Val
                965                 970                 975
Ile Lys Asn Gly Asp Phe Asn Asn Gly Leu Ser Cys Trp Asn Val Lys
            980                 985                 990
Gly His Val Asp Val Glu Glu Gln Asn Asn Gln Arg Ser Val Leu Val
        995                 1000                1005
Val Pro Glu Trp Glu Ala Glu Val Ser Gln Glu Val Arg Val Cys
    1010                1015                1020
Pro Gly Arg Gly Tyr Ile Leu Arg Val Thr Ala Tyr Lys Glu Gly
    1025                1030                1035
Tyr Gly Glu Gly Cys Val Thr Ile His Glu Ile Glu Asn Asn Thr
    1040                1045                1050
Asp Glu Leu Lys Phe Ser Asn Cys Val Glu Glu Ile Tyr Pro
    1055                1060                1065
Asn Asn Thr Val Thr Cys Asn Asp Tyr Thr Val Asn Gln Glu Glu
    1070                1075                1080
Tyr Gly Gly Ala Tyr Thr Ser Arg Asn Arg Gly Tyr Asn Glu Ala
    1085                1090                1095
Pro Ser Val Pro Ala Asp Tyr Ala Ser Val Tyr Glu Glu Lys Ser
    1100                1105                1110
Tyr Thr Asp Gly Arg Arg Glu Asn Pro Cys Glu Phe Asn Arg Gly
    1115                1120                1125
Tyr Arg Asp Tyr Thr Pro Leu Pro Val Gly Tyr Val Thr Lys Glu
    1130                1135                1140
Leu Glu Tyr Phe Pro Glu Thr Asp Lys Val Trp Ile Glu Ile Gly
    1145                1150                1155
Glu Thr Glu Gly Thr Phe Ile Val Asp Ser Val Glu Leu Leu Leu
    1160                1165                1170
Met Glu Glu
    1175
```

<210> SEQ ID NO 60
<211> LENGTH: 1180
<212> TYPE: PRT
<213> ORGANISM: Bacillus thuringiensis

<400> SEQUENCE: 60

```
Met Asp Asn Asn Pro Asn Ile Asn Glu Cys Ile Pro Tyr Asn Cys Leu
1               5                   10                  15
```

-continued

```
Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
             85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Arg Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430
```

-continued

His Val Thr Met Leu Ser Gln Ala Gly Ala Val Tyr Thr Leu Arg
        435                 440                 445

Ala Pro Thr Phe Ser Trp Gln His Arg Ser Ala Glu Phe Asn Asn Ile
450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Arg Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn His Arg Ser Val Leu Val
        995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Val Tyr Pro
    1055                1060                1065

Asn Asn Thr Val Thr Cys Asn Asp Tyr Thr Ala Thr Gln Glu Glu
    1070                1075                1080

Tyr Glu Gly Thr Tyr Thr Ser Arg Asn Arg Gly Tyr Asp Gly Ala
    1085                1090                1095

Tyr Glu Ser Asn Ser Ser Val Pro Ala Asp Tyr Ala Ser Ala Tyr
    1100                1105                1110

Glu Glu Lys Ala Tyr Thr Asp Gly Arg Arg Asp Asn Pro Cys Glu
    1115                1120                1125

Ser Asn Arg Gly Tyr Gly Asp Tyr Thr Pro Leu Pro Ala Gly Tyr
    1130                1135                1140

Val Thr Lys Glu Leu Glu Tyr Phe Pro Glu Thr Asp Lys Val Trp
    1145                1150                1155

Ile Glu Ile Gly Glu Thr Glu Gly Thr Phe Ile Val Asp Ser Val
    1160                1165                1170

Glu Leu Leu Leu Met Glu Glu
    1175                1180

<210> SEQ ID NO 61
<211> LENGTH: 1183
<212> TYPE: PRT
<213> ORGANISM: Bacillus thuringiensis

<400> SEQUENCE: 61

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

-continued

```
Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
             100                 105                 110

Ser Phe Arg Glu Trp Glu Ala Asp Pro Thr Asn Pro Ala Leu Arg Glu
         115                 120                 125

Glu Met Arg Ile Gln Phe Asn Asp Met Asn Ser Ala Leu Thr Thr Ala
     130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                 165                 170                 175

Val Phe Gly Gln Arg Trp Gly Phe Asp Ala Ala Thr Ile Asn Ser Arg
             180                 185                 190

Tyr Asn Asp Leu Thr Arg Leu Ile Gly Asn Tyr Thr Asp Tyr Ala Val
         195                 200                 205

Arg Trp Tyr Asn Thr Gly Leu Glu Arg Val Trp Gly Pro Asp Ser Arg
     210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                 245                 250                 255

Ile Arg Thr Val Ser Gln Leu Thr Arg Glu Ile Tyr Thr Asn Pro Val
             260                 265                 270

Leu Glu Asn Phe Asp Gly Ser Phe Arg Gly Met Ala Gln Arg Ile Glu
         275                 280                 285

Gln Asn Ile Arg Gln Pro His Leu Met Asp Ile Leu Asn Ser Ile Thr
     290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                 325                 330                 335

Leu Phe Gly Asn Ala Gly Asn Ala Ala Pro Pro Val Leu Val Ser Leu
             340                 345                 350

Thr Gly Leu Gly Ile Phe Arg Thr Leu Ser Ser Pro Leu Tyr Arg Arg
         355                 360                 365

Ile Ile Leu Gly Ser Gly Pro Asn Asn Gln Glu Leu Phe Val Leu Asp
     370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                 405                 410                 415

Gln Asp Asn Ser Val Pro Pro Arg Ala Gly Phe Ser His Arg Leu Ser
             420                 425                 430

His Val Thr Met Leu Ser Gln Ala Ala Gly Ala Val Tyr Thr Leu Arg
         435                 440                 445

Ala Pro Thr Phe Ser Trp Gln His Arg Ser Ala Glu Phe Asn Asn Ile
```

```
            450                 455                 460
Ile Pro Ser Ser Gln Val Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                    485                 490                 495

Asp Ile Leu Arg Arg Thr Ser Pro Gly Gln Ile Ser Thr Leu Arg Val
                500                 505                 510

Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
        530                 535                 540

Ile Asn Gln Gly Asn Phe Ser Ala Thr Met Cys Ser Gly Ser Asn Leu
545                 550                 555                 560

Gln Ser Gly Ser Phe Arg Thr Val Gly Phe Thr Thr Pro Phe Asn Phe
                565                 570                 575

Pro Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
            595                 600                 605

Thr Phe Glu Ala Glu Tyr Asp Leu Glu Arg Ala Gln Lys Ala Val Asn
        610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
            675                 680                 685

Arg Gly Ile Asn Arg Gln Leu Asp Arg Gly Trp Arg Gly Ser Thr Asp
        690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
                740                 745                 750

Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
        770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Glu Gly Lys Cys Ala His His Ser His His Phe Ser Leu Asp Ile Asp
                820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
        850                 855                 860

Leu Glu Glu Lys Pro Leu Val Gly Glu Ala Leu Ala Arg Val Lys Arg
865                 870                 875                 880
```

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
                900                 905                 910

Asn Ser Gln Tyr Asp Arg Leu Gln Ala Asp Thr Asn Ile Ala Met Ile
                915                 920                 925

His Ala Ala Asp Lys Arg Val His Ser Ile Arg Glu Ala Tyr Leu Pro
                930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
                980                 985                 990

Gly His Val Asp Val Glu Glu Gln Asn Asn His Arg Ser Val Leu Val
                995                 1000                1005

Val Pro Glu Trp Glu Ala Glu Val Ser Gln Glu Val Arg Val Cys
        1010                1015                1020

Pro Gly Arg Gly Tyr Ile Leu Arg Val Thr Ala Tyr Lys Glu Gly
        1025                1030                1035

Tyr Gly Glu Gly Cys Val Thr Ile His Glu Ile Glu Asn Asn Thr
        1040                1045                1050

Asp Glu Leu Lys Phe Ser Asn Cys Val Glu Glu Val Tyr Pro
        1055                1060                1065

Asn Asn Thr Val Thr Cys Asn Asp Tyr Thr Ala Thr Gln Glu Glu
        1070                1075                1080

Tyr Glu Gly Thr Tyr Thr Ser Arg Asn Arg Gly Tyr Asp Gly Ala
        1085                1090                1095

Tyr Glu Ser Asn Ser Ser Val Pro Ala Asp Tyr Ala Ser Ala Tyr
        1100                1105                1110

Glu Glu Lys Ala Tyr Thr Asp Gly Arg Arg Asp Asn Pro Cys Glu
        1115                1120                1125

Ser Asn Arg Gly Tyr Gly Asp Tyr Thr Pro Leu Pro Ala Gly Tyr
        1130                1135                1140

Val Thr Lys Glu Leu Glu Tyr Phe Pro Glu Thr Asp Lys Val Trp
        1145                1150                1155

Ile Glu Ile Gly Glu Thr Glu Gly Thr Phe Ile Val Asp Ser Val
        1160                1165                1170

Glu Leu Leu Leu Met Glu Glu Val Asp Ala
        1175                1180

<210> SEQ ID NO 62
<211> LENGTH: 1155
<212> TYPE: PRT
<213> ORGANISM: Bacillus thuringiensis

<400> SEQUENCE: 62

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile

```
                50                  55                  60
Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
                115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp His Ala Val
                195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
                370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480
```

-continued

```
Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845

Ala Leu Ala Arg Val Lys Arg Ala Glu Lys Lys Trp Arg Asp Lys Arg
    850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895
```

Asp Thr Asn Ile Ala Met Ile His Ala Ala Asp Lys Arg Val His Ser
                900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
        980                 985                 990

Gln Glu Val Arg Val Cys Pro Gly Arg Gly Tyr Ile Leu Arg Val Thr
    995                 1000                1005

Ala Tyr Lys Glu Gly Tyr Gly Glu Gly Cys Val Thr Ile His Glu
    1010                1015                1020

Ile Glu Asn Asn Thr Asp Glu Leu Lys Phe Ser Asn Cys Val Glu
    1025                1030                1035

Glu Glu Val Tyr Pro Asn Asn Thr Val Thr Cys Asn Asp Tyr Thr
    1040                1045                1050

Ala Thr Gln Glu Glu Tyr Glu Gly Thr Tyr Thr Ser Arg Asn Arg
    1055                1060                1065

Gly Tyr Asp Gly Ala Tyr Glu Ser Asn Ser Ser Val Pro Ala Asp
    1070                1075                1080

Tyr Ala Ser Ala Tyr Glu Glu Lys Ala Tyr Thr Asp Gly Arg Arg
    1085                1090                1095

Asp Asn Pro Cys Glu Ser Asn Arg Gly Tyr Gly Asp Tyr Thr Pro
    1100                1105                1110

Leu Pro Ala Gly Tyr Val Thr Lys Glu Leu Glu Tyr Phe Pro Glu
    1115                1120                1125

Thr Asp Lys Val Trp Ile Glu Ile Gly Glu Thr Glu Gly Thr Phe
    1130                1135                1140

Ile Val Asp Ser Val Glu Leu Leu Leu Met Glu Glu
    1145                1150                1155

<210> SEQ ID NO 63
<211> LENGTH: 1155
<212> TYPE: PRT
<213> ORGANISM: Bacillus thuringiensis

<400> SEQUENCE: 63

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

```
Ser Phe Arg Glu Trp Glu Ala Asp Pro Thr Asn Pro Ala Leu Arg Glu
    115                 120                 125
Glu Met Arg Ile Gln Phe Asn Asp Met Asn Ser Ala Leu Thr Thr Ala
130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
                180                 185                 190
Tyr Asn Asp Leu Thr Arg Leu Ile Gly Asn Tyr Thr Asp His Ala Val
                195                 200                 205
Arg Trp Tyr Asn Thr Gly Leu Glu Arg Val Trp Gly Pro Asp Ser Arg
    210                 215                 220
Asp Trp Ile Arg Tyr Asn Gln Phe Arg Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
                275                 280                 285
Gly Ser Ile Arg Ser Pro His Leu Met Asp Ile Leu Asn Ser Ile Thr
    290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
    355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
    435                 440                 445
Arg Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
                500                 505                 510
Val Asn Ile Thr Ala Pro Leu Ser Gln Arg Tyr Arg Val Arg Ile Arg
                515                 520                 525
```

```
Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
930                 935                 940

Leu Tyr Asp Ala Arg Asn Val Ile Lys Asn Gly Asp Phe Asn Asn Gly
```

```
                    945                 950                 955                 960
Leu Ser Cys Trp Asn Val Lys Gly His Val Asp Val Glu Glu Gln Asn
                        965                 970                 975
Asn His Arg Ser Val Leu Val Val Pro Glu Trp Glu Ala Glu Val Ser
                    980                 985                 990
Gln Glu Val Arg Val Cys Pro Gly Arg Gly Tyr Ile Leu Arg Val Thr
                995                1000                1005
Ala Tyr Lys Glu Gly Tyr Gly Glu Gly Cys Val Thr Ile His Glu
           1010                1015                1020
Ile Glu Asn Asn Thr Asp Glu Leu Lys Phe Ser Asn Cys Val Glu
      1025                1030                1035
Glu Glu Val Tyr Pro Asn Asn Thr Val Thr Cys Asn Asp Tyr Thr
      1040                1045                1050
Ala Thr Gln Glu Glu Tyr Glu Gly Thr Tyr Thr Ser Arg Asn Arg
      1055                1060                1065
Gly Tyr Asp Gly Ala Tyr Glu Ser Asn Ser Ser Val Pro Ala Asp
      1070                1075                1080
Tyr Ala Ser Ala Tyr Glu Glu Lys Ala Tyr Thr Asp Gly Arg Arg
      1085                1090                1095
Asp Asn Pro Cys Glu Ser Asn Arg Gly Tyr Gly Asp Tyr Thr Pro
      1100                1105                1110
Leu Pro Ala Gly Tyr Val Thr Lys Glu Leu Glu Tyr Phe Pro Glu
      1115                1120                1125
Thr Asp Lys Val Trp Ile Glu Ile Gly Glu Thr Glu Gly Thr Phe
      1130                1135                1140
Ile Val Asp Ser Val Glu Leu Leu Leu Met Glu Glu
      1145                1150                1155

<210> SEQ ID NO 64
<211> LENGTH: 1155
<212> TYPE: PRT
<213> ORGANISM: Bacillus thuringiensis

<400> SEQUENCE: 64

Met Asp Asn Asn Pro Asn Ile Asn Glu Cys Ile Pro Tyr Asn Cys Leu
1               5                  10                  15
Ser Asn Pro Glu Val Glu Val Leu Gly Gly Glu Arg Ile Glu Thr Gly
            20                  25                  30
Tyr Thr Pro Ile Asp Ile Ser Leu Ser Leu Thr Gln Phe Leu Leu Ser
        35                  40                  45
Glu Phe Val Pro Gly Ala Gly Phe Val Leu Gly Leu Val Asp Ile Ile
    50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
            100                 105                 110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
```

-continued

```
Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Ala Leu Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
```

-continued

```
                580                 585                 590
Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
            690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
            725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
            770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
            885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
            930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
            965                 970                 975

Asn Gln Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
            995                 1000                1005
```

```
Ala Tyr Lys Glu Gly Tyr Gly Glu Gly Cys Val Thr Ile His Glu
    1010            1015                1020

Ile Glu Asn Asn Thr Asp Glu Leu Lys Phe Ser Asn Phe Val Glu
    1025            1030                1035

Glu Glu Val Tyr Pro Asn Asn Thr Val Thr Cys Asn Asp Tyr Thr
    1040            1045                1050

Ala Thr Gln Glu Glu Tyr Gly Thr Tyr Thr Ser Arg Asn Arg
    1055            1060                1065

Gly Tyr Asp Gly Ala Tyr Glu Ser Asn Ser Ser Val Pro Ala Asp
    1070            1075                1080

Tyr Ala Ser Ala Tyr Glu Glu Lys Ala Tyr Thr Asp Gly Arg Arg
    1085            1090                1095

Asp Asn Pro Cys Glu Ser Asn Arg Gly Tyr Gly Asp Tyr Thr Pro
    1100            1105                1110

Leu Pro Ala Gly Tyr Val Thr Lys Glu Leu Glu Tyr Phe Pro Glu
    1115            1120                1125

Thr Asp Lys Val Trp Ile Glu Ile Gly Glu Thr Glu Gly Thr Phe
    1130            1135                1140

Ile Val Asp Ser Val Glu Leu Leu Leu Met Glu Glu
    1145            1150                1155

<210> SEQ ID NO 65
<211> LENGTH: 1155
<212> TYPE: PRT
<213> ORGANISM: Bacillus thuringiensis

<400> SEQUENCE: 65

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
```

-continued

```
            210                 215                 220
Asp Trp Ile Arg Tyr Asn Gln Phe Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
                275                 280                 285
Gly Ser Ile Arg Ser Pro His Leu Met Asp Ile Leu Asn Ser Ile Thr
            290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
            370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
                500                 505                 510
Val Asn Ile Thr Ala Pro Leu Ser Gln Arg Tyr Arg Val Arg Ile Arg
            515                 520                 525
Tyr Ala Ser Thr Thr Asn Leu Gln Phe His Thr Ser Ile Asp Gly Arg
            530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
                580                 585                 590
Ser Gly Asn Glu Val Tyr Ile Asp Arg Ile Glu Phe Val Pro Ala Glu
            595                 600                 605
Val Thr Phe Glu Ala Glu Tyr Asp Leu Glu Arg Ala Gln Lys Ala Val
            610                 615                 620
Asn Glu Leu Phe Thr Ser Ser Asn Gln Ile Gly Leu Lys Thr Asp Val
625                 630                 635                 640
```

```
Thr Asp Tyr His Ile Asp Gln Val Ser Asn Leu Val Glu Cys Leu Ser
            645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
            690                 695                 700

Asp Ile Thr Ile Gln Gly Gly Asp Val Phe Lys Glu Asn Tyr Val
705                 710                 715                 720

Thr Leu Leu Gly Thr Phe Asp Glu Cys Tyr Pro Thr Tyr Leu Tyr Gln
            725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
            770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
            850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
            885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
            930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
            965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
            995                 1000                1005

Ala Tyr Lys Glu Gly Tyr Gly Glu Gly Cys Val Thr Ile His Glu
            1010                1015                1020

Ile Glu Asn Asn Thr Asp Glu Leu Lys Phe Ser Asn Cys Val Glu
            1025                1030                1035

Glu Glu Val Tyr Pro Asn Asn Thr Val Thr Cys Asn Asp Tyr Thr
            1040                1045                1050
```

```
Ala Thr Gln Glu Glu Tyr Glu Gly Thr Tyr Thr Ser Arg Asn Arg
    1055                1060                1065

Gly Tyr Asp Gly Ala Tyr Glu Ser Asn Ser Ser Val Pro Ala Asp
    1070                1075                1080

Tyr Ala Ser Ala Tyr Glu Lys Ala Tyr Thr Asp Gly Arg Arg
    1085                1090                1095

Asp Asn Pro Cys Glu Ser Asn Arg Gly Tyr Gly Asp Tyr Thr Pro
    1100                1105                1110

Leu Pro Ala Gly Tyr Val Thr Lys Glu Leu Glu Tyr Phe Pro Glu
    1115                1120                1125

Thr Asp Lys Val Trp Ile Glu Ile Gly Glu Thr Glu Gly Thr Phe
    1130                1135                1140

Ile Val Asp Ser Val Glu Leu Leu Leu Met Glu Glu
    1145                1150                1155
```

<210> SEQ ID NO 66
<211> LENGTH: 1156
<212> TYPE: PRT
<213> ORGANISM: Bacillus thuringiensis

<400> SEQUENCE: 66

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270
```

```
Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685
```

```
Phe Arg Gly Ile Asn Arg Gln Leu Asp Arg Gly Trp Arg Gly Ser Thr
    690             695                 700

Asp Ile Thr Ile Gln Gly Gly Asp Val Phe Lys Glu Asn Tyr Val
705             710                 715                 720

Thr Leu Leu Gly Thr Phe Asp Glu Cys Tyr Pro Thr Tyr Leu Tyr Gln
                725             730                 735

Lys Ile Asp Glu Ser Lys Leu Lys Ala Tyr Thr Arg Tyr Gln Leu Arg
            740             745                 750

Gly Tyr Ile Glu Asp Ser Gln Asp Leu Glu Ile Tyr Leu Ile Arg Tyr
        755             760                 765

Asn Ala Lys His Glu Thr Val Asn Val Pro Gly Thr Gly Ser Leu Trp
770             775                 780

Pro Leu Ser Ala Pro Ser Pro Ile Gly Lys Cys Ala His His Ser His
785             790                 795                 800

His Phe Ser Leu Asp Ile Asp Val Gly Cys Thr Asp Leu Asn Glu Asp
                805             810                 815

Leu Gly Val Trp Val Ile Phe Lys Ile Lys Thr Gln Asp Gly His Glu
            820             825                 830

Arg Leu Gly Asn Leu Glu Phe Leu Glu Gly Arg Ala Pro Leu Val Gly
        835             840                 845

Glu Ala Leu Ala Arg Val Lys Arg Ala Glu Lys Lys Trp Arg Asp Lys
850             855                 860

Arg Glu Lys Leu Glu Trp Glu Thr Asn Ile Val Tyr Lys Glu Ala Lys
865             870                 875                 880

Glu Ser Val Asp Ala Leu Phe Val Asn Ser Gln Tyr Asp Arg Leu Gln
                885             890                 895

Ala Asp Thr Asn Ile Ala Met Ile His Ala Ala Asp Lys Arg Val His
            900             905                 910

Ser Ile Arg Glu Ala Tyr Leu Pro Glu Leu Ser Val Ile Pro Gly Val
        915             920                 925

Asn Ala Ala Ile Phe Glu Glu Leu Glu Gly Arg Ile Phe Thr Ala Phe
930             935                 940

Ser Leu Tyr Asp Ala Arg Asn Val Ile Lys Asn Gly Asp Phe Asn Asn
945             950                 955                 960

Gly Leu Ser Cys Trp Asn Val Lys Gly His Val Asp Val Glu Glu Gln
                965             970                 975

Asn Asn His Arg Ser Val Leu Val Val Pro Glu Trp Glu Ala Glu Val
            980             985                 990

Ser Gln Glu Val Arg Val Cys Pro Gly Arg Gly Tyr Ile Leu Arg Val
        995             1000                1005

Thr Ala Tyr Lys Glu Gly Tyr Gly Glu Gly Cys Val Thr Ile His
    1010            1015                1020

Glu Ile Glu Asn Asn Thr Asp Glu Leu Lys Phe Ser Asn Cys Val
    1025            1030                1035

Glu Glu Glu Val Tyr Pro Asn Asn Thr Val Thr Cys Asn Asp Tyr
    1040            1045                1050

Thr Ala Thr Gln Glu Glu Tyr Glu Gly Thr Tyr Thr Ser Arg Asn
    1055            1060                1065

Arg Gly Tyr Asp Gly Ala Tyr Glu Ser Asn Ser Ser Val Pro Ala
    1070            1075                1080

Asp Tyr Ala Ser Ala Tyr Glu Glu Lys Ala Tyr Thr Asp Gly Arg
    1085            1090                1095

Arg Asp Asn Pro Cys Glu Ser Asn Arg Gly Tyr Gly Asp Tyr Thr
```

```
                1100                1105                1110
Pro Leu Pro Ala Gly Tyr Val Thr Lys Glu Leu Glu Tyr Phe Pro
    1115                1120                1125

Glu Thr Asp Lys Val Trp Ile Glu Ile Gly Glu Thr Glu Gly Thr
    1130                1135                1140

Phe Ile Val Asp Ser Val Glu Leu Leu Leu Met Glu Glu
    1145                1150                1155

<210> SEQ ID NO 67
<211> LENGTH: 1155
<212> TYPE: PRT
<213> ORGANISM: Bacillus thuringiensis

<400> SEQUENCE: 67

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320
```

```
Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
        340                 345                 350

Gln Leu Gly Gln Gly Val Tyr Arg Thr Leu Ser Ser Thr Leu Tyr Arg
    355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
```

```
                740             745             750
Gly Tyr Ile Glu Asp Ser Gln Asp Leu Glu Ile Tyr Leu Ile Arg Tyr
            755             760             765
Asn Ala Lys His Glu Thr Val Asn Val Pro Gly Thr Gly Ser Leu Trp
            770             775             780
Pro Leu Ser Ala Pro Ser Pro Ile Gly Lys Cys Ala His His Ser His
785             790             795             800
His Phe Ser Leu Asp Ile Asp Val Gly Cys Thr Asp Leu Asn Glu Asp
            805             810             815
Leu Gly Val Trp Val Ile Phe Lys Ile Lys Thr Gln Asp Gly His Ala
            820             825             830
Arg Leu Gly Asn Leu Glu Phe Leu Glu Glu Lys Pro Leu Val Gly Glu
            835             840             845
Ala Leu Ala Arg Val Lys Arg Ala Glu Lys Lys Trp Arg Asp Lys Arg
            850             855             860
Glu Lys Leu Glu Trp Glu Thr Asn Ile Val Tyr Lys Glu Ala Lys Glu
865             870             875             880
Ser Val Asp Ala Leu Phe Val Asn Ser Gln Tyr Asp Arg Leu Gln Ala
            885             890             895
Asp Thr Asn Ile Ala Met Ile His Ala Ala Asp Lys Arg Val His Ser
            900             905             910
Ile Arg Glu Ala Tyr Leu Pro Glu Leu Ser Val Ile Pro Gly Val Asn
            915             920             925
Ala Ala Ile Phe Glu Glu Leu Glu Gly Arg Ile Phe Thr Ala Phe Ser
            930             935             940
Leu Tyr Asp Ala Arg Asn Val Ile Lys Asn Gly Asp Phe Asn Asn Gly
945             950             955             960
Leu Ser Cys Trp Asn Val Lys Gly His Val Asp Val Glu Glu Gln Asn
            965             970             975
Asn His Arg Ser Val Leu Val Val Pro Glu Trp Glu Ala Glu Val Ser
            980             985             990
Gln Glu Val Arg Val Cys Pro Gly Arg Gly Tyr Ile Leu Arg Val Thr
            995             1000            1005
Ala Tyr Lys Glu Gly Tyr Gly Glu Gly Cys Val Thr Ile His Glu
            1010            1015            1020
Ile Glu Asn Asn Thr Asp Glu Leu Lys Phe Ser Asn Cys Val Glu
            1025            1030            1035
Glu Glu Val Tyr Pro Asn Asn Thr Val Thr Cys Asn Asp Tyr Thr
            1040            1045            1050
Ala Thr Gln Glu Glu Tyr Glu Gly Thr Tyr Thr Ser Arg Asn Arg
            1055            1060            1065
Gly Tyr Asp Gly Ala Tyr Glu Ser Asn Ser Ser Val Pro Ala Asp
            1070            1075            1080
Tyr Ala Ser Ala Tyr Glu Glu Lys Ala Tyr Thr Asp Gly Arg Arg
            1085            1090            1095
Asp Asn Pro Cys Glu Ser Asn Arg Gly Tyr Gly Asp Tyr Thr Pro
            1100            1105            1110
Leu Pro Ala Gly Tyr Val Thr Lys Glu Leu Glu Tyr Phe Pro Glu
            1115            1120            1125
Thr Asp Lys Val Trp Ile Glu Ile Gly Glu Thr Glu Gly Thr Phe
            1130            1135            1140
Ile Val Asp Ser Val Glu Leu Leu Leu Met Glu Glu
            1145            1150            1155
```

```
<210> SEQ ID NO 68
<211> LENGTH: 1155
<212> TYPE: PRT
<213> ORGANISM: Bacillus thuringiensis

<400> SEQUENCE: 68
```

| | | | | | | | | | | | | | | |
|---|---|---|---|---|---|---|---|---|---|---|---|---|---|---|
| Met | Asp | Asn | Asn | Pro | Asn | Ile | Asn | Glu | Cys | Ile | Pro | Tyr | Asn | Cys | Leu |
| 1 | | | | 5 | | | | | 10 | | | | | 15 | |
| Ser | Asn | Pro | Glu | Val | Glu | Val | Leu | Gly | Gly | Glu | Arg | Ile | Glu | Thr | Gly |
| | | | 20 | | | | | 25 | | | | | 30 | | |
| Tyr | Thr | Pro | Ile | Asp | Ile | Ser | Leu | Ser | Leu | Thr | Gln | Phe | Leu | Leu | Ser |
| | | | 35 | | | | | 40 | | | | | 45 | | |
| Glu | Phe | Val | Pro | Gly | Ala | Gly | Phe | Val | Leu | Gly | Leu | Val | Asp | Ile | Ile |
| | 50 | | | | | 55 | | | | | 60 | | | | |
| Trp | Gly | Ile | Phe | Gly | Pro | Ser | Gln | Trp | Asp | Ala | Phe | Leu | Val | Gln | Ile |
| 65 | | | | | 70 | | | | | 75 | | | | | 80 |
| Glu | Gln | Leu | Ile | Asn | Gln | Arg | Ile | Glu | Glu | Phe | Ala | Arg | Asn | Gln | Ala |
| | | | | 85 | | | | | 90 | | | | | 95 | |
| Ile | Ser | Arg | Leu | Glu | Gly | Leu | Ser | Asn | Leu | Tyr | Gln | Ile | Tyr | Ala | Glu |
| | | | 100 | | | | | 105 | | | | | 110 | | |
| Ser | Phe | Arg | Glu | Trp | Glu | Ala | Asp | Pro | Thr | Asn | Pro | Ala | Leu | Arg | Glu |
| | | | 115 | | | | | 120 | | | | | 125 | | |
| Glu | Met | Arg | Ile | Gln | Phe | Asn | Asp | Met | Asn | Ser | Ala | Leu | Thr | Thr | Ala |
| | 130 | | | | | 135 | | | | | 140 | | | | |
| Ile | Pro | Leu | Phe | Ala | Val | Gln | Asn | Tyr | Gln | Val | Pro | Leu | Leu | Ser | Val |
| 145 | | | | | 150 | | | | | 155 | | | | | 160 |
| Tyr | Val | Gln | Ala | Ala | Asn | Leu | His | Leu | Ser | Val | Leu | Arg | Asp | Val | Ser |
| | | | | 165 | | | | | 170 | | | | | 175 | |
| Val | Phe | Gly | Gln | Arg | Trp | Gly | Phe | Asp | Ala | Ala | Thr | Ile | Asn | Ser | Arg |
| | | | 180 | | | | | 185 | | | | | 190 | | |
| Tyr | Asn | Asp | Leu | Thr | Arg | Leu | Ile | Gly | Asn | Tyr | Thr | Asp | His | Ala | Val |
| | | | 195 | | | | | 200 | | | | | 205 | | |
| Arg | Trp | Tyr | Asn | Thr | Gly | Leu | Glu | Arg | Val | Trp | Gly | Pro | Asp | Ser | Arg |
| | 210 | | | | | 215 | | | | | 220 | | | | |
| Asp | Trp | Ile | Arg | Tyr | Asn | Gln | Phe | Arg | Arg | Glu | Leu | Thr | Leu | Thr | Val |
| 225 | | | | | 230 | | | | | 235 | | | | | 240 |
| Leu | Asp | Ile | Val | Ser | Leu | Phe | Pro | Asn | Tyr | Asp | Ser | Arg | Thr | Tyr | Pro |
| | | | | 245 | | | | | 250 | | | | | 255 | |
| Ile | Arg | Thr | Val | Ser | Gln | Leu | Thr | Arg | Glu | Ile | Tyr | Thr | Asn | Pro | Val |
| | | | 260 | | | | | 265 | | | | | 270 | | |
| Leu | Glu | Asn | Phe | Asp | Gly | Ser | Phe | Arg | Gly | Ser | Ala | Gln | Gly | Ile | Glu |
| | | | 275 | | | | | 280 | | | | | 285 | | |
| Gly | Ser | Ile | Arg | Ser | Pro | His | Leu | Met | Asp | Ile | Leu | Asn | Ser | Ile | Thr |
| | 290 | | | | | 295 | | | | | 300 | | | | |
| Ile | Tyr | Thr | Asp | Ala | His | Arg | Gly | Glu | Tyr | Tyr | Trp | Ser | Gly | His | Gln |
| 305 | | | | | 310 | | | | | 315 | | | | | 320 |
| Ile | Met | Ala | Ser | Pro | Val | Gly | Phe | Ser | Gly | Pro | Glu | Phe | Thr | Phe | Pro |
| | | | | 325 | | | | | 330 | | | | | 335 | |
| Leu | Tyr | Gly | Thr | Met | Gly | Asn | Ala | Ala | Pro | Gln | Gln | Arg | Ile | Val | Ala |
| | | | 340 | | | | | 345 | | | | | 350 | | |
| Gln | Leu | Gly | Gln | Gly | Val | Tyr | Arg | Thr | Leu | Ser | Ser | Thr | Leu | Tyr | Arg |
| | | | 355 | | | | | 360 | | | | | 365 | | |
| Arg | Pro | Phe | Asn | Ile | Gly | Ile | Asn | Asn | Gln | Gln | Leu | Ser | Val | Leu | Asp |

```
            370                 375                 380
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
                515                 520                 525

Tyr Ala Ser Thr Thr Asn Leu Gln Phe His Thr Ser Ile Asp Gly Arg
                530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
                595                 600                 605

Val Thr Phe Glu Ala Glu Tyr Asp Leu Glu Arg Ala Gln Lys Ala Val
                610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
                675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
                740                 745                 750

Gly Tyr Ile Glu Asp Ser Gln Asp Leu Glu Ile Tyr Leu Ile Arg Tyr
                755                 760                 765

Asn Ala Lys His Glu Thr Val Asn Val Pro Gly Thr Gly Ser Leu Trp
                770                 775                 780

Pro Leu Ser Ala Pro Ser Pro Ile Gly Lys Cys Ala His His Ser His
785                 790                 795                 800
```

```
His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
            850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
            885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
            965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
            995                 1000                1005

Ala Tyr Lys Glu Gly Tyr Gly Glu Gly Cys Val Thr Ile His Glu
    1010                1015                1020

Ile Glu Asn Asn Thr Asp Glu Leu Lys Phe Ser Asn Cys Val Glu
    1025                1030                1035

Glu Glu Val Tyr Pro Asn Asn Thr Val Thr Cys Asn Asp Tyr Thr
    1040                1045                1050

Ala Thr Gln Glu Glu Tyr Gly Thr Tyr Thr Ser Arg Asn Arg
    1055                1060                1065

Gly Tyr Asp Gly Ala Tyr Glu Ser Asn Ser Ser Val Pro Ala Asp
    1070                1075                1080

Tyr Ala Ser Ala Tyr Glu Glu Lys Ala Tyr Thr Asp Gly Arg Arg
    1085                1090                1095

Asp Asn Pro Cys Glu Ser Asn Arg Gly Tyr Gly Asp Tyr Thr Pro
    1100                1105                1110

Leu Pro Ala Gly Tyr Val Thr Lys Glu Leu Glu Tyr Phe Pro Glu
    1115                1120                1125

Thr Asp Lys Val Trp Ile Glu Ile Gly Glu Thr Glu Gly Thr Phe
    1130                1135                1140

Ile Val Asp Ser Val Glu Leu Leu Leu Met Glu Glu
    1145                1150                1155

<210> SEQ ID NO 69
<211> LENGTH: 1155
<212> TYPE: PRT
<213> ORGANISM: Bacillus thuringiensis

<400> SEQUENCE: 69

Met Asp Asn Asn Pro Asn Ile Asn Glu Cys Ile Pro Tyr Asn Cys Leu
```

```
1               5                   10                  15
Ser Asn Pro Glu Val Glu Val Leu Gly Gly Glu Arg Ile Glu Thr Gly
            20                  25                  30
Tyr Thr Pro Ile Asp Ile Ser Leu Ser Leu Thr Gln Phe Leu Leu Ser
            35                  40                  45
Glu Phe Val Pro Gly Ala Gly Phe Val Leu Gly Leu Val Asp Ile Ile
50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
                100                 105                 110
Ser Phe Arg Glu Trp Glu Ala Asp Pro Thr Asn Pro Ala Leu Arg Glu
            115                 120                 125
Glu Met Arg Ile Gln Phe Asn Asp Met Asn Ser Ala Leu Thr Thr Ala
            130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp His Ala Val
            195                 200                 205
Arg Trp Tyr Asn Thr Gly Leu Glu Arg Val Trp Gly Pro Asp Ser Arg
210                 215                 220
Asp Trp Ile Arg Tyr Asn Gln Phe Arg Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
            275                 280                 285
Gly Ser Ile Arg Ser Pro His Leu Met Asp Ile Leu Asn Ser Ile Thr
            290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
            370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
```

```
Val Ser Met Phe Arg Ser Gly Phe Ser Asn Ser Ser Val Ser Ile Ile
    435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845
```

```
Ala Leu Ala Arg Val Lys Arg Ala Glu Lys Lys Trp Arg Asp Lys Arg
        850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005

Ala Tyr Lys Glu Gly Tyr Gly Glu Gly Cys Val Thr Ile His Glu
        1010                1015                1020

Ile Glu Asn Asn Thr Asp Glu Leu Lys Phe Ser Asn Cys Val Glu
        1025                1030                1035

Glu Glu Val Tyr Pro Asn Asn Thr Val Thr Cys Asn Asp Tyr Thr
        1040                1045                1050

Ala Thr Gln Glu Glu Tyr Gly Thr Tyr Thr Ser Arg Asn Arg
        1055                1060                1065

Gly Tyr Asp Gly Ala Tyr Glu Ser Asn Ser Ser Val Pro Ala Asp
        1070                1075                1080

Tyr Ala Ser Ala Tyr Glu Glu Lys Ala Tyr Thr Asp Gly Arg Arg
        1085                1090                1095

Asp Asn Pro Cys Glu Ser Asn Arg Gly Tyr Gly Asp Tyr Thr Pro
        1100                1105                1110

Leu Pro Ala Gly Tyr Val Thr Lys Glu Leu Glu Tyr Phe Pro Glu
        1115                1120                1125

Thr Asp Lys Val Trp Ile Glu Ile Gly Glu Thr Glu Gly Thr Phe
        1130                1135                1140

Ile Val Asp Ser Val Glu Leu Leu Leu Met Glu Glu
        1145                1150                1155

<210> SEQ ID NO 70
<211> LENGTH: 1155
<212> TYPE: PRT
<213> ORGANISM: Bacillus thuringiensis

<400> SEQUENCE: 70

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
50                  55                  60
```

```
Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Arg Val Pro Leu Leu Ser Val
145                 150                 155                 160

Tyr Val Gln Ala Val Asn Leu His Leu Ser Val Leu Arg Asp Val Leu
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Pro Ser Ser Gln Ile Thr Gln Ile Pro Leu Thr Lys Ser Thr
465                 470                 475                 480
```

```
Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
            610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
            770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Val Phe Val Asn Ser Gln Tyr Asp Arg Leu Gln Ala
                885                 890                 895

Asp Thr Asn Ile Ala Met Ile His Ala Ala Asp Lys Arg Val His Ser
```

```
                    900             905                 910
Ile Arg Glu Ala Tyr Leu Pro Glu Leu Ser Val Ile Pro Gly Val Asn
            915                 920                 925
Ala Ala Ile Phe Glu Glu Leu Glu Gly Arg Ile Phe Thr Ala Phe Ser
        930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
            980                 985                 990
Gln Glu Val Arg Val Cys Pro Gly Arg Gly Tyr Ile Leu Arg Val Thr
        995                 1000                1005
Ala Tyr Lys Glu Glu Tyr Gly Glu Gly Cys Val Thr Ile His Glu
    1010                1015                1020
Ile Glu Asn Asn Thr Ala Glu Leu Lys Phe Ser Asn Cys Val Glu
    1025                1030                1035
Glu Glu Val Tyr Pro Asn Asn Thr Val Thr Cys Asn Asp Tyr Thr
    1040                1045                1050
Ala Thr Gln Glu Glu Tyr Glu Gly Thr Tyr Thr Ser Arg Asn Arg
    1055                1060                1065
Gly Tyr Asp Gly Ala Tyr Glu Ser Asn Ser Ser Val Pro Ala Asp
    1070                1075                1080
Tyr Ala Ser Ala Tyr Glu Glu Lys Ala Tyr Thr Asp Gly Arg Arg
    1085                1090                1095
Asp Asn Pro Cys Glu Ser Asn Arg Gly Tyr Gly Asp Tyr Thr Pro
    1100                1105                1110
Leu Pro Ala Gly Tyr Val Thr Arg Glu Leu Glu Tyr Phe Pro Glu
    1115                1120                1125
Thr Asp Lys Val Trp Ile Glu Ile Gly Glu Thr Glu Gly Thr Phe
    1130                1135                1140
Ile Val Asp Ser Val Glu Leu Leu Leu Met Glu Glu
    1145                1150                1155

<210> SEQ ID NO 71
<211> LENGTH: 1156
<212> TYPE: PRT
<213> ORGANISM: Bacillus thuringiensis

<400> SEQUENCE: 71

Met Asp Asn Asn Pro Asn Ile Asn Glu Cys Ile Pro Tyr Asn Cys Leu
1               5                   10                  15
Ser Asn Pro Glu Val Glu Val Leu Gly Gly Glu Arg Ile Glu Thr Gly
            20                  25                  30
Tyr Thr Pro Ile Asp Ile Ser Leu Ser Leu Thr Gln Phe Leu Leu Ser
        35                  40                  45
Glu Phe Val Pro Gly Ala Gly Phe Val Leu Gly Leu Val Asp Ile Ile
    50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
            100                 105                 110
```

-continued

```
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Pro Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp His Ala Val
        195                 200                 205
Arg Trp Tyr Asn Thr Gly Leu Glu Arg Val Trp Gly Pro Asp Ser Arg
    210                 215                 220
Asp Trp Ile Arg Tyr Asn Gln Phe Arg Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Ser Ala Gln Gly Ile Glu
        275                 280                 285
Gly Ser Ile Arg Ser Pro His Leu Met Asp Ile Leu Asn Ser Ile Thr
    290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Gly Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
```

```
                        530                 535                 540
Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Gly Ala His His Ser
785                 790                 795                 800

His His Phe Ser Leu Asp Ile Asp Val Gly Cys Thr Asp Leu Asn Glu
                805                 810                 815

Asp Leu Gly Val Trp Val Ile Phe Lys Ile Lys Thr Gln Asp Gly His
            820                 825                 830

Ala Arg Leu Gly Asn Leu Glu Phe Leu Glu Glu Lys Pro Leu Val Gly
        835                 840                 845

Glu Ala Leu Ala Arg Val Lys Arg Ala Glu Lys Lys Trp Arg Gly Lys
    850                 855                 860

Arg Glu Lys Leu Glu Trp Glu Thr Asn Ile Val Tyr Lys Glu Ala Lys
865                 870                 875                 880

Glu Ser Val Asp Ala Leu Phe Val Asn Ser Gln Tyr Asp Arg Leu Gln
                885                 890                 895

Ala Asp Thr Asn Ile Ala Met Ile His Ala Ala Asp Lys Arg Val His
            900                 905                 910

Ser Ile Arg Glu Ala Tyr Leu Pro Glu Leu Ser Val Ile Pro Gly Val
        915                 920                 925

Asn Ala Ala Ile Phe Glu Glu Leu Glu Gly Arg Ile Phe Thr Ala Phe
    930                 935                 940

Ser Leu Tyr Asp Ala Arg Asn Val Ile Lys Asn Gly Asp Phe Asn Asn
945                 950                 955                 960
```

Gly Leu Ser Cys Trp Asn Val Lys Gly His Val Asp Val Glu Glu Gln
            965                 970                 975

Asn Asn His Arg Ser Val Leu Val Val Pro Glu Trp Glu Ala Glu Val
            980                 985                 990

Ser Gln Glu Val Arg Val Cys Pro Gly Arg Gly Tyr Ile Leu Arg Val
            995                 1000                1005

Thr Ala Tyr Lys Glu Gly Tyr Gly Glu Gly Cys Val Thr Ile His
        1010                1015                1020

Glu Ile Glu Asn Asn Thr Asp Glu Leu Lys Phe Ser Asn Cys Val
        1025                1030                1035

Glu Glu Glu Val Tyr Pro Asn Asn Thr Val Thr Cys Asn Asp Tyr
        1040                1045                1050

Thr Ala Thr Gln Glu Glu Tyr Glu Gly Thr Tyr Thr Ser Arg Asn
        1055                1060                1065

Arg Gly Tyr Asp Gly Ala Tyr Glu Ser Asn Ser Ser Val Pro Ala
        1070                1075                1080

Asp Tyr Ala Ser Ala Tyr Glu Glu Lys Ala Tyr Thr Asp Gly Arg
        1085                1090                1095

Arg Asp Asn Pro Cys Glu Ser Asn Arg Gly Tyr Gly Asp Tyr Thr
        1100                1105                1110

Pro Leu Pro Ala Gly Tyr Val Thr Lys Glu Leu Glu Tyr Phe Pro
        1115                1120                1125

Glu Thr Asp Lys Val Trp Ile Glu Ile Gly Glu Thr Glu Gly Thr
        1130                1135                1140

Phe Ile Val Asp Ser Val Glu Leu Leu Leu Met Glu Glu
        1145                1150                1155

<210> SEQ ID NO 72
<211> LENGTH: 1155
<212> TYPE: PRT
<213> ORGANISM: Bacillus thuringiensis

<400> SEQUENCE: 72

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser

```
                165                 170                 175
Val Phe Gly Gln Arg Trp Gly Phe Asp Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Pro Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Gly Ser Ile Arg Ser Pro His Leu Met Asp Ile Leu Asn Ser Ile Thr
            290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590
```

```
Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
        610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
        690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
        770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845

Ala Leu Ala Arg Val Lys Arg Ala Glu Lys Lys Trp Arg Asp Lys Arg
        850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
        930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005
```

```
Ala Tyr Lys Glu Gly Tyr Gly Glu Gly Cys Val Thr Ile His Glu
    1010            1015            1020

Ile Glu Asn Asn Thr Asp Glu Leu Lys Phe Ser Asn Cys Val Glu
    1025            1030            1035

Glu Glu Val Tyr Pro Asn Asn Thr Val Thr Cys Asn Asp Tyr Thr
    1040            1045            1050

Ala Thr Gln Glu Glu Tyr Glu Gly Thr Tyr Thr Ser Arg Asn Arg
    1055            1060            1065

Gly Tyr Asp Gly Ala Tyr Glu Ser Asn Ser Ser Val Pro Ala Asp
    1070            1075            1080

Tyr Ala Ser Ala Tyr Glu Lys Ala Tyr Thr Asp Gly Arg Arg
    1085            1090            1095

Asp Asn Pro Cys Glu Ser Asn Arg Gly Tyr Gly Asp Tyr Thr Pro
    1100            1105            1110

Leu Pro Ala Gly Tyr Val Thr Lys Glu Leu Glu Tyr Phe Pro Glu
    1115            1120            1125

Thr Asp Lys Val Trp Ile Glu Ile Gly Glu Thr Glu Gly Thr Phe
    1130            1135            1140

Ile Val Asp Ser Val Glu Leu Leu Leu Met Glu Glu
    1145            1150            1155

<210> SEQ ID NO 73
<211> LENGTH: 1156
<212> TYPE: PRT
<213> ORGANISM: Bacillus thuringiensis

<400> SEQUENCE: 73

Met Asp Asn Asn Pro Asn Ile Asn Glu Cys Ile Pro Tyr Asn Cys Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Arg Val
            195                 200                 205

Arg Trp Tyr Asn Thr Gly Leu Glu Arg Val Trp Gly Pro Asp Ser Arg
        210                 215                 220
```

-continued

```
Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
        260                 265                 270

Leu Glu Asn Phe Asp Gly Ser Phe Arg Gly Ser Ala Gln Gly Ile Glu
    275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Gly Pro Asp
370                 375                 380

Gly Gly Arg Ile Cys Leu Trp Asn Leu Leu Lys Phe Gly Gln Pro Pro
385                 390                 395                 400

Tyr Thr Glu Lys Ala Glu Pro Val Asp Ser Pro Asp Glu Ile Pro Pro
                405                 410                 415

Gln Asn Asn Asn Val Pro Pro Arg Gln Gly Phe Ser His Arg Cys Leu
            420                 425                 430

Ala Tyr Val Ser Met Phe Tyr Ser Gly Phe Ser Asn Ser Ser Val Ser
        435                 440                 445

Val Ile Arg Ala Pro Asn Asp Ser Ser Trp Thr Tyr Cys Ser Ala Glu
450                 455                 460

Phe Gly Asp Val Ile Pro Ser Ser Gln Ile Thr Gln Ile Pro Leu Thr
465                 470                 475                 480

Lys Leu Gln Ser Trp Leu Trp Asn Ser Val Val Lys Gly Leu Gly Phe
                485                 490                 495

Thr Gly Gly Asp Ile Leu Glu Glu Leu Thr Gly Gln Ile Ser Thr Leu
            500                 505                 510

Arg Val Asn Ile Thr Ala Pro Leu Ser Gln Arg Tyr Arg Val Arg Ile
        515                 520                 525

Arg Tyr Ala Ser Thr Thr Asn Leu Gln Phe His Thr Ser Ile Asp Gly
530                 535                 540

Arg Pro Ile Asn Gln Gly Asn Phe Ser Ala Thr Met Ser Ser Gly Ser
545                 550                 555                 560

Asn Leu Gln Ser Gly Ser Phe Arg Thr Val Gly Phe Thr Thr Pro Phe
                565                 570                 575

Asn Phe Ser Asn Gly Ser Ser Val Phe Thr Leu Ser Ala His Val Phe
            580                 585                 590

Asn Ser Gly Asn Glu Val Tyr Ile Asp Arg Ile Glu Phe Val Pro Ala
        595                 600                 605

Glu Val Thr Phe Glu Ala Glu Tyr Asp Leu Glu Arg Ala Gln Lys Ala
610                 615                 620

Val Asn Glu Leu Phe Thr Ser Ser Asn Gln Ile Gly Leu Lys Thr Asp
625                 630                 635                 640
```

-continued

Val Thr Asp Tyr His Ile Asp Gln Val Ser Asn Leu Val Glu Cys Leu
              645                 650                 655

Ser Asp Glu Phe Cys Leu Asp Glu Lys Lys Glu Leu Ser Glu Lys Val
            660                 665                 670

Lys His Ala Lys Arg Leu Ser Asp Glu Arg Asn Leu Leu Gln Asp Pro
        675                 680                 685

Asn Phe Arg Gly Ile Asn Arg Gln Leu Asp Arg Gly Trp Arg Gly Asn
690                 695                 700

Thr Asp Ile Thr Ile Gln Gly Gly His Asp Val Phe Lys Glu Asn Tyr
705                 710                 715                 720

Val Thr Leu Leu Gly Thr Phe Asp Glu Cys Tyr Pro Thr Tyr Leu Tyr
                725                 730                 735

Gln Lys Ile Asp Glu Ser Lys Leu Lys Ala Tyr Thr Arg Tyr Gln Leu
            740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
770                 775                 780

Trp Pro Leu Ser Ala Pro Ser Pro Ile Gly Lys Cys Ala His His Ser
785                 790                 795                 800

His His Phe Ser Leu Asp Ile Asp Val Gly Cys Thr Asp Leu Asn Glu
                805                 810                 815

Asp Leu Gly Val Trp Val Ile Phe Lys Ile Lys Thr Gln Asp Gly His
            820                 825                 830

Ala Arg Leu Gly Asn Leu Glu Phe Leu Glu Glu Lys Pro Leu Val Gly
        835                 840                 845

Glu Ala Leu Ala Arg Val Lys Arg Ala Glu Lys Lys Trp Arg Asp Lys
850                 855                 860

Arg Glu Lys Leu Glu Trp Glu Thr Asn Ile Val Tyr Lys Glu Ala Lys
865                 870                 875                 880

Glu Ser Val Asp Ala Leu Phe Val Asn Ser Gln Tyr Asp Arg Leu Gln
                885                 890                 895

Ala Asp Thr Asn Ile Ala Met Ile His Ala Ala Asp Lys Arg Val His
            900                 905                 910

Ser Ile Arg Glu Ala Tyr Leu Pro Glu Leu Ser Val Ile Pro Gly Val
        915                 920                 925

Asn Ala Ala Ile Phe Glu Glu Leu Glu Gly Arg Ile Phe Thr Ala Phe
930                 935                 940

Ser Leu Tyr Asp Ala Arg Asn Val Ile Lys Asn Gly Asp Phe Asn Asn
945                 950                 955                 960

Gly Leu Ser Cys Trp Asn Val Lys Gly His Val Asp Val Glu Glu Gln
                965                 970                 975

Asn Asn His Arg Ser Val Leu Val Pro Glu Trp Glu Ala Glu Val
            980                 985                 990

Ser Gln Glu Val Arg Val Cys Pro Gly Arg Gly Tyr Ile Leu Arg Val
        995                 1000                1005

Thr Ala Tyr Lys Glu Gly Tyr Gly Glu Gly Cys Val Thr Ile His
    1010                1015                1020

Glu Ile Glu Asn Asn Thr Asp Glu Leu Lys Phe Ser Asn Cys Val
    1025                1030                1035

Glu Glu Glu Val Tyr Pro Asn Asn Thr Val Thr Cys Asn Asp Tyr
    1040                1045                1050

Thr Ala Thr Gln Glu Glu Tyr Glu Gly Thr Tyr Thr Ser Arg Asn

-continued

```
            1055                1060                1065

Arg Gly Tyr Asp Gly Ala Tyr Glu Ser Asn Ser Ser Val Pro Ala
        1070                1075                1080

Asp Tyr Ala Ser Ala Tyr Glu Glu Lys Ala Tyr Thr Asp Gly Arg
    1085                1090                1095

Arg Asp Asn Pro Cys Glu Ser Asn Arg Gly Tyr Gly Asp Tyr Thr
1100                1105                1110

Pro Leu Pro Ala Gly Tyr Val Thr Lys Glu Leu Glu Tyr Phe Pro
        1115                1120                1125

Glu Thr Asp Lys Val Trp Ile Glu Ile Gly Glu Thr Glu Gly Thr
    1130                1135                1140

Phe Ile Val Asp Ser Val Glu Leu Leu Leu Met Glu Glu
1145                1150                1155

<210> SEQ ID NO 74
<211> LENGTH: 1178
<212> TYPE: PRT
<213> ORGANISM: Bacillus thuringiensis

<400> SEQUENCE: 74

Met Asp Asn Asn Pro Asn Ile Asn

```
Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
```

```
            690                 695                 700
Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
                740                 745                 750

Arg Gly Tyr Ile Glu Asp Ser Gln Asp Leu Glu Ile Tyr Leu Ile Arg
                755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
                820                 825                 830

Ile Asp Val Gly Cys Thr Asp Leu Asn Glu Asp Leu Gly Val Trp Val
                835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
                900                 905                 910

Phe Val Asn Ser Gln Tyr Asp Gln Leu Gln Ala Asp Thr Asn Ile Ala
                915                 920                 925

Met Ile His Ala Ala Asp Lys Arg Val His Ser Ile Arg Glu Ala Tyr
930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
                980                 985                 990

Val Lys Gly His Val Asp Val Glu Glu Gln Asn Asn Gln Arg Ser Val
                995                 1000                1005

Leu Val Val Pro Glu Trp Glu Ala Glu Val Ser Gln Glu Val Arg
           1010                1015                1020

Val Cys Pro Gly Arg Gly Tyr Ile Leu Arg Val Thr Ala Tyr Lys
           1025                1030                1035

Glu Gly Tyr Gly Glu Gly Cys Val Thr Ile His Glu Ile Glu Asn
           1040                1045                1050

Asn Thr Asp Glu Leu Lys Phe Ser Asn Cys Val Glu Glu Glu Ile
           1055                1060                1065

Tyr Pro Asn Asn Thr Val Thr Cys Asn Asp Tyr Thr Val Asn Gln
           1070                1075                1080

Glu Glu Tyr Gly Gly Ala Tyr Thr Ser Arg Asn Arg Gly Tyr Asn
           1085                1090                1095

Glu Ala Pro Ser Val Pro Ala Asp Tyr Ala Ser Val Tyr Glu Glu
           1100                1105                1110
```

```
Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 75
<211> LENGTH: 1178
<212> TYPE: PRT
<213> ORGANISM: Bacillus thuringiensis

<400> SEQUENCE: 75

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
```

```
                290                 295                 300
Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
                595                 600                 605

Thr Ala Thr Leu Glu Ala Glu Tyr Asn Leu Glu Arg Ala Gln Lys Ala
610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
                660                 665                 670

Lys His Ala Lys Arg Leu Ser Asp Glu Arg Asn Leu Leu Gln Asp Ser
                675                 680                 685

Asn Phe Lys Asp Ile Asn Arg Gln Pro Glu Arg Gly Trp Gly Gly Ser
                690                 695                 700

Thr Gly Ile Thr Ile Gln Gly Gly Asp Asp Val Phe Lys Glu Asn Tyr
705                 710                 715                 720
```

-continued

```
Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
            820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
            995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

Asn Thr Asp Glu Leu Lys Phe Ser Asn Cys Val Glu Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125
```

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
1145                1150                1155

Ile Gly Glu Thr Glu Gly Thr Phe Ile Val Asp Ser Val Glu Leu
1160                1165                1170

Leu Leu Met Glu Glu
1175

<210> SEQ ID NO 76
<211> LENGTH: 1178
<212> TYPE: PRT
<213> ORGANISM: Bacillus thuringiensis

<400> SEQUENCE: 76

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

-continued

```
Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
    690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735
```

```
Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
        770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
        820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
        850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
        900                 905                 910

Phe Val Asn Ser Gln Tyr Asp Gln Leu Gln Ala Asp Thr Asn Ile Ala
        915                 920                 925

Met Ile His Ala Ala Asp Lys Arg Val His Ser Ile Arg Glu Ala Tyr
        930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
        995                 1000                1005

Leu Val Val Pro Glu Trp Glu Ala Glu Val Ser Gln Glu Val Arg
        1010                1015                1020

Val Cys Pro Gly Arg Gly Tyr Ile Leu Arg Val Thr Ala Tyr Lys
        1025                1030                1035

Glu Gly Tyr Gly Glu Gly Cys Val Thr Ile His Glu Ile Glu Asn
        1040                1045                1050

Asn Thr Asp Glu Leu Lys Phe Ser Asn Cys Val Glu Glu Glu Ile
        1055                1060                1065

Tyr Pro Asn Asn Thr Val Thr Cys Asn Asp Tyr Thr Val Asn Gln
        1070                1075                1080

Glu Glu Tyr Gly Gly Ala Tyr Thr Ser Arg Asn Arg Gly Tyr Asn
        1085                1090                1095

Glu Ala Pro Ser Val Pro Ala Asp Tyr Ala Ser Val Tyr Glu Glu
        1100                1105                1110

Lys Ser Tyr Thr Asp Gly Arg Arg Glu Asn Pro Cys Glu Phe Asn
        1115                1120                1125

Arg Gly Tyr Arg Asp Tyr Thr Pro Leu Pro Val Gly Tyr Val Thr
        1130                1135                1140

Lys Glu Leu Glu Tyr Phe Pro Glu Thr Asp Lys Val Trp Ile Glu
```

```
                           1145                1150                1155
Ile Gly Glu Thr Glu Gly Thr Phe Ile Val Asp Ser Val Glu Leu
                     1160                1165                1170

Leu Leu Met Glu Glu
            1175

<210> SEQ ID NO 77
<211> LENGTH: 1178
<212> TYPE: PRT
<213> ORGANISM: Bacillus thuringiensis

<400> SEQUENCE: 77

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335
```

```
Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
            610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
        690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
```

```
              755                 760                 765
Tyr Asn Ala Lys His Glu Thr Val Asn Val Pro Gly Thr Gly Ser Leu
    770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
                820                 825                 830

Ile Asp Val Gly Cys Thr Asp Leu Asn Glu Asp Leu Gly Val Trp Val
                835                 840                 845

Ile Phe Lys Ile Lys Thr Gln Asp Gly His Ala Arg Leu Gly Asn Leu
    850                 855                 860

Glu Phe Leu Glu Glu Lys Pro Leu Val Gly Ala Leu Ala Arg Val
865                 870                 875                 880

Lys Arg Ala Glu Lys Lys Trp Arg Asp Lys Arg Glu Lys Leu Glu Trp
                    885                 890                 895

Glu Thr Asn Ile Val Tyr Lys Glu Ala Lys Glu Ser Val Asp Ala Leu
                900                 905                 910

Phe Val Asn Ser Gln Tyr Asp Gln Leu Gln Ala Asp Thr Asn Ile Ala
    915                 920                 925

Met Ile His Ala Ala Asp Lys Arg Val His Ser Ile Arg Glu Ala Tyr
930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
                980                 985                 990

Val Lys Gly His Val Asp Val Glu Glu Gln Asn Asn Gln Arg Ser Val
                995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

Asn Thr Asp Glu Leu Lys Phe Ser Asn Cys Val Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170
```

-continued

Leu Leu Met Glu Glu
1175

<210> SEQ ID NO 78
<211> LENGTH: 1178
<212> TYPE: PRT
<213> ORGANISM: Bacillus thuringiensis

<400> SEQUENCE: 78

Met Asp Asn Asn Pro Asn Ile Asn Glu Cys Ile Pro Tyr Asn Cys Leu
1 5 10 15

Ser Asn Pro Glu Val Glu Val Leu Gly Gly Glu Arg Ile Glu Thr Gly
20 25 30

Tyr Thr Pro Ile Asp Ile Ser Leu Ser Leu Thr Gln Phe Leu Leu Ser
35 40 45

Glu Phe Val Pro Gly Ala Gly Phe Val Leu Gly Leu Val Asp Ile Ile
50 55 60

Trp Gly Ile Phe Gly Pro Ser Gln Trp Asp Ala Phe Leu Val Gln Ile
65 70 75 80

Glu Gln Leu Ile Asn Gln Arg Ile Glu Glu Phe Ala Arg Asn Gln Ala
85 90 95

Ile Ser Arg Leu Glu Gly Leu Ser Asn Leu Tyr Gln Ile Tyr Ala Glu
100 105 110

Ser Phe Arg Glu Trp Glu Ala Asp Pro Thr Asn Pro Ala Leu Arg Glu
115 120 125

Glu Met Arg Ile Gln Phe Asn Asp Met Asn Ser Ala Leu Thr Thr Ala
130 135 140

Ile Pro Leu Phe Ala Val Gln Asn Tyr Gln Val Pro Leu Leu Ser Val
145 150 155 160

Tyr Val Gln Ala Ala Asn Leu His Leu Ser Val Leu Arg Asp Val Ser
165 170 175

Val Phe Gly Gln Arg Trp Gly Phe Asp Ala Ala Thr Ile Asn Ser Arg
180 185 190

Tyr Asn Asp Leu Thr Arg Leu Ile Gly Asn Tyr Thr Asp Tyr Ala Val
195 200 205

Arg Trp Tyr Asn Thr Gly Leu Glu Arg Val Trp Gly Pro Asp Ser Arg
210 215 220

Asp Trp Val Arg Tyr Asn Gln Phe Arg Arg Glu Leu Thr Leu Thr Val
225 230 235 240

Leu Asp Ile Val Ala Leu Phe Pro Asn Tyr Asp Ser Arg Arg Tyr Pro
245 250 255

Ile Arg Thr Val Ser Gln Leu Thr Arg Glu Ile Tyr Thr Asn Pro Val
260 265 270

Leu Glu Asn Phe Asp Gly Ser Phe Arg Gly Ser Ala Gln Gly Ile Glu
275 280 285

Arg Ser Ile Arg Ser Pro His Leu Met Asp Ile Leu Asn Ser Ile Thr
290 295 300

Ile Tyr Thr Asp Ala His Arg Gly Tyr Tyr Tyr Trp Ser Gly His Gln
305 310 315 320

Ile Met Ala Ser Pro Val Gly Phe Ser Gly Pro Glu Phe Thr Phe Pro
325 330 335

Leu Tyr Gly Thr Met Gly Asn Ala Ala Pro Gln Gln Arg Ile Val Ala
340 345 350

Gln Leu Gly Gln Gly Val Tyr Arg Thr Leu Ser Ser Thr Leu Tyr Arg

```
              355                 360                 365
Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
                660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
        690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
                740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
770                 775                 780
```

-continued

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
            805                 810                 815

Arg Asp Gly Glu Lys Cys Ala His His Ser His His Phe Ser Leu Asp
            820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
    850                 855                 860

Glu Phe Leu Glu Glu Lys Pro Leu Val Gly Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
                900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
        995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

Asn Thr Asp Glu Leu Lys Phe Ser Asn Cys Val Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 79
<211> LENGTH: 1178
<212> TYPE: PRT
<213> ORGANISM: Bacillus thuringiensis

<400> SEQUENCE: 79

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380
```

```
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
            610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
                660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
            690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
            770                 775                 780

Trp Pro Leu Ser Ala Gln Ser Pro Ile Gly Lys Cys Gly Glu Pro Asn
785                 790                 795                 800
```

Arg Cys Ala Pro His Leu Glu Trp Asn Pro Asp Leu Asp Cys Ser Cys
              805                 810                 815

Arg Asp Gly Glu Lys Cys Ala His His Ser His His Phe Ser Leu Asp
          820                 825                 830

Ile Asp Val Gly Cys Thr Asp Leu Asn Glu Asp Leu Gly Val Trp Val
      835                 840                 845

Ile Phe Lys Ile Lys Thr Gln Asp Gly His Ala Arg Leu Gly Asn Leu
  850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
              885                 890                 895

Glu Thr Asn Ile Val Tyr Lys Glu Ala Lys Glu Ser Val Asp Ala Leu
          900                 905                 910

Phe Val Asn Ser Gln Tyr Asp Gln Leu Gln Ala Asp Thr Asn Ile Ala
      915                 920                 925

Met Ile His Ala Ala Asp Lys Arg Val His Ser Ile Arg Glu Ala Tyr
  930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
              965                 970                 975

Asn Val Ile Lys Asn Gly Asp Phe Asn Asn Gly Leu Ser Cys Trp Asn
          980                 985                 990

Val Lys Gly His Val Asp Val Glu Glu Gln Asn Asn Gln Arg Ser Val
      995                 1000                1005

Leu Val Val Pro Glu Trp Glu Ala Glu Val Ser Gln Glu Val Arg
     1010                1015                1020

Val Cys Pro Gly Arg Gly Tyr Ile Leu Arg Val Thr Ala Tyr Lys
     1025                1030                1035

Glu Gly Tyr Gly Glu Gly Cys Val Thr Ile His Glu Ile Glu Asn
     1040                1045                1050

Asn Thr Asp Glu Leu Lys Phe Ser Asn Cys Val Glu Glu Ile
     1055                1060                1065

Tyr Pro Asn Asn Thr Val Thr Cys Asn Asp Tyr Thr Val Asn Gln
     1070                1075                1080

Glu Glu Tyr Gly Gly Ala Tyr Thr Ser Arg Asn Arg Gly Tyr Asn
     1085                1090                1095

Glu Ala Pro Ser Val Pro Ala Asp Tyr Ala Ser Val Tyr Glu Glu
     1100                1105                1110

Lys Ser Tyr Thr Asp Gly Arg Arg Glu Asn Pro Cys Glu Phe Asn
     1115                1120                1125

Arg Gly Tyr Arg Asp Tyr Thr Pro Leu Pro Val Gly Tyr Val Thr
     1130                1135                1140

Lys Glu Leu Glu Tyr Phe Pro Glu Thr Asp Lys Val Trp Ile Glu
     1145                1150                1155

Ile Gly Glu Thr Glu Gly Thr Phe Ile Val Asp Ser Val Glu Leu
     1160                1165                1170

Leu Leu Met Glu Glu
     1175

<210> SEQ ID NO 80
<211> LENGTH: 1178
<212> TYPE: PRT

<213> ORGANISM: Bacillus thuringiensis

<400> SEQUENCE: 80

```
Met Asp Asn Asn Pro Asn Ile Asn Glu Cys Ile Pro Tyr Asn Cys Leu
1               5                   10                  15
Ser Asn Pro Glu Val Glu Val Leu Gly Gly Glu Arg Ile Glu Thr Gly
            20                  25                  30
Tyr Thr Pro Ile Asp Ile Ser Leu Ser Leu Thr Gln Phe Leu Leu Ser
        35                  40                  45
Glu Phe Val Pro Gly Ala Gly Phe Val Leu Gly Leu Val Asp Ile Ile
    50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
            100                 105                 110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Leu Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Ser Ala Gln Gly Ile Glu
        275                 280                 285
Arg Ser Ile Arg Ser Pro His Leu Met Asp Ile Leu Asn Ser Ile Thr
    290                 295                 300
Ile Tyr Thr Asp Ala His Arg Gly Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Phe Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
```

```
Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
    690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
    770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
```

```
                    820                 825                 830
Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
            930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
            995                 1000                1005

Leu Val Val Pro Glu Trp Glu Ala Glu Val Ser Gln Glu Val Arg
        1010                1015                1020

Val Cys Pro Gly Arg Gly Tyr Ile Leu Arg Val Thr Ala Tyr Lys
        1025                1030                1035

Glu Gly Tyr Gly Glu Gly Cys Val Thr Ile His Glu Ile Glu Asn
        1040                1045                1050

Asn Thr Asp Glu Leu Lys Phe Ser Asn Cys Val Glu Glu Ile
        1055                1060                1065

Tyr Pro Asn Asn Thr Val Thr Cys Asn Asp Tyr Thr Val Asn Gln
        1070                1075                1080

Glu Glu Tyr Gly Gly Ala Tyr Thr Ser Arg Asn Arg Gly Tyr Asn
        1085                1090                1095

Glu Ala Pro Ser Val Pro Ala Asp Tyr Ala Ser Val Tyr Glu Glu
        1100                1105                1110

Lys Ser Tyr Thr Asp Gly Arg Arg Glu Asn Pro Cys Glu Phe Asn
        1115                1120                1125

Arg Gly Tyr Arg Asp Tyr Thr Pro Leu Pro Val Gly Tyr Val Thr
        1130                1135                1140

Lys Glu Leu Glu Tyr Phe Pro Glu Thr Asp Lys Val Trp Ile Glu
        1145                1150                1155

Ile Gly Glu Thr Glu Gly Thr Phe Ile Val Asp Ser Val Glu Leu
        1160                1165                1170

Leu Leu Met Glu Glu
        1175

<210> SEQ ID NO 81
<211> LENGTH: 1178
<212> TYPE: PRT
<213> ORGANISM: Bacillus thuringiensis

<400> SEQUENCE: 81
```

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
                35                  40                  45

Glu Phe Val Pro Gly Ala Gly Phe Val Leu Gly Leu Val Asp Ile Ile
50                      55                  60

Trp Gly Ile Phe Gly Pro Ser Gln Trp Asp Ala Phe Leu Val Gln Ile
65                      70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
            290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
```

```
                420              425              430
Val Ser Met Phe Arg Ser Gly Phe Ser Asn Ser Val Ser Ile Ile
            435              440              445

Arg Ala Pro Met Phe Ser Trp Ile His Arg Ser Ala Glu Phe Asn Asn
450              455              460

Ile Ile Ala Ser Asp Ser Ile Thr Gln Ile Pro Ala Val Lys Gly Asn
465              470              475              480

Phe Leu Phe Asn Gly Ser Val Ile Ser Gly Pro Gly Phe Thr Gly Gly
            485              490              495

Asp Leu Val Arg Leu Asn Ser Ser Gly Asn Asn Ile Gln Asn Arg Gly
            500              505              510

Tyr Ile Glu Val Pro Ile His Phe Pro Ser Thr Ser Thr Arg Tyr Arg
            515              520              525

Val Arg Val Arg Tyr Ala Ser Val Thr Pro Ile His Leu Asn Val Asn
            530              535              540

Trp Gly Asn Ser Ser Ile Phe Ser Asn Thr Val Pro Ala Thr Ala Thr
545              550              555              560

Ser Leu Asp Asn Leu Gln Ser Ser Asp Phe Gly Tyr Phe Glu Ser Ala
            565              570              575

Asn Ala Phe Thr Ser Ser Leu Gly Asn Ile Val Gly Val Arg Asn Phe
            580              585              590

Ser Gly Thr Ala Gly Val Ile Ile Asp Arg Phe Glu Phe Ile Pro Val
            595              600              605

Thr Ala Thr Leu Glu Ala Glu Tyr Asn Leu Glu Arg Ala Gln Lys Ala
            610              615              620

Val Asn Ala Leu Phe Thr Ser Thr Asn Gln Leu Gly Leu Lys Thr Asn
625              630              635              640

Val Thr Asp Tyr His Ile Asp Gln Val Ser Asn Leu Val Thr Tyr Leu
            645              650              655

Ser Asp Glu Phe Cys Leu Asp Glu Lys Arg Glu Leu Ser Glu Lys Val
            660              665              670

Lys His Ala Lys Arg Leu Ser Asp Glu Arg Asn Leu Leu Gln Asp Ser
            675              680              685

Asn Phe Lys Asp Ile Asn Arg Gln Pro Glu Arg Gly Trp Gly Gly Ser
690              695              700

Thr Gly Ile Thr Ile Gln Gly Gly Asp Asp Val Phe Lys Glu Asn Tyr
705              710              715              720

Val Thr Leu Ser Gly Thr Phe Asp Glu Cys Tyr Pro Thr Tyr Leu Tyr
            725              730              735

Gln Lys Ile Asp Glu Ser Lys Leu Lys Ala Phe Thr Arg Tyr Gln Leu
            740              745              750

Arg Gly Tyr Ile Glu Asp Ser Gln Asp Leu Glu Ile Tyr Leu Ile Arg
            755              760              765

Tyr Asn Ala Lys His Glu Thr Val Asn Val Pro Gly Thr Gly Ser Leu
            770              775              780

Trp Pro Leu Ser Thr Gln Ser Pro Ile Gly Lys Cys Gly Glu Pro Asn
785              790              795              800

Arg Cys Ala Pro His Leu Glu Trp Asn Pro Asp Leu Asp Cys Ser Cys
            805              810              815

Arg Asp Gly Glu Lys Cys Ala His His Ser His His Phe Ser Leu Asp
            820              825              830

Ile Asp Val Gly Cys Thr Asp Leu Asn Glu Asp Leu Gly Val Trp Val
            835              840              845
```

Ile Phe Lys Ile Lys Thr Gln Asp Gly His Ala Arg Leu Gly Asn Leu
     850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
        915                 920                 925

Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
        995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

Asn Thr Asp Glu Leu Lys Phe Ser Asn Cys Val Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 82
<211> LENGTH: 1178
<212> TYPE: PRT
<213> ORGANISM: Bacillus thuringiensis

<400> SEQUENCE: 82

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly

-continued

Tyr Thr Pro Ile Asp Ile Ser Leu Ser Leu Thr Gln Phe Leu Leu Ser
             20                  25                  30

Glu Phe Val Pro Gly Ala Gly Phe Val Leu Gly Leu Val Asp Ile Ile
         35                  40                  45

Trp Gly Ile Phe Gly Pro Ser Gln Trp Asp Ala Phe Leu Val Gln Ile
 50                  55                  60

65                  70                  75                  80

Glu Gln Leu Ile Asn Gln Arg Ile Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Leu Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

```
Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
                660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
                740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His Phe Ser Leu Asp
                820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
850                 855                 860
```

-continued

```
Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
        915                 920                 925

Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu  Glu Gln Asn Asn Gln  Arg Ser Val
        995                 1000                 1005

Leu Val  Val Pro Glu Trp  Glu Ala Glu Val Ser Gln  Glu Val Arg
    1010                 1015                 1020

Val Cys  Pro Gly Arg Gly  Tyr Ile Leu Arg Val Thr  Ala Tyr Lys
    1025                 1030                 1035

Glu Gly  Tyr Gly Glu Gly  Cys Val Thr Ile His Glu  Ile Glu Asn
    1040                 1045                 1050

Asn Thr  Asp Glu Leu Lys  Phe Ser Asn Cys Val Glu  Glu Glu Ile
    1055                 1060                 1065

Tyr Pro  Asn Asn Thr Val  Thr Cys Asn Asp Tyr Thr  Val Asn Gln
    1070                 1075                 1080

Glu Glu  Tyr Gly Gly Ala  Tyr Thr Ser Arg Asn Arg  Gly Tyr Asn
    1085                 1090                 1095

Glu Ala  Pro Ser Val Pro  Val Asp Tyr Ala Ser Val  Tyr Glu Glu
    1100                 1105                 1110

Lys Ser  Tyr Thr Asp Gly  Arg Arg Glu Asn Pro Cys  Glu Phe Asn
    1115                 1120                 1125

Arg Gly  Tyr Arg Asp Tyr  Thr Pro Leu Pro Val Gly  Tyr Val Thr
    1130                 1135                 1140

Lys Glu  Leu Glu Tyr Phe  Pro Glu Thr Asp Lys Val  Trp Ile Glu
    1145                 1150                 1155

Ile Gly  Glu Thr Glu Gly  Thr Phe Ile Val Asp Ser  Val Glu Leu
    1160                 1165                 1170

Leu Leu  Met Glu Glu
    1175

<210> SEQ ID NO 83
<211> LENGTH: 1177
<212> TYPE: PRT
<213> ORGANISM: Bacillus thuringiensis

<400> SEQUENCE: 83

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45
```

-continued

```
Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Phe Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Val Ser Ile Ile Arg
        435                 440                 445

Ala Pro Met Phe Ser Trp Ile His Arg Ser Ala Glu Phe Asn Asn Ile
450                 455                 460
```

```
Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
            485                 490                 495

Leu Val Arg Leu Asn Ser Ser Gly Asn Asn Ile Gln Asn Arg Gly Tyr
        500                 505                 510

Ile Glu Val Pro Ile His Phe Pro Ser Thr Ser Thr Arg Tyr Arg Val
    515                 520                 525

Arg Val Arg Tyr Ala Ser Val Thr Pro Ile His Leu Asn Val Asn Trp
530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
            565                 570                 575

Ala Phe Thr Ser Ser Leu Gly Asn Ile Val Gly Val Arg Asn Phe Ser
        580                 585                 590

Gly Thr Ala Gly Val Ile Ile Asp Arg Phe Glu Phe Ile Pro Val Thr
    595                 600                 605

Ala Thr Leu Glu Ala Glu Tyr Asn Leu Glu Arg Ala Gln Lys Ala Val
610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
            645                 650                 655

Asp Glu Phe Cys Leu Asp Glu Lys Arg Glu Leu Ser Glu Lys Val Lys
        660                 665                 670

His Ala Lys Arg Leu Ser Asp Glu Arg Asn Leu Leu Gln Asp Ser Asn
    675                 680                 685

Phe Lys Asp Ile Asn Arg Gln Pro Glu Arg Gly Trp Gly Gly Ser Thr
690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
            725                 730                 735

Lys Ile Asp Glu Ser Lys Leu Lys Ala Phe Thr Arg Tyr Gln Leu Arg
        740                 745                 750

Gly Tyr Ile Glu Asp Ser Gln Asp Leu Glu Ile Tyr Leu Ile Arg Tyr
    755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
            805                 810                 815

Asp Gly Glu Lys Cys Ala His His Ser His His Phe Ser Leu Asp Ile
        820                 825                 830

Asp Val Gly Cys Thr Asp Leu Asn Glu Asp Leu Gly Val Trp Val Ile
    835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
```

```
                        885                 890                 895
Thr Asn Ile Val Tyr Lys Glu Ala Lys Glu Ser Val Asp Ala Leu Phe
                    900                 905                 910

Val Asn Ser Gln Tyr Asp Gln Leu Gln Ala Asp Thr Asn Ile Ala Met
                    915                 920                 925

Ile His Ala Ala Asp Lys Arg Val His Ser Ile Arg Glu Ala Tyr Leu
            930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
                995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
    1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Ile Tyr
    1055                1060                1065

Pro Asn Asn Thr Val Thr Cys Asn Asp Tyr Thr Val Asn Gln Glu
    1070                1075                1080

Glu Tyr Gly Gly Ala Tyr Thr Ser Arg Asn Arg Gly Tyr Asn Glu
    1085                1090                1095

Ala Pro Ser Val Pro Ala Asp Tyr Ala Ser Val Tyr Glu Glu Lys
    1100                1105                1110

Ser Tyr Thr Asp Gly Arg Arg Glu Asn Pro Cys Glu Phe Asn Arg
    1115                1120                1125

Gly Tyr Arg Asp Tyr Thr Pro Leu Pro Val Gly Tyr Val Thr Lys
    1130                1135                1140

Glu Leu Glu Tyr Phe Pro Glu Thr Asp Lys Val Trp Ile Glu Ile
    1145                1150                1155

Gly Glu Thr Glu Gly Thr Phe Ile Val Asp Ser Val Glu Leu Leu
    1160                1165                1170

Leu Met Glu Glu
    1175

<210> SEQ ID NO 84
<211> LENGTH: 969
<212> TYPE: PRT
<213> ORGANISM: Bacillus thuringiensis

<400> SEQUENCE: 84

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60
```

```
Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Phe Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Val Ser Ile Ile Arg
        435                 440                 445

Ala Pro Met Phe Ser Trp Ile His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
```

```
                    485                 490                 495
Leu Val Arg Leu Asn Ser Ser Gly Asn Asn Ile Gln Asn Arg Gly Tyr
                500                 505                 510

Ile Glu Val Pro Ile His Phe Pro Ser Thr Ser Thr Arg Tyr Arg Val
                515                 520                 525

Arg Val Arg Tyr Ala Ser Val Thr Pro Ile His Leu Asn Val Asn Trp
                530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
                580                 585                 590

Gly Thr Ala Gly Val Ile Ile Asp Arg Phe Glu Phe Ile Pro Val Thr
                595                 600                 605

Ala Thr Leu Glu Ala Glu Tyr Asn Leu Glu Arg Ala Gln Lys Ala Val
                610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
                660                 665                 670

His Ala Lys Arg Leu Ser Asp Glu Arg Asn Leu Leu Gln Asp Ser Asn
                675                 680                 685

Phe Lys Asp Ile Asn Arg Gln Pro Glu Arg Gly Trp Gly Gly Ser Thr
690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
                740                 745                 750

Gly Tyr Ile Glu Asp Ser Gln Asp Leu Glu Ile Tyr Leu Ile Arg Tyr
                755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
                835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
                900                 905                 910
```

-continued

Val Asn Ser Gln Tyr Asp Gln Leu Gln Ala Asp Thr Asn Ile Ala Met
            915                 920                 925

Ile His Ala Ala Asp Lys Arg Val His Ser Ile Arg Glu Ala Trp Arg
        930                 935                 940

Asn His Gly His Ser Cys Phe Leu Cys Glu Ile Val Ile Arg Ser Gln
945                 950                 955                 960

Phe His Thr Thr Tyr Glu Pro Glu Ala
                965

<210> SEQ ID NO 85
<211> LENGTH: 1178
<212> TYPE: PRT
<213> ORGANISM: Bacillus thuringiensis

<400> SEQUENCE: 85

Met Asp Asn Asn Pro Asn Ile Asn Glu Cys Ile Pro Tyr Asn Cys Leu
1               5                   10                  15

```
            305                 310                 315                 320
        Ile Met Ala Ser Pro Val Gly Phe Ser Gly Pro Glu Phe Thr Phe Pro
                            325                 330                 335
        Leu Tyr Gly Thr Met Gly Asn Ala Ala Pro Gln Gln Arg Ile Val Ala
                            340                 345                 350
        Gln Leu Gly Gln Gly Val Tyr Arg Thr Leu Ser Ser Thr Leu Tyr Arg
                            355                 360                 365
        Arg Pro Phe Asn Ile Gly Ile Asn Asn Gln Gln Leu Ser Val Leu Asp
                            370                 375                 380
        Gly Thr Glu Phe Ala Tyr Gly Thr Ser Ser Asn Leu Pro Ser Ala Val
        385                 390                 395                 400
        Tyr Arg Lys Ser Gly Thr Val Asp Ser Leu Asp Glu Ile Pro Pro Gln
                            405                 410                 415
        Asn Asn Asn Val Pro Pro Arg Gln Gly Phe Ser His Arg Leu Ser His
                            420                 425                 430
        Val Ser Met Phe Arg Ser Gly Phe Ser Asn Ser Ser Val Ser Ile Ile
                            435                 440                 445
        Arg Ala Pro Met Phe Ser Trp Ile His Arg Ser Ala Glu Phe Asn Asn
                            450                 455                 460
        Ile Ile Ala Ser Asp Ser Ile Thr Gln Ile Pro Ala Val Lys Gly Asn
        465                 470                 475                 480
        Phe Leu Phe Asn Gly Ser Val Ile Ser Gly Pro Gly Phe Thr Gly Gly
                            485                 490                 495
        Asp Leu Val Arg Leu Asn Ser Ser Gly Asn Asn Ile Gln Asn Arg Gly
                            500                 505                 510
        Tyr Ile Glu Val Pro Ile His Phe Pro Ser Thr Ser Thr Arg Tyr Arg
                            515                 520                 525
        Val Arg Val Arg Tyr Ala Ser Val Thr Pro Ile His Leu Asn Val Asn
                            530                 535                 540
        Trp Gly Asn Ser Ser Ile Phe Ser Asn Thr Val Pro Ala Thr Ala Thr
        545                 550                 555                 560
        Ser Leu Asp Asn Leu Gln Ser Ser Asp Phe Gly Tyr Phe Glu Ser Ala
                            565                 570                 575
        Asn Ala Phe Thr Ser Ser Leu Gly Asn Ile Val Gly Val Arg Asn Phe
                            580                 585                 590
        Ser Gly Thr Ala Gly Val Ile Ile Asp Arg Phe Glu Phe Ile Pro Val
                            595                 600                 605
        Thr Ala Thr Leu Glu Ala Glu Tyr Asn Leu Glu Arg Ala Gln Lys Ala
                            610                 615                 620
        Val Asn Ala Leu Phe Thr Ser Thr Asn Gln Leu Gly Leu Lys Thr Asn
        625                 630                 635                 640
        Val Thr Asp Tyr His Ile Asp Gln Val Ser Asn Leu Val Thr Tyr Leu
                            645                 650                 655
        Ser Asp Glu Phe Cys Leu Asp Glu Lys Arg Glu Leu Ser Glu Lys Val
                            660                 665                 670
        Lys His Ala Lys Arg Leu Ser Asp Glu Arg Asn Leu Leu Gln Asp Ser
                            675                 680                 685
        Asn Phe Lys Asp Ile Asn Arg Gln Pro Glu Arg Gly Trp Gly Gly Ser
                            690                 695                 700
        Thr Gly Ile Thr Ile Gln Gly Gly Asp Asp Val Phe Lys Glu Asn Tyr
        705                 710                 715                 720
        Val Thr Leu Ser Gly Thr Phe Asp Glu Cys Tyr Pro Thr Tyr Leu Tyr
                            725                 730                 735
```

```
Gln Lys Ile Asp Glu Ser Lys Leu Lys Ala Phe Thr Arg Tyr Gln Leu
                740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His Phe Ser Leu Asp
        820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
            930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
        995                 1000                1005

Leu Val Val Pro Glu Trp Glu Ala Glu Val Ser Gln Glu Val Arg
        1010                1015                1020

Val Cys Pro Gly Arg Gly Tyr Ile Leu Arg Val Thr Ala Tyr Lys
        1025                1030                1035

Glu Gly Tyr Gly Glu Gly Cys Val Thr Ile His Glu Ile Glu Asn
        1040                1045                1050

Asn Thr Asp Glu Leu Lys Phe Ser Asn Cys Val Glu Glu Ile
        1055                1060                1065

Tyr Pro Asn Asn Thr Val Thr Cys Asn Asp Tyr Thr Val Asn Gln
        1070                1075                1080

Glu Glu Tyr Gly Gly Ala Tyr Thr Ser Arg Asn Arg Gly Tyr Asn
        1085                1090                1095

Glu Ala Pro Ser Val Pro Ala Asp Tyr Ala Ser Val Tyr Glu Glu
        1100                1105                1110

Lys Ser Tyr Thr Asp Gly Arg Arg Glu Asn Pro Cys Glu Phe Asn
        1115                1120                1125

Arg Gly Tyr Arg Asp Tyr Thr Pro Leu Pro Val Gly Tyr Val Thr
        1130                1135                1140
```

Lys Glu Leu Glu Tyr Phe Pro Glu Thr Asp Lys Val Trp Ile Glu
          1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 86
<211> LENGTH: 1177
<212> TYPE: PRT
<213> ORGANISM: Bacillus thuringiensis

<400> SEQUENCE: 86

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

```
Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Phe Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Val Ser Ile Ile Arg
        435                 440                 445

Ala Pro Met Phe Ser Trp Ile His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750
```

```
Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
        770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Lys Leu Glu Trp Glu
            885                 890                 895

Thr Asn Ile Val Tyr Lys Glu Ala Lys Glu Ser Val Asp Ala Leu Phe
                900                 905                 910

Val Asn Ser Gln Tyr Asp Gln Leu Gln Ala Asp Thr Asn Ile Ala Met
            915                 920                 925

Ile His Ala Ala Asp Lys Arg Val His Ser Ile Arg Glu Ala Tyr Leu
        930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
        995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Glu Ile Tyr
    1055                1060                1065

Pro Asn Asn Thr Val Thr Cys Asn Asp Tyr Thr Val Asn Gln Glu
    1070                1075                1080

Glu Tyr Gly Gly Ala Tyr Thr Ser Arg Asn Arg Gly Tyr Asn Glu
    1085                1090                1095

Ala Pro Ser Val Pro Ala Asp Tyr Ala Ser Val Tyr Glu Glu Lys
    1100                1105                1110

Ser Tyr Thr Asp Gly Arg Arg Glu Asn Pro Cys Glu Phe Asn Arg
    1115                1120                1125

Gly Tyr Arg Asp Tyr Thr Pro Leu Pro Val Gly Tyr Val Thr Lys
    1130                1135                1140

Glu Leu Glu Tyr Phe Pro Glu Thr Asp Lys Val Trp Ile Glu Ile
    1145                1150                1155

Gly Glu Thr Glu Gly Thr Phe Ile Val Asp Ser Val Glu Leu Leu
```

Leu Met Glu Glu
    1175

<210> SEQ ID NO 87
<211> LENGTH: 1177
<212> TYPE: PRT
<213> ORGANISM: Bacillus thuringiensis

<400> SEQUENCE: 87

Met Asp Asn Asn Pro Asn Thr Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

-continued

```
Gln Leu Gly Gln Gly Val Tyr Arg Thr Leu Ser Ser Thr Phe Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Val Ser Ile Ile Arg
        435                 440                 445

Ala Pro Met Phe Ser Trp Ile His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
```

```
              770                 775                 780
Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
                835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Lys Leu Glu Trp Glu
                885                 890                 895

Thr Asn Ile Val Tyr Lys Glu Ala Lys Glu Ser Val Asp Ala Leu Phe
                900                 905                 910

Val Asn Ser Gln Tyr Asp Gln Leu Gln Ala Asp Thr Asn Ile Ala Met
                915                 920                 925

Ile His Ala Ala Asp Lys Arg Val His Ser Ile Arg Glu Ala Tyr Leu
930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
                980                 985                 990

Lys Gly His Val Asp Val Glu Glu Gln Asn Asn Gln Arg Ser Val Leu
                995                 1000                1005

Val Val Pro Glu Trp Glu Ala Glu Val Ser Gln Glu Val Arg Val
     1010                1015                1020

Cys Pro Gly Arg Gly Tyr Ile Leu Arg Val Thr Ala Tyr Lys Glu
     1025                1030                1035

Gly Tyr Gly Glu Gly Cys Val Thr Ile His Glu Ile Glu Asn Asn
     1040                1045                1050

Thr Asp Glu Leu Lys Phe Ser Asn Cys Val Glu Glu Glu Ile Tyr
     1055                1060                1065

Pro Asn Asn Thr Val Thr Cys Asn Asp Tyr Thr Val Asn Gln Glu
     1070                1075                1080

Glu Tyr Gly Gly Ala Tyr Thr Ser Arg Asn Arg Gly Tyr Asn Glu
     1085                1090                1095

Ala Pro Ser Val Pro Ala Asp Tyr Ala Ser Val Tyr Glu Glu Lys
     1100                1105                1110

Ser Tyr Thr Asp Gly Arg Arg Glu Asn Pro Cys Glu Phe Asn Arg
     1115                1120                1125

Gly Tyr Arg Asp Tyr Thr Pro Leu Pro Val Gly Tyr Val Thr Lys
     1130                1135                1140

Glu Leu Glu Tyr Phe Pro Glu Thr Asp Lys Val Trp Ile Glu Ile
     1145                1150                1155

Gly Glu Thr Glu Gly Thr Phe Ile Val Asp Ser Val Glu Leu Leu
     1160                1165                1170

Leu Met Glu Glu
     1175
```

<210> SEQ ID NO 88
<211> LENGTH: 1180
<212> TYPE: PRT
<213> ORGANISM: Bacillus thuringiensis

<400> SEQUENCE: 88

```
Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
            35                  40                  45

Asn Met Cys Gln Gln Asn Gln Gln Tyr Gly Gly Asp Phe Glu Thr Phe
50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
            85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
            115                 120                 125

Ile Ala Ser Thr Tyr Ile Ser Asn Ala Asn Lys Ile Leu Asn Arg Ser
            130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
            165                 170                 175

Val His Tyr His Phe Gln Asn Val Ile Pro Glu Leu Val Asn Ser Cys
            180                 185                 190

Pro Pro Asn Pro Ser Asp Cys Asp Tyr Tyr Asn Ile Leu Val Leu Ser
            195                 200                 205

Ser Tyr Ala Gln Ala Ala Asn Leu His Leu Thr Val Leu Asn Gln Ala
            210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
            245                 250                 255

Ile Glu Asp Tyr Thr Asn Tyr Cys Val Thr Thr Tyr Lys Lys Gly Leu
            260                 265                 270

Asn Leu Ile Lys Thr Thr Pro Asp Ser Asn Leu Asp Gly Asn Ile Asn
            275                 280                 285

Trp Asn Thr Tyr Asn Thr Tyr Arg Thr Lys Met Thr Thr Ala Val Leu
            290                 295                 300

Asp Val Val Ala Leu Phe Pro Asn Tyr Asp Val Gly Lys Tyr Pro Ile
305                 310                 315                 320

Gly Val Gln Ser Glu Leu Thr Arg Glu Ile Tyr Gln Val Leu Asn Phe
            325                 330                 335

Glu Glu Ser Pro Tyr Lys Tyr Tyr Asp Phe Gln Tyr Gln Glu Asp Ser
            340                 345                 350

Leu Thr Arg Arg Pro His Leu Phe Thr Trp Leu Asp Ser Leu Asn Phe
            355                 360                 365

Tyr Glu Lys Ala Gln Thr Thr Pro Asn Asn Phe Phe Thr Ser His Tyr
```

```
                  370                 375                 380
Asn Met Phe His Tyr Thr Leu Asp Asn Ile Ser Gln Lys Ser Val
385                 390                 395                 400

Phe Gly Asn His Asn Val Thr Asp Lys Leu Lys Ser Leu Gly Leu Ala
                405                 410                 415

Thr Asn Ile Tyr Ile Phe Leu Leu Asn Val Ile Ser Leu Asp Asn Lys
                420                 425                 430

Tyr Leu Asn Asp Tyr Asn Asn Ile Ser Lys Met Asp Phe Phe Ile Thr
                435                 440                 445

Asn Gly Thr Arg Leu Leu Glu Lys Glu Leu Thr Ala Gly Ser Gly Gln
450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
                485                 490                 495

Tyr Ser His Ile Leu Ser Phe Ile Lys Ser Leu Ser Ile Pro Ala Thr
                500                 505                 510

Tyr Lys Thr Gln Val Tyr Thr Phe Ala Trp Thr His Ser Ser Val Asp
                515                 520                 525

Pro Lys Asn Thr Ile Tyr Thr His Leu Thr Thr Gln Ile Pro Ala Val
                530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                565                 570                 575

Cys Gln His Ser Asn Phe Gln Gln Ser Tyr Phe Ile Arg Ile Arg Tyr
                580                 585                 590

Ala Ser Asn Gly Ser Ala Asn Thr Arg Ala Val Ile Asn Leu Ser Ile
                595                 600                 605

Pro Gly Val Ala Glu Leu Gly Met Ala Leu Asn Pro Thr Phe Ser Gly
                610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                645                 650                 655

Asn Arg Ser Asp Val Tyr Thr Asn Thr Thr Val Leu Ile Asp Lys Ile
                660                 665                 670

Glu Phe Leu Pro Ile Thr Arg Ser Ile Arg Glu Asp Arg Glu Lys Gln
                675                 680                 685

Lys Leu Glu Thr Val Gln Gln Ile Ile Asn Thr Phe Tyr Ala Asn Pro
690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Glu Leu Tyr Pro Lys Glu
                725                 730                 735

Lys Met Leu Leu Leu Asp Glu Val Lys Asn Ala Lys Gln Leu Ser Gln
                740                 745                 750

Ser Arg Asn Val Leu Gln Asn Gly Asp Phe Glu Ser Ala Thr Leu Gly
                755                 760                 765

Trp Thr Thr Ser Asp Asn Ile Thr Ile Gln Glu Asp Asp Pro Ile Phe
                770                 775                 780

Lys Gly His Tyr Leu His Met Ser Gly Ala Arg Asp Ile Asp Gly Thr
785                 790                 795                 800
```

Ile Phe Pro Thr Tyr Ile Phe Gln Lys Ile Asp Glu Ser Lys Leu Lys
              805                 810                 815

Pro Tyr Thr Arg Tyr Leu Val Arg Gly Phe Val Gly Ser Ser Lys Asp
              820                 825                 830

Val Glu Leu Val Val Ser Arg Tyr Gly Glu Glu Ile Asp Ala Ile Met
              835                 840                 845

Asn Val Pro Ala Asp Leu Asn Tyr Leu Tyr Pro Ser Thr Phe Asp Cys
850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
              885                 890                 895

His Val Val Cys Gln Asp Ser His Gln Phe Ser Phe Thr Ile Asp Thr
              900                 905                 910

Gly Ala Leu Asp Thr Asn Glu Asn Ile Gly Val Trp Val Met Phe Lys
              915                 920                 925

Ile Ser Ser Pro Asp Gly Tyr Ala Ser Leu Asp Asn Leu Glu Val Ile
              930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
              965                 970                 975

Gln Ala Tyr Asp Val Ala Lys Gln Ala Ile Asp Ala Leu Phe Thr Asn
              980                 985                 990

Val Gln Asp Glu Ala Leu Gln Phe Asp Thr Thr Leu Ala Gln Ile Gln
              995                 1000                1005

Tyr Ala Glu Tyr Leu Val Gln Ser Ile Pro Tyr Val Tyr Asn Asp
              1010                1015                1020

Trp Leu Ser Asp Val Pro Gly Met Asn Tyr Asp Ile Tyr Val Glu
              1025                1030                1035

Leu Asp Ala Arg Val Ala Gln Ala Arg Tyr Leu Tyr Asp Ile Arg
              1040                1045                1050

Asn Ile Ile Lys Asn Gly Asp Phe Thr Gln Gly Val Met Gly Trp
              1055                1060                1065

His Val Thr Gly Asn Ala Asp Val Gln Gln Ile Asp Gly Val Ser
              1070                1075                1080

Val Leu Val Leu Ser Asn Trp Ser Ala Gly Val Ser Gln Asn Val
              1085                1090                1095

His Leu Gln His Asn His Gly Tyr Val Leu Gly Val Ile Ala Lys
              1100                1105                1110

Lys Glu Gly Pro Gly Asn Gly Tyr Val Thr Leu Met Asp Trp Glu
              1115                1120                1125

Glu Asn Gln Glu Lys Leu Thr Phe Thr Ser Cys Glu Glu Gly Tyr
              1130                1135                1140

Ile Thr Lys Thr Val Asp Val Phe Pro Asp Thr Asp Arg Val Arg
              1145                1150                1155

Ile Glu Ile Gly Glu Thr Glu Gly Ser Phe Tyr Ile Glu Ser Ile
              1160                1165                1170

Glu Leu Ile Cys Met Asn Glu
              1175                1180

<210> SEQ ID NO 89
<211> LENGTH: 1180

<212> TYPE: PRT
<213> ORGANISM: Bacillus thuringiensis

<400> SEQUENCE: 89

```
Met Asn Pro Tyr G

```
Phe Gly Asn His Asn Val Thr Asp Lys Leu Lys Ser Leu Gly Leu Ala
                405                 410                 415

Thr Asn Ile Tyr Ile Phe Leu Leu Asn Val Ile Ser Leu Asp Asn Lys
            420                 425                 430

Tyr Leu Asn Asp Tyr Asn Asn Ile Ser Lys Met Asp Phe Phe Ile Thr
            435                 440                 445

Asn Gly Thr Arg Leu Leu Glu Lys Glu Leu Thr Ala Gly Ser Gly Gln
        450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
                485                 490                 495

Tyr Ser His Ile Leu Ser Phe Ile Lys Ser Leu Ser Ile Pro Ala Thr
            500                 505                 510

Tyr Lys Thr Gln Val Tyr Thr Phe Ala Trp Thr His Ser Ser Val Asp
        515                 520                 525

Pro Lys Asn Thr Ile Tyr Thr His Leu Thr Thr Gln Ile Pro Ala Val
        530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                565                 570                 575

Cys Gln His Ser Asn Phe Gln Gln Ser Tyr Phe Ile Arg Ile Arg Tyr
            580                 585                 590

Ala Ser Asn Gly Ser Ala Asn Thr Arg Ala Val Ile Asn Leu Ser Ile
            595                 600                 605

Pro Gly Val Ala Glu Leu Gly Met Ala Leu Asn Pro Thr Phe Ser Gly
        610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                645                 650                 655

Asn Arg Ser Asp Val Tyr Thr Asn Thr Thr Val Leu Ile Asp Lys Ile
            660                 665                 670

Glu Phe Leu Pro Ile Thr Arg Ser Ile Arg Glu Asp Arg Glu Lys Gln
            675                 680                 685

Lys Leu Glu Thr Val Gln Gln Ile Ile Asn Thr Phe Tyr Ala Asn Pro
690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Glu Leu Tyr Pro Lys Glu
                725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
    770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
                805                 810                 815
```

Pro Tyr Thr Arg Tyr Leu Val Arg Gly Phe Val Gly Ser Ser Lys Asp
            820                 825                 830

Val Glu Leu Val Val Ser Arg Tyr Gly Glu Glu Ile Asp Ala Ile Met
        835                 840                 845

Asn Val Pro Ala Asp Leu Asn Tyr Leu Tyr Pro Ser Thr Phe Asp Cys
    850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
                885                 890                 895

His Val Val Cys Gln Asp Ser His Gln Phe Ser Phe Thr Ile Asp Thr
            900                 905                 910

Gly Ala Leu Asp Thr Asn Glu Asn Ile Gly Val Trp Val Met Phe Lys
        915                 920                 925

Ile Ser Ser Pro Asp Gly Tyr Ala Ser Leu Asp Asn Leu Glu Val Ile
    930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
                965                 970                 975

Gln Ala Tyr Asp Val Ala Lys Gln Ala Ile Asp Ala Leu Phe Thr Asn
            980                 985                 990

Val Gln Asp Glu Ala Leu Gln Phe Asp Thr Thr Leu Ala Gln Ile Gln
        995                 1000                1005

Tyr Ala Glu Tyr Leu Val Gln Ser Ile Pro Tyr Val Tyr Asn Asp
    1010                1015                1020

Trp Leu Ser Asp Val Pro Gly Met Asn Tyr Asp Ile Tyr Val Glu
    1025                1030                1035

Leu Asp Ala Arg Val Ala Gln Ala Arg Tyr Leu Tyr Asp Thr Arg
    1040                1045                1050

Asn Ile Ile Lys Asn Gly Asp Phe Thr Gln Gly Val Met Gly Trp
    1055                1060                1065

His Val Thr Gly Asn Ala Asp Val Gln Gln Ile Asp Gly Val Ser
    1070                1075                1080

Val Leu Val Leu Ser Asn Trp Ser Ala Gly Val Ser Gln Asn Val
    1085                1090                1095

His Leu Gln His Asn His Gly Tyr Val Leu Arg Val Ile Ala Lys
    1100                1105                1110

Lys Glu Gly Pro Gly Asn Gly Tyr Val Thr Leu Met Asp Cys Glu
    1115                1120                1125

Glu Asn Gln Glu Lys Leu Thr Phe Thr Ser Cys Glu Glu Gly Tyr
    1130                1135                1140

Ile Thr Lys Thr Val Asp Val Phe Pro Asp Thr Asp Arg Val Arg
    1145                1150                1155

Ile Glu Ile Gly Glu Thr Glu Gly Ser Phe Tyr Ile Glu Ser Ile
    1160                1165                1170

Glu Leu Ile Cys Met Asn Glu
    1175                1180

<210> SEQ ID NO 90
<211> LENGTH: 1180
<212> TYPE: PRT
<213> ORGANISM: Bacillus thuringiensis

<400> SEQUENCE: 90

```
Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
                20                  25                  30

Asn Ser Pro Lys Gln Leu Leu Gln Ser Thr Asn Tyr Lys Asp Trp Leu
            35                  40                  45

Asn Met Cys Gln Gln Asn Gln Gln Tyr Gly Gly Asp Phe Glu Thr Phe
50                      55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
                100                 105                 110

Thr Trp Ser Asp Phe Ile Thr Gln Thr Lys Asn Ile Ile Lys Lys Glu
            115                 120                 125

Ile Ala Ser Thr Tyr Ile Ser Asn Ala Asn Lys Ile Leu Asn Arg Ser
130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
                180                 185                 190

Pro Pro Asn Pro Ser Asp Cys Asp Tyr Tyr Asn Ile Leu Val Leu Ser
            195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
                260                 265                 270

Asn Leu Ile Lys Thr Thr Pro Asp Ser Asn Leu Asp Gly Asn Ile Asn
            275                 280                 285

Trp Asn Thr Tyr Asn Thr Tyr Arg Thr Lys Met Thr Thr Ala Val Leu
        290                 295                 300

Asp Leu Val Ala Leu Phe Pro Asn Tyr Asp Val Gly Lys Tyr Pro Ile
305                 310                 315                 320

Gly Val Gln Ser Glu Leu Thr Arg Glu Ile Tyr Gln Val Leu Asn Phe
                325                 330                 335

Glu Glu Ser Pro Tyr Lys Tyr Asp Phe Gln Tyr Gln Glu Asp Ser
            340                 345                 350

Leu Thr Arg Arg Pro His Leu Phe Thr Trp Leu Asp Ser Leu Asn Phe
                355                 360                 365

Tyr Glu Lys Ala Gln Thr Thr Pro Asn Asn Phe Phe Thr Ser His Tyr
    370                 375                 380

Asn Met Phe His Tyr Thr Leu Asp Asn Ile Ser Gln Lys Ser Ser Val
385                 390                 395                 400

Phe Gly Asn His Asn Val Thr Asp Lys Leu Lys Ser Leu Gly Leu Ala
                405                 410                 415
```

```
Thr Asn Ile Tyr Ile Phe Leu Leu Asn Val Ile Ser Leu Asp Asn Lys
            420                 425                 430

Tyr Leu Asn Asp Tyr Asn Asn Ile Ser Lys Met Asp Phe Phe Ile Thr
            435                 440                 445

Asn Gly Thr Arg Leu Leu Glu Lys Glu Leu Thr Ala Gly Ser Gly Gln
450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
                485                 490                 495

Tyr Ser His Ile Leu Ser Phe Ile Lys Ser Leu Ser Ile Pro Ala Thr
            500                 505                 510

Tyr Lys Thr Gln Val Tyr Thr Phe Ala Trp Thr His Ser Ser Val Asp
            515                 520                 525

Pro Lys Asn Thr Ile Tyr Thr His Leu Thr Thr Gln Ile Pro Ala Val
            530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                565                 570                 575

Cys Gln His Ser Asn Phe Gln Gln Ser Tyr Phe Ile Arg Ile Arg Tyr
            580                 585                 590

Ala Ser Asn Gly Ser Ala Asn Thr Arg Ala Val Ile Asn Leu Ser Ile
            595                 600                 605

Pro Gly Val Ala Glu Leu Gly Met Ala Leu Asn Pro Thr Phe Ser Gly
610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                645                 650                 655

Asn Arg Ser Asp Val Tyr Thr Asn Thr Thr Val Leu Ile Asp Lys Ile
            660                 665                 670

Glu Phe Leu Pro Ile Thr Arg Ser Ile Arg Glu Asp Arg Glu Lys Gln
            675                 680                 685

Lys Leu Glu Thr Val Gln Gln Ile Ile Asn Thr Phe Tyr Ala Asn Pro
690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Glu Leu Tyr Pro Lys Glu
                725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
                805                 810                 815

Pro Tyr Thr Arg Tyr Leu Val Arg Gly Phe Val Gly Ser Ser Lys Asp
            820                 825                 830

Val Glu Leu Val Val Ser Arg Tyr Gly Glu Glu Ile Asp Ala Ile Met
```

```
                835                 840                 845
Asn Val Pro Ala Asp Leu Asn Tyr Leu Tyr Pro Ser Thr Phe Asp Cys
            850                 855                 860
Glu Gly Ser Asn Arg Cys Glu Thr Ser Ala Val Pro Ala Asn Ile Gly
865                 870                 875                 880
Asn Thr Ser Asp Met Leu Tyr Ser Cys Gln Tyr Asp Thr Gly Lys Lys
                885                 890                 895
His Val Val Cys Gln Asp Ser His Gln Phe Ser Phe Thr Ile Asp Thr
            900                 905                 910
Gly Ala Leu Asp Thr Asn Glu Asn Ile Gly Val Trp Val Met Phe Lys
                915                 920                 925
Ile Ser Ser Pro Asp Gly Tyr Ala Ser Leu Asp Asn Leu Glu Val Ile
        930                 935                 940
Glu Glu Gly Pro Ile Asp Gly Glu Ala Leu Ser Arg Val Lys His Met
945                 950                 955                 960
Glu Lys Lys Trp Asn Asp Gln Met Glu Ala Lys Arg Ser Glu Thr Gln
                965                 970                 975
Gln Ala Tyr Asp Val Ala Lys Gln Ala Ile Asp Ala Leu Phe Thr Asn
            980                 985                 990
Val Gln Asp Glu Ala Leu Gln Phe Asp Thr Thr Leu Ala Gln Ile Gln
        995                1000                1005
Tyr Ala Glu Tyr Leu Val Gln Ser Ile Pro Tyr Val Tyr Asn Asp
       1010                1015                1020
Trp Leu Ser Asp Val Pro Gly Met Asn Tyr Asp Ile Tyr Val Glu
       1025                1030                1035
Leu Asp Ala Arg Val Ala Gln Ala Arg Tyr Leu Tyr Asp Thr Arg
       1040                1045                1050
Asn Ile Ile Lys Asn Gly Asp Phe Thr Gln Gly Val Met Gly Trp
       1055                1060                1065
His Val Thr Gly Asn Ala Asp Val Gln Gln Ile Asp Gly Val Ser
       1070                1075                1080
Val Leu Val Leu Ser Asn Trp Ser Ala Gly Val Ser Gln Asn Val
       1085                1090                1095
His Leu Gln His Asn His Gly Tyr Val Leu Arg Val Ile Ala Lys
       1100                1105                1110
Lys Glu Gly Pro Gly Asn Gly Tyr Val Thr Leu Met Asp Cys Glu
       1115                1120                1125
Glu Asn Gln Glu Lys Leu Thr Phe Thr Ser Cys Glu Glu Gly Tyr
       1130                1135                1140
Ile Thr Lys Thr Val Asp Val Phe Pro Asp Thr Asp Arg Val Arg
       1145                1150                1155
Ile Glu Ile Gly Glu Thr Glu Gly Ser Phe Tyr Ile Glu Ser Ile
       1160                1165                1170
Glu Leu Ile Cys Met Asn Glu
       1175                1180

<210> SEQ ID NO 91
<211> LENGTH: 1136
<212> TYPE: PRT
<213> ORGANISM: Bacillus thuringiensis

<400> SEQUENCE: 91

Met Asn Ser Gly Tyr Pro Leu Ala Asn Asp Leu Gln Gly Ser Met Lys
1               5                  10                  15
```

```
Asn Thr Asn Tyr Lys Asp Trp Leu Ala Met Cys Glu Asn Asn Gln Gln
                 20                  25                  30

Tyr Gly Val Asn Pro Ala Ala Ile Asn Ser Ser Val Ser Thr Ala
         35                  40                  45

Leu Lys Val Ala Gly Ala Ile Leu Lys Phe Val Asn Pro Pro Ala Gly
 50                  55                  60

Thr Val Leu Thr Val Leu Ser Ala Val Leu Pro Ile Leu Trp Pro Thr
 65                  70                  75                  80

Asn Thr Pro Thr Pro Glu Arg Val Trp Asn Asp Phe Met Thr Asn Thr
                 85                  90                  95

Gly Asn Leu Ile Asp Gln Thr Val Thr Ala Tyr Val Arg Thr Asp Ala
                 100                 105                 110

Asn Ala Lys Met Thr Val Val Lys Asp Tyr Leu Asp Gln Tyr Thr Thr
                 115                 120                 125

Lys Phe Asn Thr Trp Lys Arg Glu Pro Asn Asn Gln Ser Tyr Arg Thr
                 130                 135                 140

Ala Val Ile Thr Gln Phe Asn Leu Thr Ser Ala Lys Leu Arg Glu Thr
145                 150                 155                 160

Ala Val Tyr Phe Ser Asn Leu Val Gly Tyr Glu Leu Leu Leu Leu Pro
                 165                 170                 175

Ile Tyr Ala Gln Val Ala Asn Phe Asn Leu Leu Ile Arg Asp Gly
                 180                 185                 190

Leu Ile Asn Ala Gln Glu Trp Ser Leu Ala Arg Ser Ala Gly Asp Gln
                 195                 200                 205

Leu Tyr Asn Thr Met Val Gln Tyr Thr Lys Glu Tyr Ile Ala His Ser
                 210                 215                 220

Ile Thr Trp Tyr Asn Lys Gly Leu Asp Val Leu Arg Asn Lys Ser Asn
225                 230                 235                 240

Gly Gln Trp Ile Thr Phe Asn Asp Tyr Lys Arg Glu Met Thr Ile Gln
                 245                 250                 255

Val Leu Asp Ile Leu Ala Leu Phe Ala Ser Tyr Asp Pro Arg Arg Tyr
                 260                 265                 270

Pro Ala Asp Lys Ile Asp Asn Thr Lys Leu Ser Lys Thr Glu Phe Thr
                 275                 280                 285

Arg Glu Ile Tyr Thr Ala Leu Val Glu Ser Pro Ser Ser Lys Ser Ile
                 290                 295                 300

Ala Ala Leu Glu Ala Ala Leu Thr Arg Asp Val His Leu Phe Thr Trp
305                 310                 315                 320

Leu Lys Arg Val Asp Phe Trp Thr Asn Thr Ile Tyr Gln Asp Leu Arg
                 325                 330                 335

Phe Leu Ser Ala Asn Lys Ile Gly Phe Ser Tyr Thr Asn Ser Ser Ala
                 340                 345                 350

Met Gln Glu Ser Gly Ile Tyr Gly Ser Ser Gly Phe Gly Ser Asn Leu
                 355                 360                 365

Thr His Gln Ile Gln Leu Asn Ser Asn Val Tyr Lys Thr Ser Ile Thr
                 370                 375                 380

Asp Thr Ser Ser Pro Ser Asn Arg Val Thr Lys Met Asp Phe Tyr Lys
385                 390                 395                 400

Ile Asp Gly Thr Leu Ala Ser Tyr Asn Ser Asn Ile Thr Pro Thr Pro
                 405                 410                 415

Glu Gly Leu Arg Thr Thr Phe Phe Gly Phe Ser Thr Asn Glu Asn Thr
                 420                 425                 430

Pro Asn Gln Pro Thr Val Asn Asp Tyr Thr His Ile Leu Ser Tyr Ile
```

```
                435                440                445
Lys Thr Asp Val Ile Asp Tyr Asn Ser Asn Arg Val Ser Phe Ala Trp
450                455                460
Thr His Lys Ile Val Asp Pro Asn Asn Gln Ile Tyr Thr Asp Ala Ile
465                470                475                480
Thr Gln Val Pro Ala Val Lys Ser Asn Phe Leu Asn Ala Thr Ala Lys
                485                490                495
Val Ile Lys Gly Pro Gly His Thr Gly Gly Asp Leu Val Ala Leu Thr
                500                505                510
Ser Asn Gly Thr Leu Ser Gly Arg Met Glu Ile Gln Cys Lys Thr Ser
            515                520                525
Ile Phe Asn Asp Pro Thr Arg Ser Tyr Gly Leu Arg Ile Arg Tyr Ala
530                535                540
Ala Asn Ser Pro Ile Val Leu Asn Val Ser Tyr Val Leu Gln Gly Val
545                550                555                560
Ser Arg Gly Thr Thr Ile Ser Thr Glu Ser Thr Phe Ser Arg Pro Asn
                565                570                575
Asn Ile Ile Pro Thr Asp Leu Lys Tyr Glu Glu Phe Arg Tyr Lys Asp
                580                585                590
Pro Phe Asp Ala Ile Val Pro Met Arg Leu Ser Ser Asn Gln Leu Ile
                595                600                605
Thr Ile Ala Ile Gln Pro Leu Asn Met Thr Ser Asn Asn Gln Val Ile
        610                615                620
Ile Asp Arg Ile Glu Ile Ile Pro Ile Thr Gln Ser Val Leu Asp Glu
625                630                635                640
Thr Glu Asn Gln Asn Leu Glu Ser Glu Arg Glu Val Val Asn Ala Leu
                645                650                655
Phe Thr Asn Asp Ala Lys Asp Ala Leu Asn Ile Gly Thr Thr Asp Tyr
                660                665                670
Asp Ile Asp Gln Ala Ala Asn Leu Val Glu Cys Ile Ser Glu Glu Leu
                675                680                685
Tyr Pro Lys Glu Lys Met Leu Leu Leu Asp Glu Val Lys Asn Ala Lys
        690                695                700
Gln Leu Ser Gln Ser Arg Asn Val Leu Gln Asn Gly Asp Phe Glu Ser
705                710                715                720
Ala Thr Leu Gly Trp Thr Thr Ser Asp Asn Ile Thr Ile Gln Glu Asp
                725                730                735
Asp Pro Ile Phe Lys Gly His Tyr Leu His Met Ser Gly Ala Arg Asp
                740                745                750
Ile Asp Gly Thr Ile Phe Pro Thr Tyr Ile Phe Gln Lys Ile Asp Glu
            755                760                765
Ser Lys Leu Lys Pro Tyr Thr Arg Tyr Leu Val Arg Gly Phe Val Gly
        770                775                780
Ser Ser Lys Asp Val Glu Leu Val Val Ser Arg Tyr Gly Glu Glu Ile
785                790                795                800
Asp Ala Ile Met Asn Val Pro Ala Asp Leu Asn Tyr Leu Tyr Pro Ser
                805                810                815
Thr Phe Asp Cys Glu Gly Ser Asn Arg Cys Glu Thr Ser Ala Val Pro
            820                825                830
Ala Asn Ile Gly Asn Thr Ser Asp Met Leu Tyr Ser Cys Gln Tyr Asp
        835                840                845
Thr Gly Lys Lys His Val Val Cys Gln Asp Ser His Gln Phe Ser Phe
        850                855                860
```

Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Glu Gly Pro Ile Asp Gly Glu Ala Leu Ser Arg
            900                 905                 910

Val Lys His Met Glu Lys Lys Trp Asn Asp Gln Met Glu Ala Lys Arg
        915                 920                 925

Ser Glu Thr Gln Gln Ala Tyr Asp Val Ala Lys Gln Ala Ile Asp Ala
    930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
            980                 985                 990

Val Glu Leu Asp Ala Arg Val Ala Gln Ala Arg Tyr Leu Tyr Asp Thr
        995                 1000                1005

Arg Asn Ile Ile Lys Asn Gly Asp Phe Thr Gln Gly Val Met Gly
    1010                1015                1020

Trp His Val Thr Gly Asn Ala Asp Val Gln Gln Ile Asp Gly Val
    1025                1030                1035

Ser Val Leu Val Leu Ser Asn Trp Ser Ala Gly Val Ser Gln Asn
    1040                1045                1050

Val His Leu Gln His Asn His Gly Tyr Val Leu Arg Val Ile Ala
    1055                1060                1065

Lys Lys Glu Gly Pro Gly Asn Gly Tyr Val Thr Leu Met Asp Cys
    1070                1075                1080

Glu Glu Asn Gln Glu Lys Leu Thr Phe Thr Ser Cys Glu Glu Gly
    1085                1090                1095

Tyr Ile Thr Lys Thr Val Asp Val Phe Pro Asp Thr Asp Arg Val
    1100                1105                1110

Arg Ile Glu Ile Gly Glu Thr Glu Gly Ser Phe Tyr Ile Glu Ser
    1115                1120                1125

Ile Glu Leu Ile Cys Met Asn Glu
    1130                1135

<210> SEQ ID NO 92
<211> LENGTH: 1136
<212> TYPE: PRT
<213> ORGANISM: Bacillus thuringiensis

<400> SEQUENCE: 92

Met Asn Ser Gly Tyr Pro Leu Ala Asn Asp Leu Gln Gly Ser Met Lys
1 5 10 15

Asn Thr Asn Tyr Lys Asp Trp Leu Ala Met Cys Glu Asn Asn Gln Gln
20 25 30

Tyr Gly Val Asn Pro Ala Ala Ile Asn Ser Ser Ser Val Ser Thr Ala
35 40 45

Leu Lys Val Ala Gly Ala Ile Leu Lys Phe Val Asn Pro Pro Ala Gly
50 55 60

Thr Val Leu Thr Val Leu Ser Ala Val Leu Pro Ile Leu Trp Pro Thr
65 70 75 80

Asn Thr Pro Thr Pro Glu Arg Val Trp Asn Asp Phe Met Thr Asn Thr

-continued

```
                85                  90                  95
Gly Asn Leu Ile Asp Gln Thr Val Thr Ala Tyr Val Arg Thr Asp Ala
                100                 105                 110
Asn Ala Lys Met Thr Val Val Lys Asp Tyr Leu Asp Gln Tyr Thr Thr
                115                 120                 125
Lys Phe Asn Thr Trp Lys Arg Glu Pro Asn Asn Gln Ser Tyr Arg Thr
130                 135                 140
Ala Val Ile Thr Gln Phe Asn Leu Thr Ser Ala Lys Leu Arg Glu Thr
145                 150                 155                 160
Ala Val Tyr Phe Ser Asn Leu Val Gly Tyr Glu Leu Leu Leu Leu Pro
                165                 170                 175
Ile Tyr Ala Gln Val Ala Asn Phe Asn Leu Leu Ile Arg Asp Gly
                180                 185                 190
Leu Ile Asn Ala Gln Glu Trp Ser Leu Ala Arg Ser Arg Gly Asp Gln
                195                 200                 205
Leu Tyr Asn Thr Met Val Gln Tyr Thr Lys Glu Tyr Ile Ala His Ser
                210                 215                 220
Ile Thr Trp Tyr Asn Lys Gly Leu Asp Val Leu Arg Asn Lys Ser Asn
225                 230                 235                 240
Gly Gln Trp Ile Thr Phe Asn Asp Tyr Lys Arg Glu Met Thr Ile Gln
                245                 250                 255
Val Leu Asp Ile Leu Ala Leu Phe Ala Ser Tyr Asp Pro Arg Arg Tyr
                260                 265                 270
Pro Ala Asp Lys Ile Asp Asn Thr Lys Leu Ser Lys Thr Glu Phe Thr
                275                 280                 285
Arg Glu Ile Tyr Thr Ala Leu Val Glu Ser Pro Ser Ser Lys Ser Ile
                290                 295                 300
Ala Ala Leu Glu Ala Ala Leu Thr Arg Asp Val His Leu Phe Thr Trp
305                 310                 315                 320
Leu Lys Arg Val Asp Phe Trp Thr Asn Thr Ile Tyr Gln Asp Leu Arg
                325                 330                 335
Phe Leu Ser Ala Asn Lys Ile Gly Phe Ser Tyr Thr Asn Ser Ser Ala
                340                 345                 350
Met Gln Glu Ser Gly Ile Tyr Gly Ser Ser Gly Phe Gly Ser Asn Leu
                355                 360                 365
Thr His Gln Ile Gln Leu Asn Ser Asn Val Tyr Lys Thr Ser Ile Thr
                370                 375                 380
Asp Thr Ser Ser Pro Ser Asn Arg Val Thr Lys Met Asp Phe Tyr Lys
385                 390                 395                 400
Ile Asp Gly Thr Leu Ala Ser Tyr Asn Ser Asn Ile Thr Pro Thr Pro
                405                 410                 415
Glu Gly Leu Arg Thr Thr Phe Phe Gly Phe Ser Thr Asn Glu Asn Thr
                420                 425                 430
Pro Asn Gln Pro Thr Val Asn Asp Tyr Thr His Ile Leu Ser Tyr Ile
                435                 440                 445
Lys Thr Asp Val Ile Asp Tyr Asn Ser Asn Arg Val Ser Phe Ala Trp
                450                 455                 460
Thr His Lys Ile Val Asp Pro Asn Asn Gln Ile Tyr Thr Asp Ala Ile
465                 470                 475                 480
Thr Gln Val Pro Ala Val Lys Ser Asn Phe Leu Asn Ala Thr Ala Lys
                485                 490                 495
Val Ile Lys Gly Pro Gly His Thr Gly Gly Asp Leu Val Ala Leu Thr
                500                 505                 510
```

```
Ser Asn Gly Thr Leu Ser Gly Arg Met Glu Ile Gln Cys Lys Thr Ser
        515                 520                 525

Ile Phe Asn Asp Pro Thr Arg Ser Tyr Gly Leu Arg Ile Arg Tyr Ala
        530                 535                 540

Ala Asn Ser Pro Ile Val Leu Asn Val Ser Tyr Val Leu Gln Gly Val
545                 550                 555                 560

Ser Arg Gly Thr Thr Ile Ser Thr Glu Ser Thr Phe Ser Arg Pro Asn
                565                 570                 575

Asn Ile Ile Pro Thr Asp Leu Lys Tyr Glu Glu Phe Arg Tyr Lys Asp
            580                 585                 590

Pro Phe Asp Ala Ile Val Pro Met Arg Leu Ser Ser Asn Gln Leu Ile
        595                 600                 605

Thr Ile Ala Ile Gln Pro Leu Asn Met Thr Ser Asn Asn Gln Val Ile
        610                 615                 620

Ile Asp Arg Ile Glu Ile Ile Pro Ile Thr Gln Ser Val Leu Asp Glu
625                 630                 635                 640

Thr Glu Asn Gln Asn Leu Glu Ser Glu Arg Glu Val Val Asn Ala Leu
                645                 650                 655

Phe Thr Asn Asp Ala Lys Asp Ala Leu Asn Ile Gly Thr Thr Asp Tyr
            660                 665                 670

Asp Ile Asp Gln Ala Ala Asn Leu Val Glu Cys Ile Ser Glu Glu Leu
        675                 680                 685

Tyr Pro Lys Glu Lys Met Leu Leu Leu Asp Glu Val Lys Asn Ala Lys
        690                 695                 700

Gln Leu Ser Gln Ser Arg Asn Val Leu Gln Asn Gly Asp Phe Glu Ser
705                 710                 715                 720

Ala Thr Leu Gly Trp Thr Thr Ser Asp Asn Ile Thr Ile Gln Glu Asp
                725                 730                 735

Asp Pro Ile Phe Lys Gly His Tyr Leu His Met Ser Gly Ala Arg Asp
            740                 745                 750

Ile Asp Gly Thr Ile Phe Pro Thr Tyr Ile Phe Gln Lys Ile Asp Glu
        755                 760                 765

Ser Lys Leu Lys Pro Tyr Thr Arg Tyr Leu Val Arg Gly Phe Val Gly
        770                 775                 780

Ser Ser Lys Asp Val Glu Leu Val Val Ser Arg Tyr Gly Glu Glu Ile
785                 790                 795                 800

Asp Ala Ile Met Asn Val Pro Ala Asp Leu Asn Tyr Leu Tyr Pro Ser
                805                 810                 815

Thr Phe Asp Cys Glu Gly Ser Asn Arg Cys Glu Thr Ser Ala Val Pro
            820                 825                 830

Ala Asn Ile Gly Asn Thr Ser Asp Met Leu Tyr Ser Cys Gln Tyr Asp
        835                 840                 845

Thr Gly Lys Lys His Val Val Cys Gln Asp Ser His Gln Phe Ser Phe
        850                 855                 860

Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Glu Gly Pro Ile Asp Gly Glu Ala Leu Ser Arg
            900                 905                 910

Val Lys His Met Glu Lys Lys Trp Asn Asp Gln Met Glu Ala Lys Arg
        915                 920                 925
```

-continued

```
Ser Glu Thr Gln Gln Ala Tyr Asp Val Ala Lys Gln Ala Ile Asp Ala
    930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
            980                 985                 990

Val Glu Leu Asp Ala Arg Val Ala Gln Ala Arg Tyr Leu Tyr Asp Thr
        995                 1000                1005

Arg Asn Ile Ile Lys Asn Gly Asp Phe Thr Gln Gly Val Met Gly
    1010                1015                1020

Trp His Val Thr Gly Asn Ala Asp Val Gln Gln Ile Asp Gly Val
    1025                1030                1035

Ser Val Leu Val Leu Ser Asn Trp Ser Ala Gly Val Ser Gln Asn
    1040                1045                1050

Val His Leu Gln His Asn His Gly Tyr Val Leu Arg Val Ile Ala
    1055                1060                1065

Lys Lys Glu Gly Pro Gly Asn Gly Tyr Val Thr Leu Met Asp Cys
    1070                1075                1080

Glu Glu Asn Gln Glu Lys Leu Thr Phe Thr Ser Cys Glu Glu Gly
    1085                1090                1095

Tyr Ile Thr Lys Thr Val Asp Val Phe Pro Asp Thr Asp Arg Val
    1100                1105                1110

Arg Ile Glu Ile Gly Glu Thr Glu Gly Ser Phe Tyr Ile Glu Ser
    1115                1120                1125

Ile Glu Leu Ile Cys Met Asn Glu
    1130                1135

<210> SEQ ID NO 93
<211> LENGTH: 1136
<212> TYPE: PRT
<213> ORGANISM: Bacillus thuringiensis

<400> SEQUENCE: 93

Met Asn Ser Gly Tyr Pro Leu Ala Asn Asp Leu Gln Gly Ser Met Lys
1               5                   10                  15

Asn Thr Asn Tyr Lys Asp Trp Leu Ala Met Cys Glu Asn Asn Gln Gln
            20                  25                  30

Tyr Gly Val Asn Pro Ala Ala Ile Asn Ser Ser Ser Val Ser Thr Ala
        35                  40                  45

Leu Lys Val Ala Gly Ala Ile Leu Lys Phe Val Asn Pro Pro Ala Gly
    50                  55                  60

Thr Val Leu Thr Val Leu Ser Ala Val Leu Pro Ile Leu Trp Pro Thr
65                  70                  75                  80

Asn Thr Pro Thr Pro Glu Arg Val Trp Asn Asp Phe Met Thr Asn Thr
                85                  90                  95

Gly Asn Leu Ile Asp Gln Thr Val Thr Ala Tyr Val Arg Thr Asp Ala
            100                 105                 110

Asn Ala Lys Met Thr Val Val Lys Asp Tyr Leu Asp Gln Tyr Thr Thr
        115                 120                 125

Lys Phe Asn Thr Trp Lys Arg Glu Pro Asn Asn Gln Ser Tyr Arg Thr
    130                 135                 140

Ala Val Ile Thr Gln Phe Asn Leu Thr Ser Ala Lys Leu Arg Glu Thr
145                 150                 155                 160
```

```
Ala Val Tyr Phe Ser Asn Leu Val Gly Tyr Glu Leu Leu Leu Pro
                165             170             175

Ile Tyr Ala Gln Val Ala Asn Phe Asn Leu Leu Ile Arg Asp Gly
            180             185             190

Leu Ile Asn Ala Gln Glu Trp Ser Leu Ala Arg Ser Ala Gly Asp Gln
            195             200             205

Leu Tyr Asn Thr Met Val Gln Tyr Thr Lys Glu Tyr Ile Ala His Ser
    210             215             220

Ile Thr Trp Tyr Asn Lys Gly Leu Asp Val Leu Arg Asn Lys Ser Asn
225             230             235             240

Gly Gln Trp Ile Thr Phe Asn Asp Tyr Lys Arg Glu Met Thr Ile Gln
                245             250             255

Val Leu Asp Ile Leu Ala Leu Phe Ala Ser Tyr Asp Pro Arg Arg Tyr
            260             265             270

Pro Ala Asp Lys Ile Asp Asn Thr Lys Leu Ser Lys Thr Glu Phe Thr
            275             280             285

Arg Glu Ile Tyr Thr Ala Leu Val Glu Ser Pro Ser Ser Lys Ser Ile
    290             295             300

Ala Ala Leu Glu Ala Ala Leu Thr Arg Asp Val His Leu Phe Thr Trp
305             310             315             320

Leu Lys Arg Val Asp Phe Trp Thr Asn Thr Ile Tyr Gln Asp Leu Arg
                325             330             335

Phe Leu Ser Ala Asn Lys Ile Gly Phe Ser Tyr Thr Asn Ser Ser Ala
            340             345             350

Met Gln Glu Ser Gly Ile Tyr Gly Ser Ser Gly Phe Gly Ser Asn Leu
            355             360             365

Thr His Gln Ile Gln Leu Asn Ser Asn Val Tyr Lys Thr Ser Ile Thr
    370             375             380

Asp Thr Ser Ser Pro Ser Asn Arg Val Thr Lys Met Asp Phe Tyr Lys
385             390             395             400

Ile Asp Gly Thr Leu Ala Ser Tyr Asn Ser Asn Ile Thr Pro Thr Pro
                405             410             415

Glu Gly Leu Arg Thr Thr Phe Phe Gly Phe Ser Thr Asn Glu Asn Thr
            420             425             430

Pro Asn Gln Pro Thr Val Asn Asp Tyr Thr His Ile Leu Ser Tyr Ile
            435             440             445

Lys Thr Asp Val Ile Asp Tyr Asn Ser Asn Arg Val Ser Phe Ala Trp
    450             455             460

Thr His Lys Ile Val Asp Pro Asn Asn Gln Ile Tyr Thr Asp Ala Ile
465             470             475             480

Thr Gln Val Pro Ala Val Lys Ser Asn Phe Leu Asn Ala Thr Ala Lys
                485             490             495

Val Ile Lys Gly Pro Gly His Thr Gly Gly Asp Leu Val Ala Leu Thr
            500             505             510

Ser Asn Gly Thr Leu Ser Gly Arg Met Glu Ile Gln Cys Lys Thr Ser
            515             520             525

Ile Phe Asn Asp Pro Thr Arg Ser Tyr Gly Leu Arg Ile Arg Tyr Ala
    530             535             540

Ala Asn Ser Pro Ile Val Leu Asn Val Ser Tyr Val Leu Gln Gly Val
545             550             555             560

Ser Arg Gly Thr Thr Ile Ser Thr Glu Ser Thr Phe Ser Arg Pro Asn
                565             570             575
```

```
Asn Ile Ile Pro Thr Asp Leu Lys Tyr Glu Glu Phe Arg Tyr Lys Asp
            580                 585                 590
Pro Phe Asp Ala Ile Val Pro Met Arg Leu Ser Ser Asn Gln Leu Ile
        595                 600                 605
Thr Ile Ala Ile Gln Pro Leu Asn Met Thr Ser Asn Asn Gln Val Ile
    610                 615                 620
Ile Asp Arg Ile Glu Ile Ile Pro Ile Thr Gln Ser Val Leu Asp Glu
625                 630                 635                 640
Thr Glu Asn Gln Asn Leu Glu Ser Glu Arg Glu Val Val Asn Ala Leu
                645                 650                 655
Phe Thr Asn Asp Ala Lys Asp Ala Leu Asn Ile Gly Thr Thr Asp Tyr
            660                 665                 670
Asp Ile Asp Gln Ala Ala Asn Leu Val Glu Cys Ile Ser Glu Glu Leu
        675                 680                 685
Tyr Pro Lys Glu Lys Met Leu Leu Leu Asp Glu Val Lys Asn Ala Lys
    690                 695                 700
Gln Leu Ser Gln Ser Arg Asn Val Leu Gln Asn Gly Asp Phe Glu Ser
705                 710                 715                 720
Ala Thr Leu Gly Trp Thr Thr Ser Asp Asn Ile Thr Ile Gln Glu Asp
                725                 730                 735
Asp Pro Ile Phe Lys Gly His Tyr Leu His Met Ser Gly Ala Arg Asp
            740                 745                 750
Ile Asp Gly Thr Ile Phe Pro Thr Tyr Ile Phe Gln Lys Ile Asp Glu
        755                 760                 765
Ser Lys Leu Lys Pro Tyr Thr Arg Tyr Leu Val Arg Gly Phe Val Gly
    770                 775                 780
Ser Ser Lys Asp Val Glu Leu Val Val Ser Arg Tyr Gly Glu Glu Ile
785                 790                 795                 800
Asp Ala Ile Met Asn Val Pro Ala Asp Leu Asn Tyr Leu Tyr Pro Ser
                805                 810                 815
Thr Phe Asp Cys Glu Gly Ser Asn Arg Cys Glu Thr Ser Ala Val Pro
            820                 825                 830
Ala Asn Ile Gly Asn Thr Ser Asp Met Leu Tyr Ser Cys Gln Tyr Asp
        835                 840                 845
Thr Gly Lys Lys His Val Val Cys Gln Asp Ser His Gln Phe Ser Phe
    850                 855                 860
Thr Ile Asp Thr Gly Ala Leu Asp Thr Asn Glu Asn Ile Gly Val Trp
865                 870                 875                 880
Val Met Phe Lys Ile Ser Ser Pro Asp Gly Tyr Ala Ser Leu Asp Asn
                885                 890                 895
Leu Glu Val Ile Glu Glu Gly Pro Ile Asp Gly Glu Ala Leu Ser Arg
            900                 905                 910
Val Lys His Met Glu Lys Lys Trp Asn Asp Gln Met Glu Ala Lys Arg
        915                 920                 925
Ser Glu Thr Gln Gln Ala Tyr Asp Val Ala Lys Gln Ala Ile Asp Ala
    930                 935                 940
Leu Phe Thr Asn Val Gln Asp Glu Ala Leu Gln Phe Asp Thr Thr Leu
945                 950                 955                 960
Ala Gln Ile Gln Tyr Ala Glu Tyr Leu Val Gln Ser Ile Pro Tyr Val
                965                 970                 975
Tyr Asn Asp Trp Leu Ser Asp Val Pro Gly Met Asn Tyr Asp Ile Tyr
            980                 985                 990
Val Glu Leu Asp Ala Arg Val Ala  Gln Ala Arg Tyr Leu Tyr Asp Thr
```

```
              995                 1000                1005
Arg  Asn  Ile  Ile  Lys  Asn  Gly  Asp  Phe  Thr  Gln  Gly  Val  Met  Gly
          1010                1015                1020

Trp  His  Val  Thr  Gly  Asn  Ala  Asp  Val  Gln  Gln  Ile  Asp  Gly  Val
          1025                1030                1035

Ser  Val  Leu  Val  Leu  Ser  Asn  Trp  Ser  Ala  Gly  Val  Ser  Gln  Asn
          1040                1045                1050

Val  His  Leu  Gln  His  Asn  His  Gly  Tyr  Val  Leu  Arg  Val  Ile  Ala
          1055                1060                1065

Lys  Lys  Glu  Gly  Pro  Gly  Asn  Gly  Tyr  Val  Thr  Leu  Met  Asp  Cys
          1070                1075                1080

Glu  Glu  Asn  Gln  Glu  Lys  Leu  Thr  Phe  Thr  Ser  Cys  Glu  Glu  Gly
          1085                1090                1095

Tyr  Ile  Thr  Lys  Thr  Val  Asp  Val  Phe  Pro  Asp  Thr  Asp  Arg  Val
          1100                1105                1110

Arg  Ile  Glu  Ile  Gly  Glu  Thr  Glu  Gly  Ser  Phe  Tyr  Ile  Glu  Ser
          1115                1120                1125

Ile  Glu  Leu  Ile  Cys  Met  Asn  Glu
          1130                1135

<210> SEQ ID NO 94
<211> LENGTH: 1135
<212> TYPE: PRT
<213> ORGANISM: Bacillus thuringiensis

<400> SEQUENCE:

-continued

```
Thr Trp Tyr Asn Lys Gly Leu Asp Val Leu Arg Asn Lys Ser Asn Gly
225                 230                 235                 240

Gln Trp Ile Thr Phe Asn Asp Tyr Lys Arg Glu Met Thr Ile Gln Val
            245                 250                 255

Leu Asp Ile Leu Ala Leu Phe Ala Ser Tyr Asp Pro Arg Arg Leu Pro
        260                 265                 270

Ala Asp Lys Ile Asp Asn Thr Lys Leu Ser Lys Thr Glu Phe Thr Arg
    275                 280                 285

Glu Ile Tyr Thr Ala Leu Val Glu Ser Pro Ser Lys Ser Ile Ala
290                 295                 300

Ala Leu Glu Ala Ala Leu Thr Arg Asp Val His Leu Phe Thr Trp Leu
305                 310                 315                 320

Lys Arg Val Tyr Phe Trp Thr Asn Thr Ile Tyr Gln Asp Leu Arg Phe
                325                 330                 335

Leu Ser Ala Asn Lys Ile Gly Phe Ser Tyr Thr Asn Ser Ser Ala Met
            340                 345                 350

Gln Glu Ser Gly Ile Tyr Gly Ser Ser Phe Gly Ser Asn Leu Thr
        355                 360                 365

His Gln Ile Gln Leu Asn Ser Asn Val Tyr Lys Thr Ser Ile Thr Asp
370                 375                 380

Thr Ser Ser Pro Ser Asn Arg Val Thr Lys Met Asp Phe Tyr Lys Ile
385                 390                 395                 400

Asp Gly Thr Leu Ala Ser Tyr Asn Ser Asn Ile Thr Pro Thr Pro Glu
                405                 410                 415

Gly Leu Arg Thr Thr Phe Phe Gly Phe Ser Thr Asn Glu Asn Thr Pro
            420                 425                 430

Asn Gln Pro Thr Val Asn Asp Tyr Thr His Ile Leu Ser Tyr Ile Lys
        435                 440                 445

Thr Asp Val Ile Asp Tyr Asn Ser Asn Arg Val Ser Phe Ala Trp Thr
    450                 455                 460

His Lys Ile Val Asp Pro Asn Asn Gln Ile Tyr Thr Asp Ala Ile Thr
465                 470                 475                 480

Gln Val Pro Ala Val Lys Ser Asn Phe Leu Asn Ala Thr Ala Lys Val
                485                 490                 495

Ile Lys Gly Pro Gly His Thr Gly Gly Asp Leu Val Ala Leu Thr Ser
            500                 505                 510

Asn Gly Thr Leu Ser Gly Arg Met Glu Ile Gln Cys Lys Thr Ser Ile
        515                 520                 525

Phe Asn Asp Pro Thr Arg Ser Tyr Gly Leu Arg Ile Arg Tyr Ala Ala
    530                 535                 540

Asn Ser Pro Ile Val Leu Asn Val Ser Tyr Val Leu Gln Gly Val Ser
545                 550                 555                 560

Arg Gly Thr Thr Ile Ser Thr Glu Ser Thr Phe Ser Arg Pro Asn Asn
                565                 570                 575

Ile Ile Pro Thr Asp Leu Lys Tyr Glu Glu Phe Arg Tyr Lys Asp Pro
            580                 585                 590

Phe Asp Ala Ile Val Pro Met Arg Leu Ser Ser Asn Gln Leu Ile Thr
        595                 600                 605

Ile Ala Ile Gln Pro Leu Asn Met Thr Ser Asn Asn Gln Val Ile Ile
    610                 615                 620

Asp Arg Ile Glu Ile Ile Pro Ile Thr Gln Ser Val Leu Asp Glu Thr
625                 630                 635                 640

Glu Asn Gln Asn Leu Glu Ser Glu Arg Glu Val Val Asn Ala Leu Phe
```

```
                645                 650                 655
Thr Asn Asp Ala Lys Asp Ala Leu Asn Ile Gly Thr Thr Asp Tyr Asp
            660                 665                 670
Ile Asp Gln Ala Ala Asn Leu Val Glu Cys Ile Ser Glu Glu Leu Tyr
            675                 680                 685
Pro Lys Glu Lys Met Leu Leu Leu Asp Glu Val Lys Asn Ala Lys Gln
            690                 695                 700
Leu Ser Gln Ser Arg Asn Val Leu Gln Asn Gly Asp Phe Glu Ser Ala
705                 710                 715                 720
Thr Leu Gly Trp Thr Thr Ser Asp Asn Ile Thr Ile Gln Glu Asp Asp
            725                 730                 735
Pro Ile Phe Lys Gly His Tyr Leu His Met Ser Gly Ala Arg Asp Ile
            740                 745                 750
Asp Gly Thr Ile Phe Pro Thr Tyr Ile Phe Gln Lys Ile Asp Glu Ser
            755                 760                 765
Lys Leu Lys Pro Tyr Thr Arg Tyr Leu Val Arg Gly Phe Val Gly Ser
            770                 775                 780
Ser Lys Asp Val Glu Leu Val Val Ser Arg Tyr Gly Glu Glu Ile Asp
785                 790                 795                 800
Ala Ile Met Asn Val Pro Ala Asp Leu Asn Tyr Leu Tyr Pro Ser Thr
                805                 810                 815
Phe Asp Cys Glu Gly Ser Asn Arg Cys Glu Thr Ser Ala Val Pro Ala
                820                 825                 830
Asn Ile Gly Asn Thr Ser Asp Met Leu Tyr Ser Cys Gln Tyr Asp Thr
                835                 840                 845
Gly Lys Lys His Val Val Cys Gln Asp Ser His Gln Phe Ser Phe Thr
                850                 855                 860
Ile Asp Thr Gly Ala Leu Asp Thr Asn Glu Asn Ile Gly Val Trp Val
865                 870                 875                 880
Met Phe Lys Ile Ser Ser Pro Asp Gly Tyr Ala Ser Leu Asp Asn Leu
                885                 890                 895
Glu Val Ile Glu Glu Gly Pro Ile Asp Gly Glu Ala Leu Ser Arg Val
                900                 905                 910
Lys His Met Glu Lys Lys Trp Asn Asp Gln Met Glu Ala Lys Arg Ser
                915                 920                 925
Glu Thr Gln Gln Ala Tyr Asp Val Ala Lys Gln Ala Ile Asp Ala Leu
            930                 935                 940
Phe Thr Asn Val Gln Asp Glu Ala Leu Gln Phe Asp Thr Thr Leu Ala
945                 950                 955                 960
Gln Ile Gln Tyr Ala Glu Tyr Leu Val Gln Ser Ile Pro Tyr Val Tyr
                965                 970                 975
Asn Asp Trp Leu Ser Asp Val Pro Gly Met Asn Tyr Asp Ile Tyr Val
            980                 985                 990
Glu Leu Asp Ala Arg Val Ala Gln Ala Arg Tyr Leu Tyr Asp Thr Arg
            995                 1000                1005
Asn Ile Ile Lys Asn Gly Asp Phe Thr Gln Gly Val Met Gly Trp
        1010                1015                1020
His Val Thr Gly Asn Ala Asp Val Gln Gln Ile Asp Gly Val Ser
        1025                1030                1035
Val Leu Val Leu Ser Asn Trp Ser Ala Gly Val Ser Gln Asn Val
        1040                1045                1050
His Leu Gln His Asn His Gly Tyr Val Leu Arg Val Ile Ala Lys
        1055                1060                1065
```

```
Lys Glu Gly Pro Gly Asn Gly Tyr Val Thr Leu Met Asp Cys Glu
        1070                1075                1080

Glu Asn Gln Glu Lys Leu Thr Phe Thr Ser Cys Glu Glu Gly Tyr
        1085                1090                1095

Ile Thr Lys Thr Val Asp Val Phe Pro Asp Thr Asp Arg Val Arg
        1100                1105                1110

Ile Glu Ile Gly Glu Thr Glu Gly Ser Phe Tyr Ile Glu Ser Ile
        1115                1120                1125

Glu Leu Ile Cys Met Asn Glu
        1130                1135

<210> SEQ ID NO 95
<211> LENGTH: 1135
<212> TYPE: PRT
<213> ORGANISM: Bacillus thuringiensis

<400> SEQUENCE: 95

Met Asn Ser Gly Tyr Pro Leu Ala Asn Asp Leu Gln Gly Ser Met Lys
1               5                   10                  15

Asn Thr Asn Tyr Lys Asp Trp Leu Ala Met Cys Glu Asn Asn Gln Gln
            20                  25                  30

Tyr Gly Val Asn Pro Ala Ala Ile Asn Ser Ser Val Ser Thr Ala
        35                  40                  45

Leu Lys Asp Ala Gly Ala Ile Leu Lys Phe Val Asn Pro Pro Ala Gly
    50                  55                  60

Ser Val Leu Thr Val Leu Ser Ala Val Leu Pro Ile Leu Trp Pro Thr
65                  70                  75                  80

Asn Thr Pro Thr Pro Glu Arg Val Trp Asn Asp Phe Met Thr Asn Thr
                85                  90                  95

Gly Asn Leu Ile Asp Gln Thr Val Thr Ala Tyr Val Arg Thr Asp Ala
            100                 105                 110

Asn Ala Lys Met Thr Val Val Lys Asp Tyr Leu Asp Gln Tyr Thr Thr
        115                 120                 125

Lys Phe Asn Thr Trp Lys Arg Glu Pro Asn Asn Gln Ser Tyr Arg Thr
    130                 135                 140

Ala Val Ile Thr Gln Phe Asn Leu Thr Ser Ala Lys Leu Arg Glu Thr
145                 150                 155                 160

Ala Val Tyr Phe Ser Asn Leu Val Gly Tyr Glu Leu Leu Leu Leu Pro
                165                 170                 175

Ile Tyr Ala Gln Val Ala Asn Phe Asn Leu Leu Leu Ile Arg Asp Gly
            180                 185                 190

Pro His Lys Cys Thr Arg Met Val Tyr Ala Arg Ser Cys Asp Gln Leu
        195                 200                 205

Tyr Asn Thr Met Val Gln Tyr Thr Lys Glu Tyr Ile Ala His Ser Ile
    210                 215                 220

Thr Trp Tyr Asn Lys Gly Leu Asp Val Leu Arg Asn Lys Ser Asn Gly
225                 230                 235                 240

Gln Trp Ile Thr Phe Asn Asp Tyr Lys Arg Glu Met Thr Ile Gln Val
                245                 250                 255

Leu Asp Ile Leu Ala Leu Phe Ala Ser Tyr Asp Pro Arg Arg Tyr Pro
            260                 265                 270

Ala Asp Lys Ile Asp Asn Thr Lys Leu Ser Lys Thr Glu Phe Thr Arg
        275                 280                 285

Glu Ile Tyr Thr Ala Leu Val Glu Ser Pro Ser Ser Lys Ser Ile Ala
```

```
                290                 295                 300
Ala Leu Glu Ala Ala Leu Thr Arg Asp Val His Leu Phe Thr Trp Leu
305                 310                 315                 320
Lys Arg Val Asp Phe Trp Thr Asn Thr Ile Tyr Gln Asp Leu Arg Phe
                325                 330                 335
Leu Ser Ala Asn Lys Ile Gly Phe Ser Tyr Thr Asn Ser Ser Ala Met
                340                 345                 350
Gln Glu Ser Gly Ile Tyr Gly Ser Ser Gly Leu Val Gln Ile Tyr Leu
                355                 360                 365
Ile Lys Phe Asn Leu Ile Leu Ile Val Ile Lys Leu Leu Ser Gln Ile
                370                 375                 380
Leu Ala Pro Pro Leu Ile Glu Leu Gln Lys Trp Ile Ser Thr Lys Phe
385                 390                 395                 400
Asp Gly Thr Leu Ala Ser Tyr Asn Ser Asn Ile Thr Pro Thr Pro Glu
                405                 410                 415
Gly Leu Arg Thr Thr Phe Phe Gly Phe Ser Thr Asn Glu Asn Thr Pro
                420                 425                 430
Asn Gln Pro Thr Val Asn Asp Tyr Thr His Ile Leu Ser Tyr Ile Lys
                435                 440                 445
Thr Asp Val Ile Asp Tyr Asn Ser Asn Arg Val Ser Phe Ala Trp Thr
450                 455                 460
His Asn Ile Val Asp Pro Asn Asn Gln Ile Tyr Thr Asp Ala Ile Thr
465                 470                 475                 480
Gln Val Pro Ala Val Lys Ser Asn Phe Leu Asn Ala Thr Ala Arg Val
                485                 490                 495
Ile Lys Gly Pro Gly His Thr Gly Gly Asp Leu Val Ala Leu Thr Ser
                500                 505                 510
Asn Gly Thr Leu Ser Gly Gly Arg Met Glu Ile Gln Cys Lys Thr Ser
                515                 520                 525
Ile Phe Asn Asp Pro Thr Arg Ser Tyr Gly Leu Arg Ile Arg Tyr Ala
                530                 535                 540
Ala Asn Ser Pro Ile Val Ile Glu Cys Asp His Met Tyr Tyr Lys Glu
545                 550                 555                 560
Phe Leu Glu Glu Gln Arg Leu Val Gln Asn Tyr Val Ser Arg Pro Asn
                565                 570                 575
Asn Ile Ile Pro Thr Asp Leu Lys Tyr Glu Glu Phe Arg Tyr Lys Asp
                580                 585                 590
Pro Asn Asp Ala Ile Val Pro Met Arg Leu Ser Ser Asn Gln Leu Ile
                595                 600                 605
Thr Ile Ala Ile Gln Pro Leu Asn Met Thr Ser Asn Asn Gln Val Ile
610                 615                 620
Ile Asp Arg Ile Glu Ile Pro Ile Thr Gln Ser Val Leu Asp Glu
625                 630                 635                 640
Thr Glu Asn Gln Asn Leu Glu Ser Glu Arg Glu Val Val Asn Ala Leu
                645                 650                 655
Phe Thr Asn Asp Ala Lys Asp Ala Leu Asn Ile Gly Thr Thr Asp Tyr
                660                 665                 670
Asp Ile Asp Gln Ala Ala Asn Leu Val Glu Cys Ile Ser Glu Gly Ile
                675                 680                 685
Ile Ser Lys Glu Lys Met Leu Leu Leu Asp Glu Val Lys Asn Ala Lys
                690                 695                 700
Gln Leu Ser Gln Ser Arg Asn Val Leu Gln Asn Gly Asp Phe Glu Ser
705                 710                 715                 720
```

-continued

```
Arg Thr Leu Gly Trp Thr Thr Ser Asp Asn Ile Thr Ile Gln Glu Asp
                725                 730                 735

Asp Pro Ile Phe Lys Gly His Tyr Leu His Met Ser Gly Ala Arg Asp
            740                 745                 750

Ile Asp Gly Thr Ile Phe Pro Thr Tyr Ile Phe Gln Lys Ile Asp Glu
        755                 760                 765

Ser Lys Leu Lys Pro Tyr Thr Arg Tyr Leu Val Arg Gly Phe Val Gly
770                 775                 780

Ser Ser Lys Asp Val Glu Leu Val Val Ser Arg Tyr Gly Glu Glu Ile
785                 790                 795                 800

Asp Ala Ile Met Asn Val Pro Ala Asp Leu Asn Tyr Leu Tyr Pro Ser
                805                 810                 815

Thr Phe Asp Cys Glu Gly Leu Ile Val Val Ser Val Arg Cys Ala Ala
            820                 825                 830

Asn Ile Trp Asp Thr Ser Asp Met Leu Tyr Ser Cys Gln Tyr Asp Thr
        835                 840                 845

Gly Lys Lys His Val Val Cys Gln Asp Ser His Gln Phe Ser Phe Thr
    850                 855                 860

Ile Asp Thr Gly Ala Leu Asp Thr Asn Glu Asn Ile Gly Val Trp Val
865                 870                 875                 880

Met Phe Lys Ile Ser Ser Pro Asp Gly Tyr Ala Ser Leu Asp Asn Leu
                885                 890                 895

Glu Val Ile Glu Arg Gly Pro Ile Asp Gly Glu Ala Leu Ser Arg Val
            900                 905                 910

Lys His Met Glu Lys Lys Trp Asn Asp Gln Met Glu Lys Arg Ser
        915                 920                 925

Glu Thr Gln Gln Ala Tyr Asp Val Ala Lys Gln Ala Ile Asp Ala Leu
    930                 935                 940

Phe Thr Asn Val Gln Asp Glu Ala Leu Gln Phe Asp Thr Thr Leu Ala
945                 950                 955                 960

Gln Ile Gln Tyr Ala Glu Tyr Leu Val Gln Ser Ile Pro Tyr Val Tyr
                965                 970                 975

Asn Asp Trp Leu Ser Asp Val Pro Gly Met Asn Tyr Asp Ile Tyr Val
            980                 985                 990

Glu Leu Asp Ala Arg Val Ala Gln Ala Arg Tyr Leu Tyr Asp Thr Arg
        995                 1000                1005

Asn Ile Ile Lys Asn Val Asp Phe Thr Gln Gly Val Met Gly Trp
    1010                1015                1020

His Val Thr Gly Asn Ala Asp Val Gln Gln Ile Asp Gly Val Ser
    1025                1030                1035

Val Leu Val Leu Ser Asn Trp Ser Ala Gly Val Ser Gln Asn Val
    1040                1045                1050

His Leu Gln His Asn His Gly Tyr Val Leu Arg Val Ile Ala Lys
    1055                1060                1065

Lys Glu Gly Pro Gly Asn Gly Tyr Val Thr Leu Met Asp Cys Glu
    1070                1075                1080

Glu Asn Gln Glu Lys Leu Thr Phe Thr Ser Cys Glu Glu Gly Tyr
    1085                1090                1095

Ile Thr Lys Thr Val Asp Val Phe Pro Asp Thr Asp Arg Val Arg
    1100                1105                1110

Ile Glu Ile Gly Glu Thr Glu Gly Ser Phe Tyr Ile Glu Ser Ile
    1115                1120                1125
```

```
Glu Leu Ile Cys Met Asn Glu
    1130            1135

<210> SEQ ID NO 96
<211> LENGTH: 1160
<212> TYPE: PRT
<213> ORGANISM: Bacillus thuringiensis

<400> SEQUENCE: 96

Met Ser Pro Asn Asn Gln Asn Glu Tyr Glu Ile Ile Asp Ala Leu Ser
1               5                   10                  15

Pro Thr Ser Val Ser Asp Asn Ser Ile Arg Tyr Pro Leu Ala Asn Asp
            20                  25                  30

Gln Thr Asn Thr Leu Gln Asn Met Asn Tyr Lys Asp Tyr Leu Lys Met
        35                  40                  45

Thr Glu Ser Thr Asn Ala Glu Leu Ser Arg Asn Pro Gly Thr Phe Ile
    50                  55                  60

Ser Ala Gln Asp Ala Val Gly Thr Gly Ile Asp Ile Val Ser Thr Ile
65                  70                  75                  80

Ile Ser Gly Leu Gly Ile Pro Val Leu Gly Glu Val Phe Ser Ile Leu
                85                  90                  95

Gly Ser Leu Ile Gly Leu Leu Trp Pro Ser Asn Asn Glu Asn Val Trp
            100                 105                 110

Gln Ile Phe Met Asn Arg Val Glu Glu Leu Ile Asp Gln Lys Ile Leu
        115                 120                 125

Asp Ser Val Arg Ser Arg Ala Ile Ala Asp Leu Ala Asn Ser Arg Ile
    130                 135                 140

Ala Val Glu Tyr Tyr Gln Asn Ala Leu Glu Asp Trp Arg Lys Asn Pro
145                 150                 155                 160

His Ser Thr Arg Ser Ala Ala Leu Val Lys Glu Arg Phe Gly Asn Ala
                165                 170                 175

Glu Ala Ile Leu Arg Thr Asn Met Gly Ser Phe Ser Gln Thr Asn Tyr
            180                 185                 190

Glu Thr Pro Leu Leu Pro Thr Tyr Ala Gln Ala Ala Ser Leu His Leu
        195                 200                 205

Leu Val Met Arg Asp Val Gln Ile Tyr Gly Lys Glu Trp Gly Tyr Pro
    210                 215                 220

Gln Asn Asp Ile Asp Leu Phe Tyr Lys Glu Gln Val Ser Tyr Thr Ala
225                 230                 235                 240

Arg Tyr Ser Asp His Cys Val Gln Trp Tyr Asn Ala Gly Leu Asn Lys
                245                 250                 255

Leu Arg Gly Thr Gly Ala Lys Gln Trp Val Asp Tyr Asn Arg Phe Arg
            260                 265                 270

Arg Glu Met Asn Val Met Val Leu Asp Leu Val Ala Leu Phe Pro Asn
        275                 280                 285

Tyr Asp Ala Arg Ile Tyr Pro Leu Glu Thr Asn Ala Glu Leu Thr Arg
    290                 295                 300

Glu Ile Phe Thr Asp Pro Val Gly Ser Tyr Val Thr Gly Gln Ser Ser
305                 310                 315                 320

Thr Leu Ile Ser Trp Tyr Asp Met Ile Pro Ala Ala Leu Pro Ser Phe
                325                 330                 335

Ser Thr Leu Glu Asn Leu Leu Arg Lys Pro Asp Phe Phe Thr Leu Leu
            340                 345                 350

Gln Glu Ile Arg Met Tyr Thr Ser Phe Arg Gln Asn Gly Thr Ile Glu
        355                 360                 365
```

-continued

```
Tyr Tyr Asn Tyr Trp Gly Gly Gln Arg Leu Thr Leu Ser Tyr Ile Tyr
370                 375                 380

Gly Ser Ser Phe Asn Lys Tyr Ser Gly Val Leu Ala Gly Ala Glu Asp
385                 390                 395                 400

Ile Ile Pro Val Gly Gln Asn Asp Ile Tyr Arg Val Val Trp Thr Tyr
            405                 410                 415

Ile Gly Arg Tyr Thr Asn Ser Leu Leu Gly Val Asn Pro Val Thr Phe
            420                 425                 430

Tyr Phe Ser Asn Asn Thr Gln Lys Thr Tyr Ser Lys Pro Lys Gln Phe
        435                 440                 445

Ala Gly Gly Ile Lys Thr Ile Asp Ser Gly Glu Glu Leu Thr Tyr Glu
450                 455                 460

Asn Tyr Gln Ser Tyr Ser His Arg Val Ser Tyr Ile Thr Ser Phe Glu
465                 470                 475                 480

Ile Lys Ser Thr Gly Gly Thr Val Leu Gly Val Val Pro Ile Phe Gly
                485                 490                 495

Trp Thr His Ser Ser Ala Ser Arg Asn Asn Phe Ile Tyr Ala Thr Lys
            500                 505                 510

Ile Ser Gln Ile Pro Ile Asn Lys Ala Ser Arg Thr Ser Gly Gly Ala
        515                 520                 525

Val Trp Asn Phe Gln Glu Gly Leu Tyr Asn Gly Gly Pro Val Met Lys
530                 535                 540

Leu Ser Gly Ser Gly Ser Gln Val Ile Asn Leu Arg Val Ala Thr Asp
545                 550                 555                 560

Ala Lys Gly Ala Ser Gln Arg Tyr Arg Ile Arg Ile Arg Tyr Ala Ser
                565                 570                 575

Asp Arg Ala Gly Lys Phe Thr Ile Ser Ser Arg Ser Pro Glu Asn Pro
            580                 585                 590

Ala Thr Tyr Ser Ala Ser Ile Ala Tyr Thr Asn Thr Met Ser Thr Asn
        595                 600                 605

Ala Ser Leu Thr Tyr Ser Thr Phe Ala Tyr Ala Glu Ser Gly Pro Ile
610                 615                 620

Asn Leu Gly Ile Ser Gly Ser Ser Arg Thr Phe Asp Ile Ser Ile Thr
625                 630                 635                 640

Lys Glu Ala Gly Ala Ala Asn Leu Tyr Ile Asp Arg Ile Glu Phe Ile
                645                 650                 655

Pro Val Asn Thr Leu Phe Glu Ala Glu Glu Asp Leu Asp Val Ala Lys
            660                 665                 670

Lys Ala Val Asn Gly Leu Phe Thr Asn Glu Lys Asp Ala Leu Gln Thr
        675                 680                 685

Ser Val Thr Asp Tyr Gln Val Asn Gln Ala Ala Asn Leu Ile Glu Cys
690                 695                 700

Leu Ser Asp Glu Leu Tyr Pro Asn Glu Lys Arg Met Leu Trp Asp Ala
705                 710                 715                 720

Val Lys Glu Ala Lys Arg Leu Val Gln Ala Arg Asn Leu Leu Gln Asp
                725                 730                 735

Thr Gly Phe Asn Arg Ile Asn Gly Glu Asn Gly Trp Thr Gly Ser Thr
            740                 745                 750

Gly Ile Glu Val Val Glu Gly Asp Val Leu Phe Lys Asp Arg Ser Leu
        755                 760                 765

Arg Leu Thr Ser Ala Arg Glu Ile Asp Thr Glu Thr Tyr Pro Thr Tyr
770                 775                 780
```

```
Leu Tyr Gln Gln Ile Asp Glu Ser Leu Leu Lys Pro Tyr Thr Arg Tyr
785                 790                 795                 800

Lys Leu Lys Gly Phe Ile Gly Ser Ser Gln Asp Leu Glu Ile Lys Leu
            805                 810                 815

Ile Arg His Arg Ala Asn Gln Ile Val Lys Asn Val Pro Asp Asn Leu
            820                 825                 830

Leu Pro Asp Val Arg Pro Val Asn Ser Cys Gly Gly Val Asp Arg Cys
            835                 840                 845

Ser Glu Gln Gln Tyr Val Asp Ala Asn Leu Ala Leu Glu Asn Asn Gly
850                 855                 860

Glu Asn Gly Asn Met Ser Ser Asp Ser His Ala Phe Ser Phe His Ile
865                 870                 875                 880

Asp Thr Gly Glu Ile Asp Leu Asn Glu Asn Thr Gly Ile Trp Ile Val
            885                 890                 895

Phe Lys Ile Pro Thr Thr Asn Gly Asn Ala Thr Leu Gly Asn Leu Glu
            900                 905                 910

Phe Val Glu Glu Gly Pro Leu Ser Gly Glu Thr Leu Glu Trp Ala Gln
            915                 920                 925

Gln Gln Glu Gln Gln Trp Gln Asp Lys Met Ala Arg Lys Arg Ala Ala
930                 935                 940

Ser Glu Lys Thr Tyr Tyr Ala Ala Lys Gln Ala Ile Asp Arg Leu Phe
945                 950                 955                 960

Ala Asp Tyr Gln Asp Gln Lys Leu Asn Ser Gly Val Glu Met Ser Asp
            965                 970                 975

Leu Leu Ala Ala Gln Asn Leu Val Gln Ser Ile Pro Tyr Val Tyr Asn
            980                 985                 990

Asp Ala Leu Pro Glu Ile Pro Gly Met Asn Tyr Thr Ser Phe Thr Glu
            995                 1000                1005

Leu Thr Asn Arg Leu Gln Gln Ala Trp Asn Leu Tyr Asp Leu Gln
    1010                1015                1020

Asn Ala Ile Pro Asn Gly Asp Phe Arg Asn Gly Leu Ser Asn Trp
    1025                1030                1035

Asn Ala Thr Ser Asp Val Asn Val Gln Gln Leu Ser Asp Thr Ser
    1040                1045                1050

Val Leu Val Ile Pro Asn Trp Asn Ser Gln Val Ser Gln Gln Phe
    1055                1060                1065

Thr Val Gln Pro Asn Tyr Arg Tyr Val Leu Arg Val Thr Ala Arg
    1070                1075                1080

Lys Glu Gly Val Gly Asp Gly Tyr Val Ile Ile Arg Asp Gly Ala
    1085                1090                1095

Asn Gln Thr Glu Thr Leu Thr Phe Asn Ile Cys Asp Asp Asp Thr
    1100                1105                1110

Gly Val Leu Ser Thr Asp Gln Thr Ser Tyr Ile Thr Lys Thr Val
    1115                1120                1125

Glu Phe Thr Pro Ser Thr Glu Gln Val Trp Ile Asp Met Ser Glu
    1130                1135                1140

Thr Glu Gly Val Phe Asn Ile Glu Ser Val Glu Leu Val Leu Glu
    1145                1150                1155

Glu Glu
    1160

<210> SEQ ID NO 97
<211> LENGTH: 20
<212> TYPE: DNA
```

```
<213> ORGANISM: Artificial
<220> FEATURE:
<223> OTHER INFORMATION: Primer CRP_1f

<400> SEQUENCE: 97
ggatcccaga ccgacatgtc                                                     20

<210> SEQ ID NO 98
<211> LENGTH: 75
<212> TYPE: DNA
<213> ORGANISM: Artificial
<220> FEATURE:
<223> OTHER INFORMATION: Primer CRP_2r

<400> SEQUENCE: 98
cggtgctttc agggatacat aggaagtatc agactctttc gggaacacga aagctttgcg        60
agacatgtcg gtctg                                                          75

<210> SEQ ID NO 99
<211> LENGTH: 75
<212> TYPE: DNA
<213> ORGANISM: Artificial
<220> FEATURE:
<223> OTHER INFORMATION: Primer CRP_3f

<400> SEQUENCE: 99
tccctgaaag caccgctgac gaaacctctg aaagccttca ctgtttgcct ccacttctac        60
acggaactgt cctct                                                          75

<210> SEQ ID NO 100
<211> LENGTH: 75
<212> TYPE: DNA
<213> ORGANISM: Artificial
<220> FEATURE:
<223> OTHER INFORMATION: Primer CRP_4r

<400> SEQUENCE: 100
gatcagaatc tcattgtctt ggcgcttggt ggcatagctg aaaatgctgt agccacgggt        60
agaggacagt tccgt                                                          75

<210> SEQ ID NO 101
<211> LENGTH: 75
<212> TYPE: DNA
<213> ORGANISM: Artificial
<220> FEATURE:
<223> OTHER INFORMATION: Primer CRP_5f

<400> SEQUENCE: 101
aatgagattc tgatcttttg gtctaaagat attggttaca gctttaccgt tggtggctct        60
gaaatcctgt tcgaa                                                          75

<210> SEQ ID NO 102
<211> LENGTH: 75
<212> TYPE: DNA
<213> ORGANISM: Artificial
<220> FEATURE:
<223> OTHER INFORMATION: Primer CRP_6r

<400> SEQUENCE: 102
accagaggcg gactcccagc tggtacaaat gtgtactgga gctacggtga cttcaggaac        60
ttcgaacagg atttc                                                          75
```

-continued

```
<210> SEQ ID NO 103
<211> LENGTH: 75
<212> TYPE: DNA
<213> ORGANISM: Artificial
<220> FEATURE:
<223> OTHER INFORMATION: Primer CRP_7f

<400> SEQUENCE: 103
gagtccgcct ctggtatcgt tgagttctgg gtagatggta aaccgcgcgt gcgtaagtcc      60
ctgaagaaag gctac                                                      75

<210> SEQ ID NO 104
<211> LENGTH: 75
<212> TYPE: DNA
<213> ORGANISM: Artificial
<220> FEATURE:
<223> OTHER INFORMATION: Primer CRP_8r

<400> SEQUENCE: 104
gttgccaccg aaggaatcct gttcctgacc caagatgatg ctcgcttctg cgcccacagt      60 gtagccttc ttcag                                                       75

<210> SEQ ID NO 105
<211> LENGTH: 75
<212> TYPE: DNA
<213> ORGANISM: Artificial
<220> FEATURE:
<223> OTHER INFORMATION: Primer CRP_9f

<400> SEQUENCE: 105
tccttcggtg gcaactttga aggtagccag tccctggttg gtgacattgg caatgtgaac      60
atgtgggact ttgtg                                                      75

<210> SEQ ID NO 106
<211> LENGTH: 75
<212> TYPE: DNA
<213> ORGANISM: Artificial
<220> FEATURE:
<223> OTHER INFORMATION: Primer CRP_10r

<400> SEQUENCE: 106
caggacatta ggactgaacg gaccgccaag atagatggtg ttaatttcat ctggtgacag      60
cacaaagtcc cacat                                                      75

<210> SEQ ID NO 107
<211> LENGTH: 75
<212> TYPE: DNA
<213> ORGANISM: Artificial
<220> FEATURE:
<223> OTHER INFORMATION: Primer CRP_11f

<400> SEQUENCE: 107
agtcctaatg tcctgaactg gcgtgcactg aagtatgaag tgcaaggcga agtgttcacc      60
aaaccgcagc tgtgg                                                      75

<210> SEQ ID NO 108
<211> LENGTH: 26
<212> TYPE: DNA
<213> ORGANISM: Artificial
<220> FEATURE:
<223> OTHER INFORMATION: Primer CRP_12r

<400> SEQUENCE: 108
```

-continued

```
ctcgagcggc cacagctgcg gtttgg                                          26
```

<210> SEQ ID NO 109
<211> LENGTH: 630
<212> TYPE: DNA
<213> ORGANISM: Homo sapiens
<220> FEATURE:
<221> NAME/KEY: CDS
<222> LOCATION: (1)..(630)
<223> OTHER INFORMATION:

<400> SEQUENCE: 109

```
gga tcc cag acc gac atg tct cgc aaa gct ttc gtg ttc ccg aaa gag      48
Gly Ser Gln Thr Asp Met Ser Arg Lys Ala Phe Val Phe Pro Lys Glu
1               5                   10                  15 tct gat act tcc tat gta tcc ctg aaa gca ccg ctg acg aaa cct ctg      96
Ser Asp Thr Ser Tyr Val Ser Leu Lys Ala Pro Leu Thr Lys Pro Leu
            20                  25                  30 aaa gcc ttc act gtt tgc ctc cac ttc tac acg gaa ctg tcc tct acc     144
Lys Ala Phe Thr Val Cys Leu His Phe Tyr Thr Glu Leu Ser Ser Thr
        35                  40                  45 cgt ggc tac agc att ttc agc tat gcc acc aag cgc caa gac aat gag     192
Arg Gly Tyr Ser Ile Phe Ser Tyr Ala Thr Lys Arg Gln Asp Asn Glu
    50                  55                  60 att ctg atc ttt tgg tct aaa gat att ggt tac agc ttt acc gtt ggt     240
Ile Leu Ile Phe Trp Ser Lys Asp Ile Gly Tyr Ser Phe Thr Val Gly
65                  70                  75                  80 ggc tct gaa atc ctg ttc gaa gtt cct gaa gtc acc gta gct cca gta     288
Gly Ser Glu Ile Leu Phe Glu Val Pro Glu Val Thr Val Ala Pro Val
                85                  90                  95 cac att tgt acc agc tgg gag tcc gcc tct ggt atc gtt gag ttc tgg     336
His Ile Cys Thr Ser Trp Glu Ser Ala Ser Gly Ile Val Glu Phe Trp
            100                 105                 110 gta gat ggt aaa ccg cgc gtg cgt aag tcc ctg aag aaa ggc tac act     384
Val Asp Gly Lys Pro Arg Val Arg Lys Ser Leu Lys Lys Gly Tyr Thr
        115                 120                 125 gtg ggc gca gaa gcg agc atc atc ttg ggt cag gaa cag gat tcc ttc     432
Val Gly Ala Glu Ala Ser Ile Ile Leu Gly Gln Glu Gln Asp Ser Phe
    130                 135                 140 ggt ggc aac ttt gaa ggt agc cag tcc ctg gtt ggt gac att ggc aat     480
Gly Gly Asn Phe Glu Gly Ser Gln Ser Leu Val Gly Asp Ile Gly Asn
145                 150                 155                 160 gtg aac atg tgg gac ttt gtg ctg tca cca gat gaa att aac acc atc     528
Val Asn Met Trp Asp Phe Val Leu Ser Pro Asp Glu Ile Asn Thr Ile
                165                 170                 175 tat ctt ggc ggt ccg ttc agt cct aat gtc ctg aac tgg cgt gca ctg     576
Tyr Leu Gly Gly Pro Phe Ser Pro Asn Val Leu Asn Trp Arg Ala Leu
            180                 185                 190 aag tat gaa gtg caa ggc gaa gtg ttc acc aaa ccg cag ctg tgg ccg     624
Lys Tyr Glu Val Gln Gly Glu Val Phe Thr Lys Pro Gln Leu Trp Pro
        195                 200                 205 ctc gag                                                             630
Leu Glu
    210
```

<210> SEQ ID NO 110
<211> LENGTH: 210
<212> TYPE: PRT
<213> ORGANISM: Homo sapiens

<400> SEQUENCE: 110

Gly Ser Gln Thr Asp Met Ser Arg Lys Ala Phe Val Phe Pro Lys Glu

```
1               5                   10                  15
Ser Asp Thr Ser Tyr Val Ser Leu Lys Ala Pro Leu Thr Lys Pro Leu
                20                  25                  30

Lys Ala Phe Thr Val Cys Leu His Phe Tyr Thr Glu Leu Ser Ser Thr
                35              40                  45

Arg Gly Tyr Ser Ile Phe Ser Tyr Ala Thr Lys Arg Gln Asp Asn Glu
            50              55                  60

Ile Leu Ile Phe Trp Ser Lys Asp Ile Gly Tyr Ser Phe Thr Val Gly
 65                 70                  75                  80

Gly Ser Glu Ile Leu Phe Glu Val Pro Glu Val Thr Val Ala Pro Val
                85                  90                  95

His Ile Cys Thr Ser Trp Glu Ser Ala Ser Gly Ile Val Glu Phe Trp
                100                 105                 110

Val Asp Gly Lys Pro Arg Val Arg Lys Ser Leu Lys Lys Gly Tyr Thr
                115                 120                 125

Val Gly Ala Glu Ala Ser Ile Ile Leu Gly Gln Glu Gln Asp Ser Phe
                130                 135                 140

Gly Gly Asn Phe Glu Gly Ser Gln Ser Leu Val Gly Asp Ile Gly Asn
145                 150                 155                 160

Val Asn Met Trp Asp Phe Val Leu Ser Pro Asp Glu Ile Asn Thr Ile
                165                 170                 175

Tyr Leu Gly Gly Pro Phe Ser Pro Asn Val Leu Asn Trp Arg Ala Leu
                180                 185                 190

Lys Tyr Glu Val Gln Gly Glu Val Phe Thr Lys Pro Gln Leu Trp Pro
                195                 200                 205

Leu Glu
    210

<210> SEQ ID NO 111
<211> LENGTH: 26
<212> TYPE: DNA
<213> ORGANISM: Artificial
<220> FEATURE:
<223> OTHER INFORMATION: Primer B-Syn4A-C1-f

<400> SEQUENCE: 111
ggatccatca tcaacacctt ctacgc                                        26

<210> SEQ ID NO 112
<211> LENGTH: 25
<212> TYPE: DNA
<213> ORGANISM: Artificial
<220> FEATURE:
<223> OTHER INFORMATION: Primer B-Syn4A-C1-rn

<400> SEQUENCE: 112
ggatcctgcc ggcacattca tgatt                                         25
```

PROTEIN PRODUCTION METHOD, FUSION PROTEIN, AND ANTISERUM

TECHNICAL FIELD

The present invention relates to a method for production of proteins, in particular to a method for production of heterologous proteins using bacteria as a host, and more specifically a highly efficient method for production of heterologous proteins performed by utilizing the characteristic properties of Cry proteins, the proteins formed by *Bacillus thuringiensis*. The present invention further relates to fusion proteins produced by the method, antiserum and antibodies to such fusion proteins, and reagents containing them, as well as a method for analysis.

BACKGROUND ART

As for production of proteins/enzymes, i.e., major components of various biological products, simple, easy and low-cost methods for their production have been sought, such as introduction of their genes, if they are isolated, into microorganisms, like *E. coli*, and letting the proteins/enzymes be expressed and accumulate in them. However, there are also many cases in which attempts fail to let a heterologous protein express/accumulate in the cells of microorganisms. The cause of such failures becomes particularly notable when higher production efficiency is sought. That is, the heterologous protein biosynthesized in the cells of a microorganism, which accumulates forming insoluble inclusion bodies, gets inactivated in the process. Generally, it is very difficult to solubilize such insoluble inclusion bodies of a protein and restoring the biological activity of the protein.

Further, in the case where the heterologous protein to be produced has a cytotoxicity, accumulation of that toxic protein adversely affects the proliferation/survival of the very host cells, resulting in lowered production yield, and further, in death of the host cells.

Due to these drawbacks, production of proteins/enzymes, which are major components of various biological products, often has to rely on time-consuming and costly methods, such as utilizing the living organisms that intrinsically produce the protein/enzyme. There seems to be not a small number of cases in which these drawbacks form a factor that hindering development of an efficient method of their industrial production, and this is one of the problems to be solved.

On the other hand, insecticidal proteins produced by an aerobic soil bacterium, *Bacillus thuringiensis*, has long been known (see as a review e.g., Non-patent Document 1). During its sporulation, *Bacillus thuringiensis* also produces, separately from spores, generally a single large parasporal inclusion body consisting mainly of a crystal protein (this is called "Cry protein"). Cry proteins consist of about 1000-1200 amino acids, and many of them are known to be produced by various *Bacillus thuringiensis* strains. About half of them have been found to have an insecticidal activity specific to certain insects, and some of those strains which produce a Cry protein having such an activity have been widely used as BT insecticides. When ingested by larvae of respective target insects, each of those Cry proteins which have an insecticidal activity undergoes cleavage by the digestive fluid at a predetermined position of its amino acid sequence and thus a peptide on its C-terminus side (consisting about 400-500 amino acids: abbreviated to "Cter") is removed, leaving behind a peptide on the N-terminus side (NB: a short peptide at the N-terminus is also removed), which exhibits a potent insecticidal activity. For example, in the case of a protein named Cry4Aa, an N-terminus region consisting of Met 1 to Gln695 (in particular, a peptide left behind after Met1 to Try57 are removed) of its entire amino acid sequence acts as the very insecticidal component on its target insects (*Culex pipiens pallens* and the like). Its Cter, which consists of an amino acid sequence starting with Ile696 and is deleted by cleavage, is unnecessary part for the insecticidal activity (see Non-Patent Document 2). And, as for a protein known as Cry1Aa, which is an insecticidal specific to lepidopteran insects (butterflies and moths), the region consisting of Met1 to Lys621 on the N terminal side of its amino acid sequence (in particular, the part of the region left behind after further removal of Met1 to Arg28) works as the very insecticidal component, and its Cter, which consists of an amino acid sequence starting with Ala622, is deleted by cleavage (Non-Patent Document 3). Furthermore, as to Cry1Ac, which is also an insecticidal toxin specific to Lepidopteran insects (butterflies and moths) like Cry1Aa, its very insecticidal component consists of Met1 to Lys623 (in particular, the part of the region left behind after removal of Met1 to Arg28) of its amino acid sequence, and its Cter, which is located on the C-terminal side and consists of amino acid sequence starting with Ala624, does not take part in the generation of insecticidal activity, but is removed by cleavage by the action of the digestive fluid in the larvae (Non-Patent Document 4). Further, in recent years, Cry proteins have been found with which no insecticidal activity is as yet known, and some of them are found to specifically destroy human cancer cells, some specifically kill *Tricomonas vaginalis*, the pathogen protozoa causing human tricomonasis, and some exhibit a potent worm-killing activity to Nematoda. Though they differ in their biological activity and in their targets at which they exhibit toxic effects, the Cry proteins have a common characteristic property that they occur within *Bacillus thuringiensis* cells in the form of a large parasporal inclusion body.

[Non-Patent Document 1] M. Ohba, H. Hori and H. Sakai, "*Bacillus thuringiensis*: Science of Insecticidal Proteins", Industrial Publishing & Consulting, Inc., Feb. 28, 2005.

[Non-Patent Document 2] M. Yamagiwa et al., Appl. Environ. Microbiol. 65: 3464-3469 (1999)

[Non-Patent Document 3] P. Grochulski et al., J. Mol. Biol. 254: 447-464 (1995)

[Non-Patent Document 4] J. N. Aronson and H. C. Arvidson, Appl. Environ. Microbiol. 53: 416-421 (1999)

DISCLOSURE OF THE INVENTION

Problem to be Solved by the Invention

Against the above background, the objective of the present invention is to provide a method for production of heterologous proteins/enzymes utilizing microorganisms, with improved efficiency compared with conventional methods.

Means to Solve the Problem

The present inventors found that when brought to express in host bacterium cells, such as *E. coli* cells, a fusion protein consisting of the Cter of one of the Cry proteins and some other protein which was fused with it, an insoluble inclusion bodies containing the fusion protein (hereinafter referred to as a "crystal") formed in the cells, and thus this heterologous protein accumulated in a great amount in the cells, and that those crystals had following excellent properties distinguished from those of other insoluble inclusion bodies so far known:

a. that the heterologous protein/enzyme has been contained in the crystals, with its biological activities kept intact, b. that crystals are efficiently solubilized in an alkaline buffer solution with a pH of 10-11, c. that after solubilized, the heterologous protein/enzyme can be easily recovered in the supernatant, with its biological activities kept intact, d. that even a cytotoxic heterologous protein can be efficiently produced through crystal formation, and e. that crystals can be stored as they are for a long time, with their stability being kept uncompromised.

The present inventors further found that the full-length Cter is not indispensable for such crystals to be formed, but a part consisting of some 140-160 amino acids on its N-terminal side suffices. In particular, examination was performed, based on 4AaCter(696-851) of Cry4Aa2, which is a Cter's N-terminal ⅓-long fragment and with which it was first discovered that a fusion protein consisting of it and some other protein forms crystals, and by selecting fragments of various other Cter's amino acid sequences according to their similarity to the former fragment based on the alignment technique. As a result, formation of similar crystals was found with them. It was also found that an antiserum which is created by immunizing an animal with a fusion protein obtained according to the present invention is reactive with the original protein, i.e., the protein prior to fused with the Cter employed. The present invention has been completed through further studies on the basis of these findings.

Thus, the present invention provides what follows:

1. A method for production of a protein (A) in the form of a fusion protein, comprising the steps of (a) preparing a DNA which codes for a fusion protein comprising the peptide chain forming the protein (A) and other peptide chain (B), on the N- or C-terminal side of the latter the former being combined, wherein the peptide chain (B) is a C-terminal peptide chain included in the amino acid sequence of one of the Cry proteins produced by *Bacillus thuringiensis* listed in Table 1 or 2 and including in itself a corresponding partial sequence identified in the tables,

TABLE 2

| Cry proteins | C-terminal peptide, and Partial sequence(SEQ ID NO:) |
|---|---|
| Cry4Aa1(SEQ ID NO: 88), Cry4Aa2(SEQ ID NO: 89), Cry4Aa3(SEQ ID NO: 90) | C-terminal peptide: the part starting from Ile696<br>Partial sequence: Ile696-Pro851 (SEQ ID NO: 6) or Ile801-Ser829 (SEQ ID NO: 7) |
| Cry4Ba1(SEQ ID NO: 91), Cry4Ba2(SEQ ID NO: 92), Cry4Ba5(SEQ ID NO: 93) | C-terminal peptide: the part starting from Val652<br>Partial sequence: Val652-Pro807 (SEQ ID NO: 8) or Ile757-Ser785 (SEQ ID NO: 9) |
| Cry4Ba4(SEQ ID NO: 94) | C-terminal peptide: the part starting from Val651<br>Partial sequence: Val651-Pro806 (SEQ ID NO: 10) or Ile756-Ser784 (SEQ ID NO: 11) |
| Cry4Ba3(SEQ ID NO: 95) | C-terminal peptide: the part starting from Val652<br>Partial sequence: Val652-Pro807 (SEQ ID NO: 12) or Ile756-Ser784 (SEQ ID NO: 13) |
| Cry8Ca1(SEQ ID NO: 96) | C-terminal peptide: the part starting from Lys672<br>Partial sequence: Lys672-Pro829 (SEQ ID NO: 14) |

(b) introducing the DNA into a host bacterium to transform the same, and (c) allowing the fusion protein to be expressed in the host bacterium which has been transformed.

2. The method for production according to 1 above, wherein in the step of preparing the DNA which codes for a fusion protein comprising the peptide chain forming the protein (A) and the other peptide chain (B), on the N- or C-terminal side of the latter the former being combined, a DNA coding for an amino acid sequence which provides a specific cleavage site for a proteolytic enzyme is interposed between the DNA which codes for the peptide chain forming protein (A) and the DNA which codes for the peptide chain (B).

TABLE 1

| Cry proteins | C-terminal peptide, and partial sequence (SEQ ID NO:) |
|---|---|
| Cry1Aa1(SEQ ID NO: 50), Cry1Aa2(SEQ ID NO: 51), Cry1Aa3(SEQ ID NO: 52), Cry1Aa4(SEQ ID NO: 53), Cry1Aa5(SEQ ID NO: 54), Cry1Aa8(SEQ ID NO: 55), Cry1Aa9(SEQ ID NO: 56), Cry1Aa10(SEQ ID NO: 57), Cry1Aa11(SEQ ID NO: 58), Cry1Aa12(SEQ ID NO: 59), Cry1Aa13(SEQ ID NO: 60), Cry1Aa14(SEQ ID NO: 61) | C-terminal peptide: the part starting from Ala622<br>Partial sequence: Ala622-Pro777 (SEQ ID NO: 1) |
| Cry1Ab3(SEQ ID NO: 62), Cry1Ab4(SEQ ID NO: 63), Cry1Ab8(SEQ ID NO: 64), Cry1Ab9(SEQ ID NO: 65), Cry1Ab10(SEQ ID NO: 66), Cry1Ab12(SEQ ID NO: 67), Cry1Ab13(SEQ ID NO: 68), Cry1Ab15(SEQ ID NO: 69), Cry1Ab16(SEQ ID NO: 70), Cry1Ab17(SEQ ID NO: 71), Cry1Ab21(SEQ ID NO: 72) | C-terminal peptide: the part starting from Ala623<br>Partial sequence: Ala623-Pro778 (SEQ ID NO: 2) |
| Cry1Ab2(SEQ ID NO: 73) | C-terminal peptide: the part starting from Ala624<br>Partial sequence: Ala624-Pro779 (SEQ ID NO: 3) |
| Cry1Ac1(SEQ ID NO: 74), Cry1Ac4(SEQ ID NO: 75), Cry1Ac7(SEQ ID NO: 76), Cry1Ac8(SEQ ID NO: 77), Cry1Ac9(SEQ ID NO: 78), Cry1Ac10(SEQ ID NO: 79), Cry1Ac11(SEQ ID NO: 80), Cry1Ac16(SEQ ID NO: 81), Cry1Ac19(SEQ ID NO: 82) | C-terminal peptide: the part starting from Ala624<br>Partial sequence: Ala624-Pro779 (SEQ ID NO: 4) |
| Cry1Ac5(SEQ ID NO: 83), Cry1Ac12(SEQ ID NO: 84), Cry1Ac14(SEQ ID NO: 85), Cry1Ac15(SEQ ID NO: 86), Cry1Ac20(SEQ ID NO: 87) | C-terminal peptide: the part starting from Ala623<br>Partial sequence: Ala623-Pro778 (SEQ ID NO: 5) |

3. The method for production according to 1 or 2 above comprising a further step of fracturing the host bacterium containing the fusion protein thus expressed to collect the fusion protein.

4. The method for production according to 3 above comprising a further step of purifying the collected fusion protein through solubilization of the same in an alkaline aqueous solution.

5. The method for production of the protein (A) comprising a step of removing the peptide chain (B) from the fusion protein obtained according to 4 above.

6. The method for production according to 5 above, wherein the removal of the peptide chain (B) is done by treating a specific cleavage site for a proteolytic enzyme, which the fusion protein has between the peptide chain forming the protein (A) and peptide chain (B), with the proteolytic enzyme.

7. A fusion protein produced by the method according to 3 or 4 above.

8. An antiserum reactive to the protein (A) which antiserum is obtained by immunizing a mammalian animal with the fusion protein according to 7 above, and then collecting the serum of the animal.

9. The antiserum according to 7 or 8 above, wherein the protein (A) is C-reactive protein.

10. An antibody to the protein (A) isolated from the antiserum according to 8 or 9 above.

11. A testing reagent comprising the antiserum according to 8 or 9 above.

12. A testing reagent comprising the antibody according to 10 above.

13. A method for analysis of a sample for protein (A), comprising the steps of bringing the sample into contact with the antiserum according to 8 above, or the antibody according to 9 above, to form an antigen-antibody complex, and detecting the antigen-antibody complex.

14. The method according to 13 above, wherein the protein (A) is C-reactive protein.

Effect of the Invention

According to the present invention, utilizing a bacterium, such as *E. coli*, as a host, a heterologous protein can be produced in the form of a fusion protein in a great amount within the cells of the bacterium, in the form of insoluble crystals, maintaining (but in a potential manner) activities of the original protein. As these insoluble crystals, in the situation where they are, do not exhibit the activities of the original heterologous protein in the host bacterium, even proteins otherwise harmful or lethal to the host can be produced in a large scale. Furthermore, the crystals can be easily isolated, and then solubilized in an alkaline condition, collected and purified. The solubilized fusion protein has the activities of the original, heterologous protein, and further it is also possible to readily recover the original heterologous protein through removal, by any of proper methods, of the portion which has been derived from the Cter employed. Therefore, the present invention enables production of heterologous proteins utilizing a bacterium, such as *E. coli*, as a host, with dramatically improved efficiency.

Furthermore, the present invention also enables to obtain, in a large amount, even such proteins as have been obtainable so far only in a trace amount, in the form in which the proteins are fused to a C-terminal peptide chain of a Cry protein. Thus, it makes it easier to obtain antisera to original proteins, through immunization of mammalian animals (e.g., rabbit, goat) with their fusion proteins and collection of the sera.

Such antisera can be used, e.g., as testing reagents, for detection or measurement of the original proteins in given samples (e.g., a biological sample such as body tissues, blood, plasma, or serum). Further, antibodies (polyclonal antibodies) to the original proteins can also be isolated from such antisera, and can be used for the same purpose.

BRIEF DESCRIPTION OF DRAWINGS

FIG. 1 illustrates the primer sets used for preparation of synthetic DNAs which then were used for construction of the gene coding for 4AaCter (696-851) by repetitive PCR. The following primers were used:
C1-1-f (SEQ ID NO: 15), C1-1&2-r (SEQ ID NO: 16), C1-2&3-f (SEQ ID NO: 17), C1-3&4-r (SEQ ID NO: 18), C1-4&5-f (SEQ ID NO: 19), C1-5&6-r (SEQ ID NO: 20), C1-6&7-f (SEQ ID NO: 21), C1-7&8-r (SEQ ID NO: 22), C1-8&9-f (SEQ ID NO: 23) and C1-9-r (SEQ ID NO: 24).

BEST MODE FOR CARRYING OUT THE INVENTION

Figure 2:
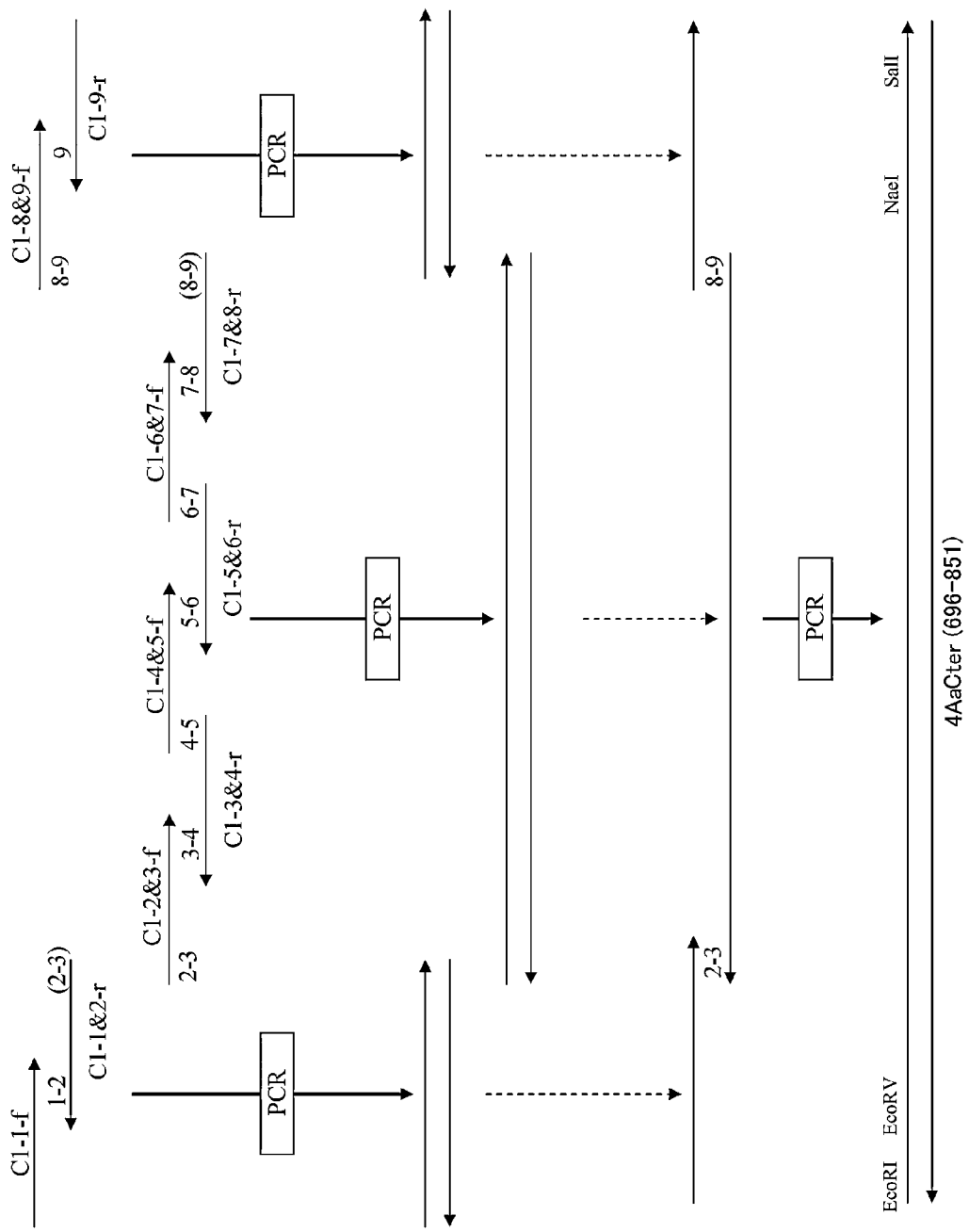
FIG. 2 is a schematic illustration of the process for construction of the DNA coding for the entire 4AaCter(696-851) by repetitive PCR.

In the present specification, amino acid numbers are determined by assigning "1" to the methionine (Met) residue corresponds to the start codon in the original Cry protein.

The ability of a fusion protein to form crystals is thought to be the property that is common to the Cter region of the Cry proteins, which are characterized by formation of a large parasporal inclusion body, for as shown in the Examination section, crystal formation was alike confirmed in the experiments employing combinations of different Cter's and different heterologous proteins, and since the structure of Cter's are highly conserved among insecticidal toxins.

A large number of Cry proteins are known (*Bacillus thuringiensis* Toxin Nomenclature: http://www.lifesci.sussex.ac.uk/home/Neil_Crickmore/Bt/). Of the full-length amino acid sequence of a Cry protein, the N-terminal side portion which determines such biological activities as an insecticidal activity, is not needed for the purpose of the present invention, and therefore the remaining portion, the C-terminal peptide (Cter), may be utilized for formation of fusion proteins with the protein of interest. Further, in utilizing a Cter, full length of it is not necessary, but its N-terminal part consisting of about 140-160 amino acids suffices, and its fragments may also be used.

As to Cry4Aa1, Cry4Aa2 and Cry4Aa3 (Cry4Aa group), for example, which have in common the identical partial sequence Ile696-Pro851 (SEQ ID NO:6) inside the Cter, the portion starting from Ile696, it has been confirmed that a fusion protein consisting of the peptide having this partial sequence and a heterologous protein forms crystals (cf. Examples). Further, among various other partial sequences included inside this partial sequence, the sequence Ile801-Ser829 (SEQ ID NO:7) and some other partial sequences including this within themselves also provided peptides which gave, in combination with a heterologous protein, such a fusion proteins that formed crystals, whereas partial sequences including no Ile801-Ser829 within themselves failed to form crystals (Examples). Therefore, Ile801-Ser829 (SEQ ID NO:7) is considered to be the very sequence that confers fusion proteins the ability to form crystals. Thus, Cter's partial sequences which include this sequence in themselves can be used to form fusion proteins with heterologous proteins so as to confer the latter the ability to form crystals.

Furthermore, Cry4Ba1, Cry4Ba2 and Cry4Ba5 share a completely identical partial amino acid sequence Val652-Pro807 (SEQ ID NO:8), which corresponds to the above-mentioned Cter fragment Ile696-Pro851 of Cry4Aa1, and, further, all of them include a sequence (Ile757-Ser785, SEQ ID NO:9) within themselves which is completely identical to Ile801-Ser829 (SEQ ID NO:7) of Cry4Aa1. Therefore, as to Cry4Ba1, Cry4Ba2 and Cry4Ba5, either their Cter themselves (the portion starting from Val652) or their Cter's partial sequences which include Ile757-Ser785 within themselves can be used as desired for the purpose of the present invention.

As to Cry4Ba4, a partial sequence Val651-Pro806 (SEQ ID NO:10) within its Cter (the portion stating from Val651), which corresponds to the above-mentioned Cter fragment Ile696-Pro851 of Cry4Aa1, is completely identical to the partial amino acid sequence Val652-Pro807 of Cry4Ba1, Cry4Ba2 and Cry4Ba5, and they differ only in their starting region in their respective Cry proteins. Therefore, again, Cry4Ba4 includes within itself a sequence (Ile756-Ser784, SEQ ID NO:11) that is the same as Ile801-Ser829 (SEQ ID NO:7) of Cry4Aa1. Thus, as to Cry4Ba4 also, either its Cter itself (the portion starting from Val651) or any of its fragments which includes Ile756-Ser784 within itself can be used as desired for the purpose of the present invention.

As to Cry4Ba3, a partial sequence Val652-Pro807 (SEQ ID NO:12) within its Cter (the portion starting from Val652), which corresponds to the above-mentioned Cter fragment le696-Pro851 of Cry4Aa1, also includes within itself a sequence (Ile757-Ser785, SEQ ID NO: 13) which is completely identical to Ile801-Ser829 (SEQ ID NO:7) of Cry4Aa1. Therefore, as to Cry4Ba3, too, either its Cter (the portion starting from Val652) itself or any of its fragments which includes Ile757-Ser785 within itself can be used as desired for the purpose of the present invention.

As for the Cry1Aa group including e.g., Cry1Aa1 as shown in the above table, their Cter's are the portions all starting from Ala622, among which their partial sequences Ala622-Pro777 are completely identical with one another in their amino acids. A fusion protein of the peptide consisting of this identical portion and a heterologous protein was confirmed to form crystals (see Example in which a peptide originating from Cry1Aa3 is utilized). Therefore, as regards the Cry1Aa group, either their Cter's (the portion starting from Ala622) themselves or any of their fragments which includes Ala622-Pro777 within itself can be used as desired in the present invention.

Regarding the CryAb group including e.g., Cry1Ab3 (but except Cry1Ab2) as shown in the above table, their Cter's are the portions all starting from Ala623, among which their partial sequence Ala623-Pro778, which correspond to the above-mentioned Cter fragment Ile696-Pro851 of Cry4Aa1, are completely identical with one another in their amino acids. And this partial sequence, when compared with the partial sequence Ala622-Pro777 of the Cter's of the above Cry1Aa group, differs only in that the Gln664 in the Cry1Aa group is replaced with 665Lys in the CryAb group, and has no other difference except that the amino acid position numbers in the former partial sequence as a whole are greater by 1 than the latter. As the proteins belonging to the CryAb group are those which form a parasporal inclusion bodies and the partial sequence Ala623-Pro778 or their Cter's differ only in one single amino acid compared with the partial sequence Ala622-Pro777 of the Cter of the Cry1Aa group (with which formation of crystals is confirmed in Example), either the Cter's of the CryAb group (the portion starting from Ala623) themselves or any of their fragments which include Ala623-Pro778 within themselves can be used as desired in the present invention.

The Cter of Cry1Ab2 is the portion which starts from Ala624, and an amino acid sequence Ala624-Pro779 included within it differs only in that Ser703 and Asp712 of the Cry1Ab group are replaced in it with Asn704 and His713, respectively, and has no other difference except that its amino acid position numbers as a whole are shifted by 1. For this reason, and since Cry1Ab2 is a protein which forms parasporal inclusion bodies, either the Cter of this (the portion starting from Ala624) itself or any of its fragments which include Ala624-Pro779 within themselves can be used as desired in the present invention.

In the above tables, the group consisting of Cry1Ac1, Cry1Ac4, Cry1Ac7, Cry1Ac8, Cry1Ac9, Cry1Ac10, Cry1Ac11, Cry1Ac16 and Cry1Ac19 (Cry1Ac(I) group) have their Cter's which start from Ala624, and the group consisting of Cry1Ac5, Cry1Ac12, Cry1Ac14, Cry1Ac15, and Cry1Ac20 (Cry1Ac(II) group) have their Cter's which start from Ala623. And the partial sequence Ala624-Pro779 of the former is completely identical in their amino acids to the partial sequence Ala623-Pro778 of the latter. Judging from the fact that a fusion protein of the peptide consisting of the partial sequence Ala624-Pro779 of Cry1Ac1 and a heterologous protein was confirmed to form crystals (see Examples), also with the Cry1Ac(I) and Cry1Ac(II) groups, either their Cter's themselves or any of the fragments of the Cter which include the partial sequence Ala624-Pro779 for the Cry1Ac(I) group or the partial sequence Ala623-Pro778 for the Cry1Ac(II) group, can be used in the present invention.

In the present invention, the DNA coding for the fusion protein consisting a protein of interest and a Cter (or its fragment) is prepared by combining a DNA coding for the Cter or its fragment mentioned above is combined in-frame with a DNA coding for the protein of interest on its 3' or 5' end.

In the present invention, by employing as a template the total DNA of a *Bacillus thuringiensis* strain which has the gene of a particular Cry protein that is to be utilized, a DNA coding for the Cter (or its fragment) of the protein can be prepared by PCR. In this preparation process, the primers employed may be provided with restriction sites by a conventional method for incorporation into an expression vector. In the case where the template total DNA of the *Bacillus thuringiensis* strain needed is unavailable, the DNA region of interest may be synthesized by first preparing primer DNAs (50-60 basis at longest), several to about 10 in number, that cover the entire region of the Cter (or its fragment) by a conventional method based on publicized/registered (e.g., at DDBJ) information of that gene's nucleotide sequence/amino acid sequences, and then carrying out a recursive PCR using the primer DNAs.

The technique of recursive PCR is well known to those skilled in the art. Synthesis of the DNA by this method for the region of Cter (or its fragment) may be carried out in the following manner, by way of example, 4AaCter(696-851) [Ile696-Pro851 in the Cry4Aa group]: the nucleotide sequence coding for 4AaCter(696-851) is divided into 10 portions and each portion is chemically synthesized as primers (FIG. 1), in such a manner as leaving complementary bases at its end(s) for permitting its hybridization with adjacent portion(s) at their ends, and using these, a recursive PCR is carried out to obtain the DNA coding for the full-length 4AaCter (696-851). In the nucleotide sequences presented in FIG. 1, the bases shown by upper-case letters are those located within the nucleotide sequence coding for 4AaCter (696-851), and the bases shown by lower-case letters are those which were added for convenience in manipulation.

(1) Primer C1-1-f (SEQ ID NO:15)
(2) Primer C1-1&2-r (SEQ ID NO:16)
(3) Primer C1-2&3-f (SEQ ID NO:17)
(4) Primer C1-3&4-r (SEQ ID NO:18)
(5) Primer C1-4&5-f (SEQ ID NO:19)
(6) Primer C1-5&6-r (SEQ ID NO:20)
(7) Primer C1-6&7-f (SEQ ID NO:21)
(8) Primer C1-7&8-r (SEQ ID NO:22)
(9) Primer C1-8&9-f (SEQ ID NO:23)
(10) Primer C1-9-r (SEQ ID NO:24)

A DNA fragment prepared by PCR using a pair of primers C1-1-f and C1-1&2r, which had at one end of them sequences complementary with each other, and a DNA fragment having at both ends respective complementary sequences and prepared by PCR using a series of primer pairs, C1-2&3-f, C1-3&4-r, C1-4&5f, C1-5&6-r, C1-6&7-f and C1-7&8-r, and a DNA fragment prepared by PCR using a pair of primers C1-8&9-f and C1-9r were provided. Using these fragments, the DNA (SEQ ID NO:25) coding for the full-length 4AaCter (696-851) is prepared by PCR (FIG. 2).

It is also possible, in order to introduce a spacer which gives an amino acid sequence that can be cleaved specifically by an enzyme (e.g., an amino acid sequence targeted by a protease) between the heterologous protein of interest and the Cter (or its fragment), to introduce in advance a DNA coding for such a spacer. Insertion of such a DNA can be done by choosing a proper nucleotide sequence for the primers, which is also well known to those skilled in the art.

When the gene prepared as above is introduced into a host bacterium, such as E. coli, and the host is induced to express the fusion protein, the fusion protein accumulates within the host cells in a great amount forming crystals. Crystals thus formed can be readily observed under an optical microscope.

Through fracturing the host cells obtained above which have a large amount of accumulated crystals, and centrifugation which follows, the crystals can be collected as the precipitate. The crystals thus collected can be dissolved by suspending them in an alkaline aqueous solution, e.g., sodium a carbonate buffer with a pH of about 10.5-12 and incubating the mixture at 37° C. for 30 minutes to 2 hours. After dissolution of the crystals, the fusion protein, which retains the biological activity is recovered in the supernatant by centrifugation.

Depending on the intended purpose, the active fusion protein recovered above may be used directly, or subjected to further purification by commonly used purification means, such as ion-exchange chromatography, as needed.

Further, if a site which is cleaved specifically by an enzyme is inserted between the heterologous protein and Cter (or its fragment), treatment of the fusion protein with the enzyme to cleave it at the sequence, followed by removal of the Cter portion (or its fragment), will give the protein of interest.

In order to produce it in the form of a fusion protein in host cells, the molecular weight of a heterologous protein fused with a Cter (or its fragment) of a Cry protein is preferably not more than 50 kDa.

In a convenient way, detection of a fusion protein obtained by the method according to the present invention can be done by detecting the Cter portion of the fusion protein using an anti-Cter antiserum (or an anti-Cter antibody isolated from the antiserum) collected from an animal (in particular, mammal, e.g., rabbit, goat, etc.) which has been immunized with the Cter used in the fusion protein formation according to a conventional method (Example 8). For detection, any method well known to those skilled in the art may be employed, such as Western blotting, ELISA, immunoprecipitation, and the like. A column prepared by immobilizing an antiserum to the Cter or an anti-Cter antibody on a solid phase may also be used for isolation and purification of a fusion protein.

Further, an antiserum reactive to the original protein before fusion can also be obtained by immunizing an animal in a conventional manner with the fusion protein prepared according to the present invention, and collecting the serum (see Example 7). Such an antiserum or an antibody (polyclonal) to the original protein isolated from the antiserum, can be used in the analysis (detection, semiquantitative or quantitative) of a sample (e.g., a biological sample of an animal, esp. of a mammal, among others, human tissues, blood, plasma and serum). Specifically, for example, such an antiserum or antibody is immobilized on a proper carrier, like as latex particles, gelatin particles, colloidal gold, polystyrene beads, or a polystyrene plate. And any of techniques well known to those skilled in the art, such as immunoagglutination, enzyme labeling, chemiluminescence, and the like, can be performed on them for detection of the presence of the original protein contained in a sample, or for semiquantitative or quantitative analysis through comparison with a reference standard. Thus, an antiserum to the original protein (or an antibody to the original protein) obtained from an animal immunized with a fusion protein can be provided as a testing reagent, directly in the form of a solution or a lyophilized preparation, or in such forms in which it is immobilized on a proper carrier, like latex particles, gelatin particles, colloidal gold, polystyrene beads, a polystyrene plate, and the like.

Isolation and purification of the antibody to the original protein from the antiserum to the fusion protein can be done, in a conventional manner, i.e., by preparing an affinity column to which the original protein or the Cter employed in the fusion is bound, and by allowing the antibody to the original protein or the antibody to the Cter, respectively, to be specifically adsorbed.

EXAMPLES

The present invention is described in further detail below. It should be noted, however, that the present invention is not intended to be limited to the examples.

Example 1

Production of Fusion Protein of 4AaCter(696-851) and Glutathione-S-transferase

According to the following procedure, glutathione-S-transferase (GST) originating from *Schistosoma japonicum* was expressed in a large amount and was let accumulate in *E. coli* cells, in the form of a fusion protein with 4AaCter (696-851), which is a fragment of the Cter of one of Cry proteins, Cry4Aa2, and corresponds to amino acids Ile 698~Pro 851 of Cry4Aa2.

Figures 3, 4:
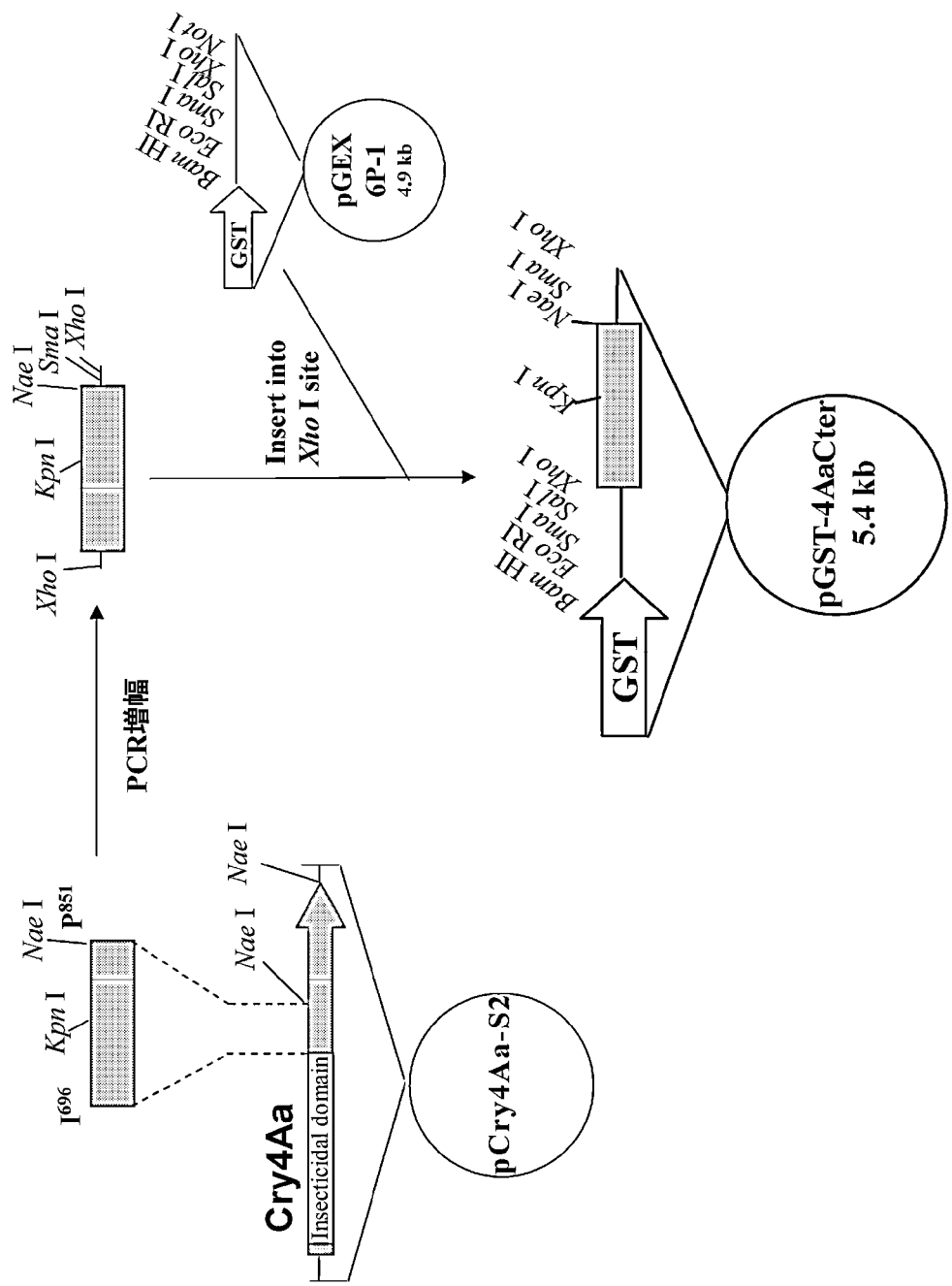
FIG. 3 illustrates the order of combination of GST and 4AaCter (696-851) in their fusion protein.
FIG. 4 is a schematic diagram illustrating the flow of the steps from the construction of the DNA coding for 4AaCter (696-851) up to the construction of an expression vector for the fusion protein.

1. Preparation of a DNA Coding for 4AaCter(696-851) (FIG. 4)

Figures 5, 6:
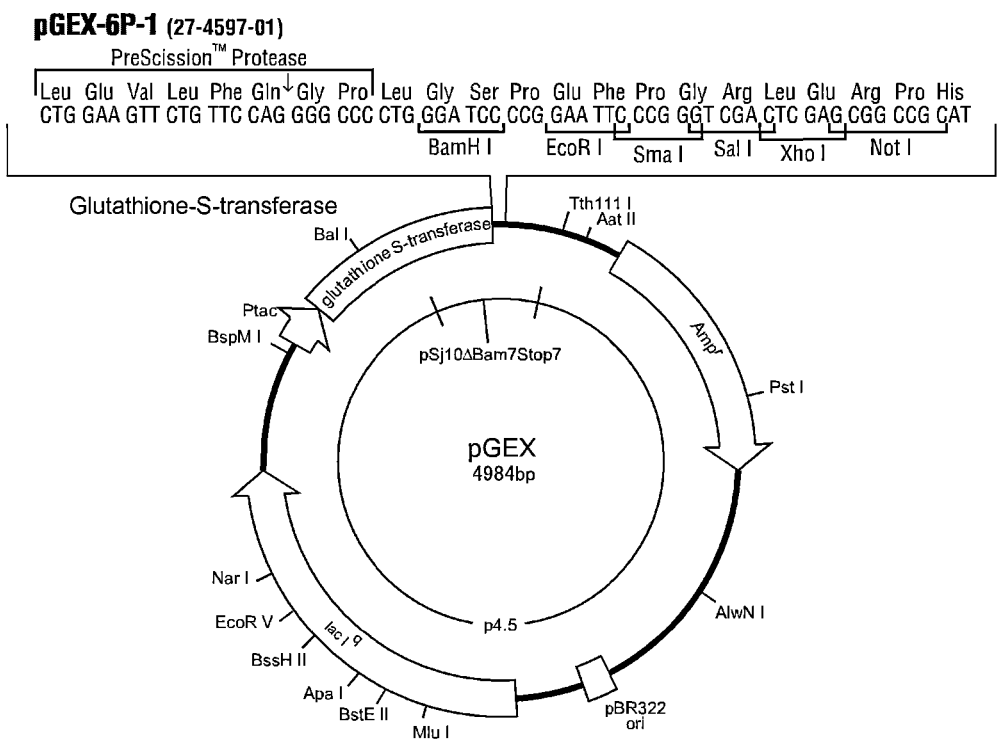
FIG. 5 illustrates the primer pair which was employed to amplify the DNA fragment coding for 4AaCter(696-851). The following primers were used: X-Syn4A-C1-f (SEQ ID NO: 27) and X—S-Syn4A-C1-r (SEQ ID NO: 28).
FIG. 6 illustrates a map of expression vector pGEX-6P-1. Shown are the nucleic acid and amino acid sequences in the pGEX-6P-1 cloning site (SEQ ID NO: 29 and SEQ ID NO: 30, respectively).

Cry4Aa-S2 gene (formally named, in the priority document, syn4A gene) (which is a gene designed to express a polypeptide consisting of the full-length Cry4Aa's 1180 amino acids) was synthesized by recursive PCR. For this total synthesis, 50 to 55-base synthetic oligonucleotide primers were used which had been designed to cover the full-length nucleotide sequence of interest and at the same time to form base pairs consisting of 10 to 15 bases overlapping between adjacent ones of these primers. The nucleotide sequence of the open reading frame (ORF) of cry4Aa-S2 gene is shown as SEQ ID NO:26. Using this as a template, PCR was carried out to amplify the DNA fragment coding for 4AaCter(696-851). The nucleotide sequences of the primers employed are shown in FIG. 5 and below. The DNA fragment obtained by this has a XhoI site at its each end.

(1) Primer X-Syn4A-C1-f: 5'-GGCTCGAGATCATCAA-CACCTTCTAC-3' [nucleotides 3-26 (single-underscored in the upper part of FIG. 5) give an XhoI site, nucleotide 9-26 (double-underscored) a terminal sequence of 4AaCter(696-851)] (SEQ ID NO:27).

(2) Primer X-S-Syn4A-C1-r: 5'-GGCTCGAGC-CCGGGCCGGCACATTCATGATT-3' [nucleotides 3-8 (single-underscored in the lower part of FIG. 5) give an XhoI site, nucleotide 17-31 (double-underscored) a terminal sequence of 4AaCter(696-851)] (SEQ ID NO:28).

<Reaction Solution>

| | |
|---|---|
| 10 × PCR buffer (for KOD plus) | 5.0 µL |
| 2 mM dNTP | 5.0 µL |
| 25 mM MgSO$_4$ | 2.4 µL |
| Primer X-Syn4A-C1-f (10 µM) | 1.5 µL |
| Primer X-S-Syn4A-C1-r (10 µM) | 1.5 µL |
| Template DNA(25 ng) | 1.0 µL |
| Sterilized water (DDW) | 32.6 µL |
| DNA polymerase (KOD plus, TOYOBO) | 1.0 µL |
| Total volume | 50.0 µL |

<Reaction Conditions>

The above reaction solution was set on a thermal cycler (Gene Amp PCR system 9700, PE Applied Biosystems), and reaction was allowed to proceed under the following condition: 94° C. for 2 min; (94° C. for 15 sec, then 55° C. for 30 sec, then 72° C. for 1 min)×25 cycles; 72° C. for 7 min; 4° C. for an indefinite period.

3. Construction of Expression Vector pGST-4AaCter

The fragment obtained above was treated with XhoI. A commercially available expression vector pGEX-6P-1 (GE Healthcare Bio-Science, FIG. 6) was provided. The nucleotide sequence of the multicloning region of this vector is shown as SEQ ID NO:29, and the amino acid sequence coded for by this region as SEQ IN DO:30. Into the XhoI site within the region was inserted in a conventional manner the above-mentioned 4AaCter(696-851) fragment that had been amplified and then treated with XhoI, and thus expression vector pGST-4AaCter was constructed (FIG. 4). This fragment 4AaCter(696-851) is designed in such a manner that GST and 4AaCter(696-851) are combined in-frame if it is inserted in the correct orientation. The orientation of the inserted 4AaCter(696-851) gene was confirmed based on the restriction enzyme pattern utilizing unique KpnI and NaeI sites within the sequence, and by sequencing.

4. Transformation of Host *E. coli* Cells by Introduction of the Gene

*E. coli* BL21 strain cells were transformed by introduction into them of pGST-4AaCter constructed above. Namely, 0.1 mL of overnight culture of *E. coli* BL21 cells was applied to 5 mL of LB medium, and the mixture was shake cultured at 37° C. until the turbidity of the culture reached 0.5 (for about 2 hours). From 1 mL of this, bacterial cells were collected by centrifugation, suspended in 0.5 mL of ice-cooled 50 mM $CaCl_2$, and were let stand on ice for 30 minutes. To a 0.2-mL suspension taken from this was added pGST-4AaCter, and the mixture was let stand on ice for 30 minutes, then subjected to a heat shock at 42° C. for 30 seconds, and to this was added 0.8 mL of LB medium (to 1 mL in total). After shake cultured at 37° C. for 1 hour, the culture was streaked onto ampicillin-containing LB agar plates, and after an overnight culture at 37° C., an *E. coli* strain transformed with pGST-4AaCter was obtained.

5. Induction of Expression

Figure 7:
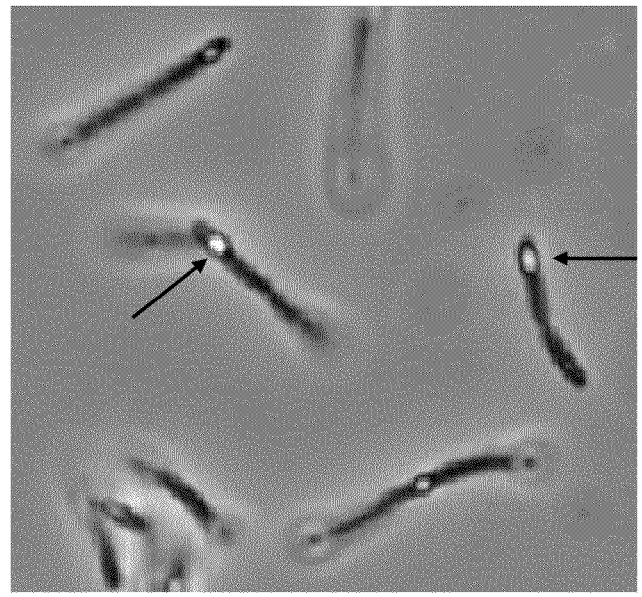
FIG. 7 is a photograph showing crystal formation in *E. coli* wells which were transformed with pGST-4AaCter and induced for expression of it.

The *E. coli* was precultured. Five mL of the medium (TB) was put in a test tube and cultured overnight. Two mL of this overnight culture was added to 200 mL of TB medium. The mixture was cultured on a shake culture apparatus (New Brunswick Scientific INOVA4230) at 240 rpm for 2-3 hours at 37° C., until the OD600 reached 0.6-0.8. IPTG (isopropyl-β-D-thiogalactopyranoside) was added to the culture fluid to make a final concentration of 0.06 mM. Culture was continued for further 2-4 hours (240 rpm 37° C.) to induce expression. Crystal formation within the cells was observed (FIG. 7, arrowheads).

6. Solubilization of the Crystals

Figure 8:
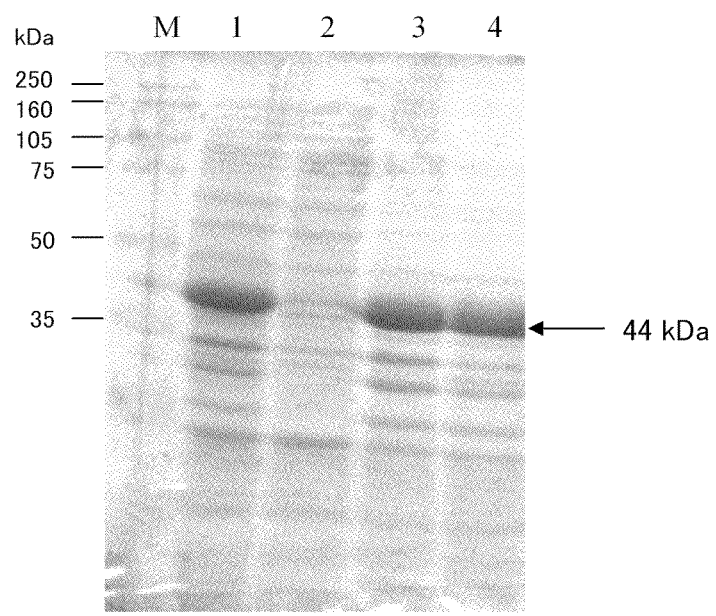
FIG. 8 is a photograph showing localization of crystals in the insoluble fraction in *E. coli* cells which were transformed with pGST-4AaCter and induced for expression of it. In the figure, M: size marker, 1: whole cell following induction of expression, 2: supernatant following fracturing the cells, 3: precipitate following fracturing the cells, 4: supernatant following solubilization.

*E. coli* cells expressing GST-4AaCter were collected and suspended in 25 mL of PBS, and then lysozyme (final concentration: 1 mg/mL) and phenylmethylsulfonyl fluoride (PMSF, final concentration: 1 mg/mL) were added to the suspension. The cells then were fractured by ultrasonication (for 6 min in total, repeating ON (20 sec) and OFF (10 sec)), and insoluble fraction was precipitated by centrifugation at 11000 rpm for 15 minutes. The precipitate, which contained crystals of GST-4AaCter, was washed by centrifugation with a proper volume of PBS, and the precipitate was suspended in a 100 mM $Na_2CO_3$ (pH 10.5) solution and incubated at room temperature for 1-2 hours to solubilize the GST-4AaCter crystals. After centrifugation, the supernatant, which contained GST-4AaCter, was subjected to analysis by SDS-PAGE. It was confirmed that the fusion protein was localized in the insoluble fraction and solubilized by alkali treatment (FIG. 8).

The GST activity of GST-4AaCter which had been solubilized in a buffer with a pH of 10.5 was assayed by CDNB (1-chloro-2,4-dinitrobenzene) method. Namely, a protein sample containing GST was put in the wells of a 96-well plate, and after addition of 200 μL of the following substrate solution to this, let stand for 1 minute at room temperature. This sample was set on an absorptiometer (Spectra MAX 250, Molecular Devices), and the change in its absorption per unit time was measured at 340 nm.

<Substrate Solution (for 4 Samples)>

| | |
|---|---|
| 100 mM potassium phosphate [pH 7.4] | 960 μL |
| 50 mM GSH* | 20 μL |
| 50 mM CDNB | 20 μL |
| Total volume | 1 mL |

*GSH: reduced glutathione

The result confirmed that GST-4AaCter exhibits a potent GST activity, though having fallen short of GST as a control (produced from *E. coli* carrying GST expression vector pGEX-6P-1) (Table 3). Besides, the maximum yield of GST-4AaCter so far reached is 0.6 mg per 3 mL culture.

TABLE 3

GST Activity of Fusion Protein

| Protein | GST activity (μmol/min/nmol GST) |
|---|---|
| GST (control, 27 kDa) | 242 |
| GST-4AaCter (fusion protein, 44 kDa) | 181 |

Example 2

Figure 9:
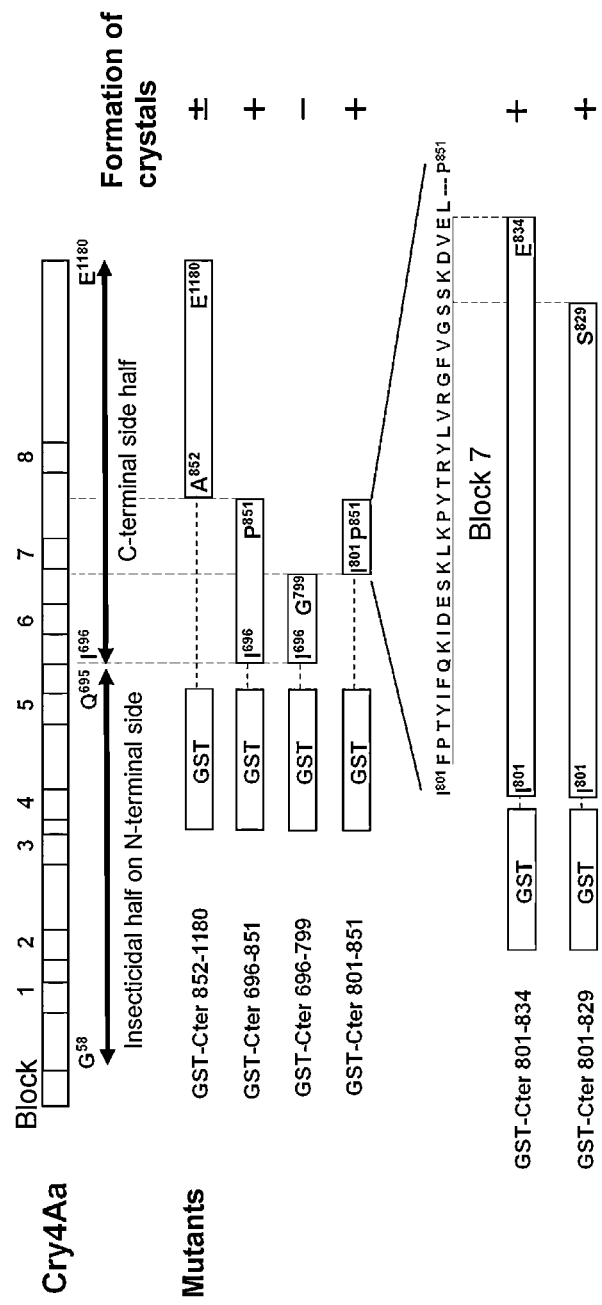
FIG. 9 is a diagram showing the results of examination for crystal forming property of fusion proteins which were produced using various fragments of Cter from Cry4Aa. Shown is a "Block 7" amino acid sequence which corresponds to amino acids 801 to 855 of SEQ ID NO: 88.
Figure 10:
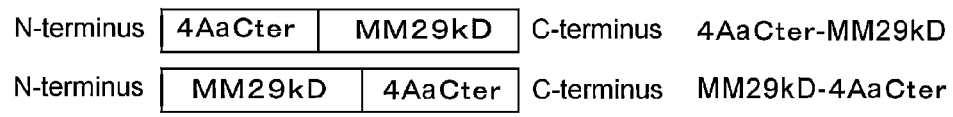
FIG. 10 is a diagram showing the two different orders of combination of MM29 kD and 4AaCter (696-851) in their fusion proteins.
Figure 11:
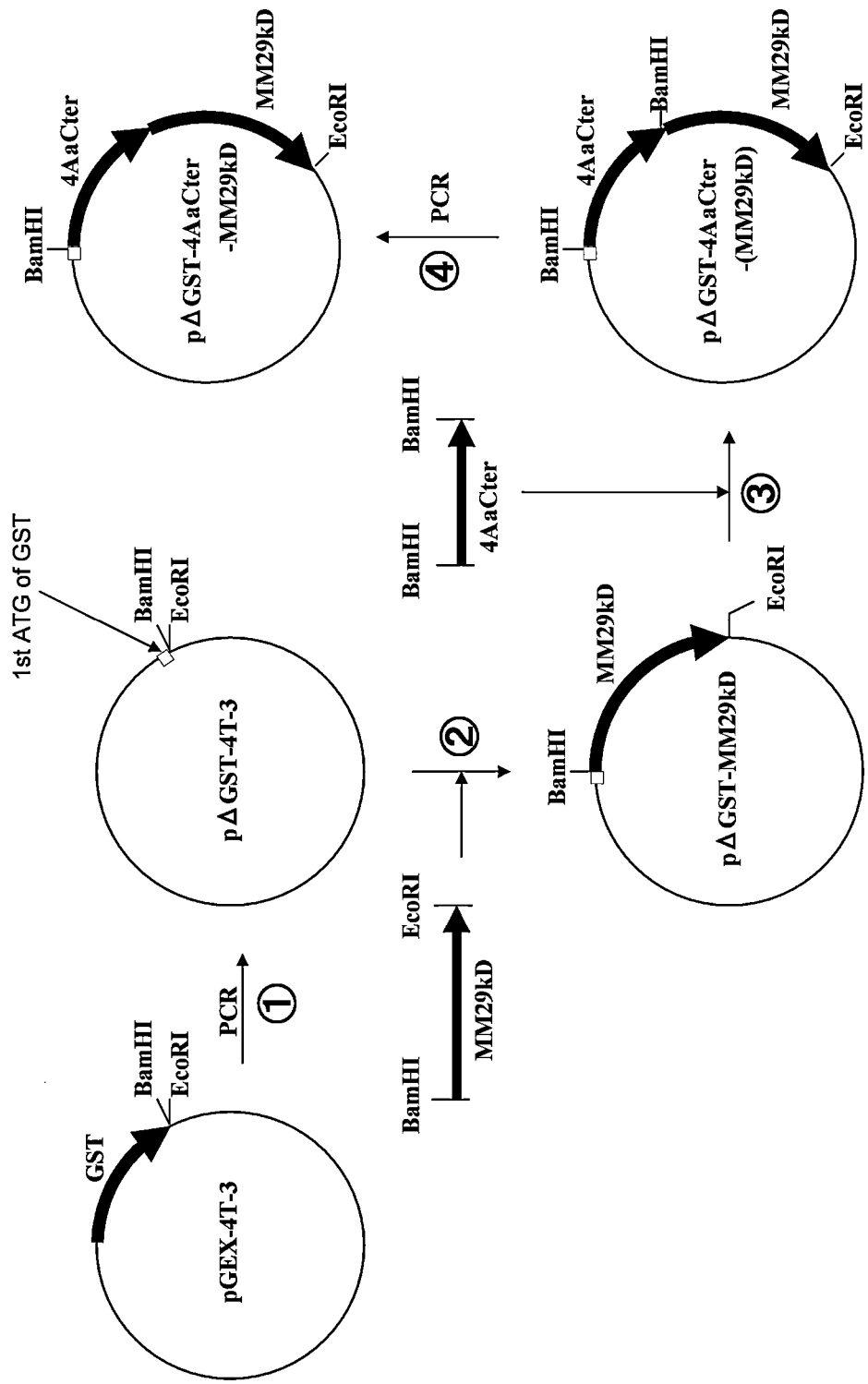
FIG. 11 is a schematic diagram illustrating the flow of the steps of construction of the expression vector for production of 4AaCter-MM29 kD.
Figure 12:
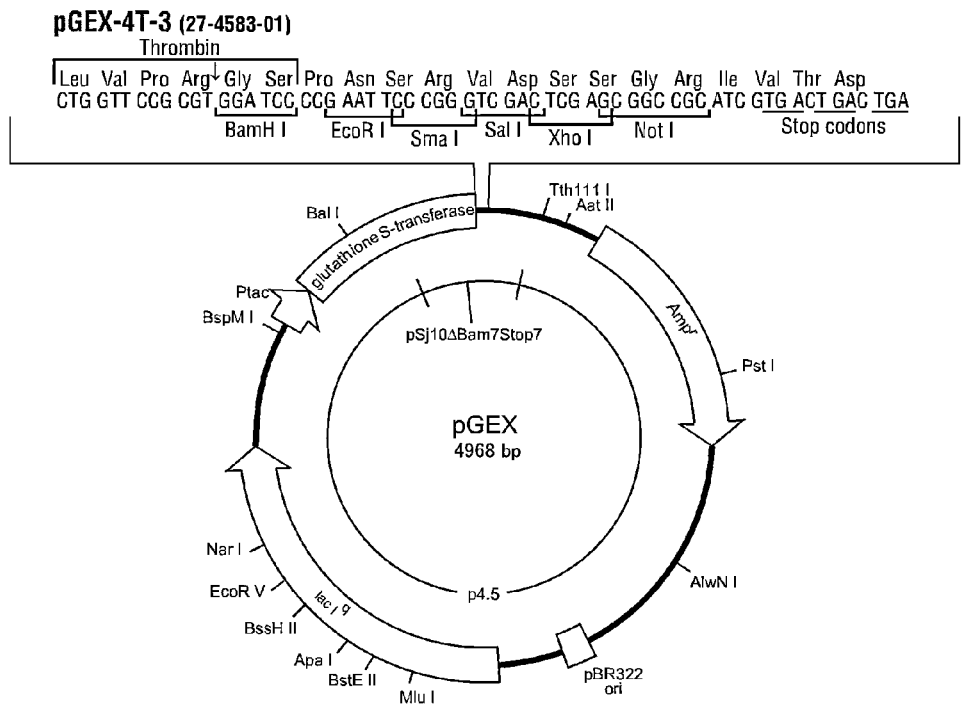
FIG. 12 illustrates a map of pGEX-4T-3. Shown are amino nucleic acid and amino acid sequences in the pGEX-4T-3 multi cloning site (SEQ ID NO: 38 and 39, respectively).
Figure 13:
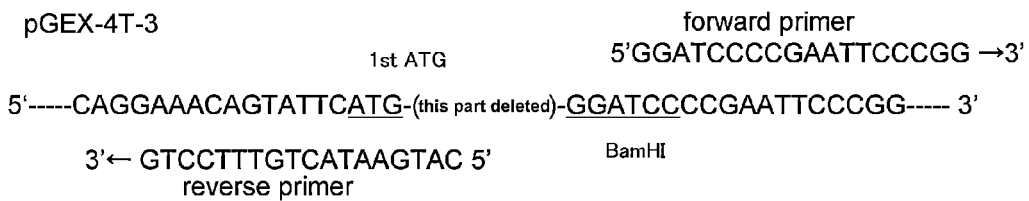
FIG. 13 illustrates the primer pair which was employed to remove the entire open reading frame (ORF) of GST except ATT. The following primers were used: p-delta-GST-4T-3 (CAGGAAACAG TATTCATGGG ATCCCCGAAT TCCCGG; SEQ ID NO: 40); Forward primer (GGATC-CCCGA ATTCCCGG; SEQ ID NO: 41); and Reverse primer (CATGAATACT GTTTCCTG; SEQ ID NO: 42).
Figure 14:
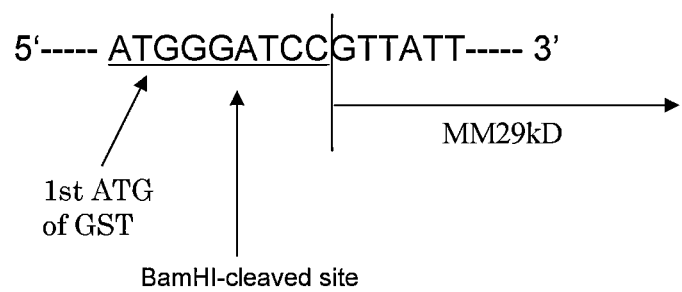
FIG. 14 is a diagram showing the nucleotide sequence near the site where "ATG" is combined with the 5'-end of the DNA coding for MM29 kD. The nucleic acid sequence around the 5' end of MM29 kD is shown in SEQ ID NO: 43.
Figure 15:
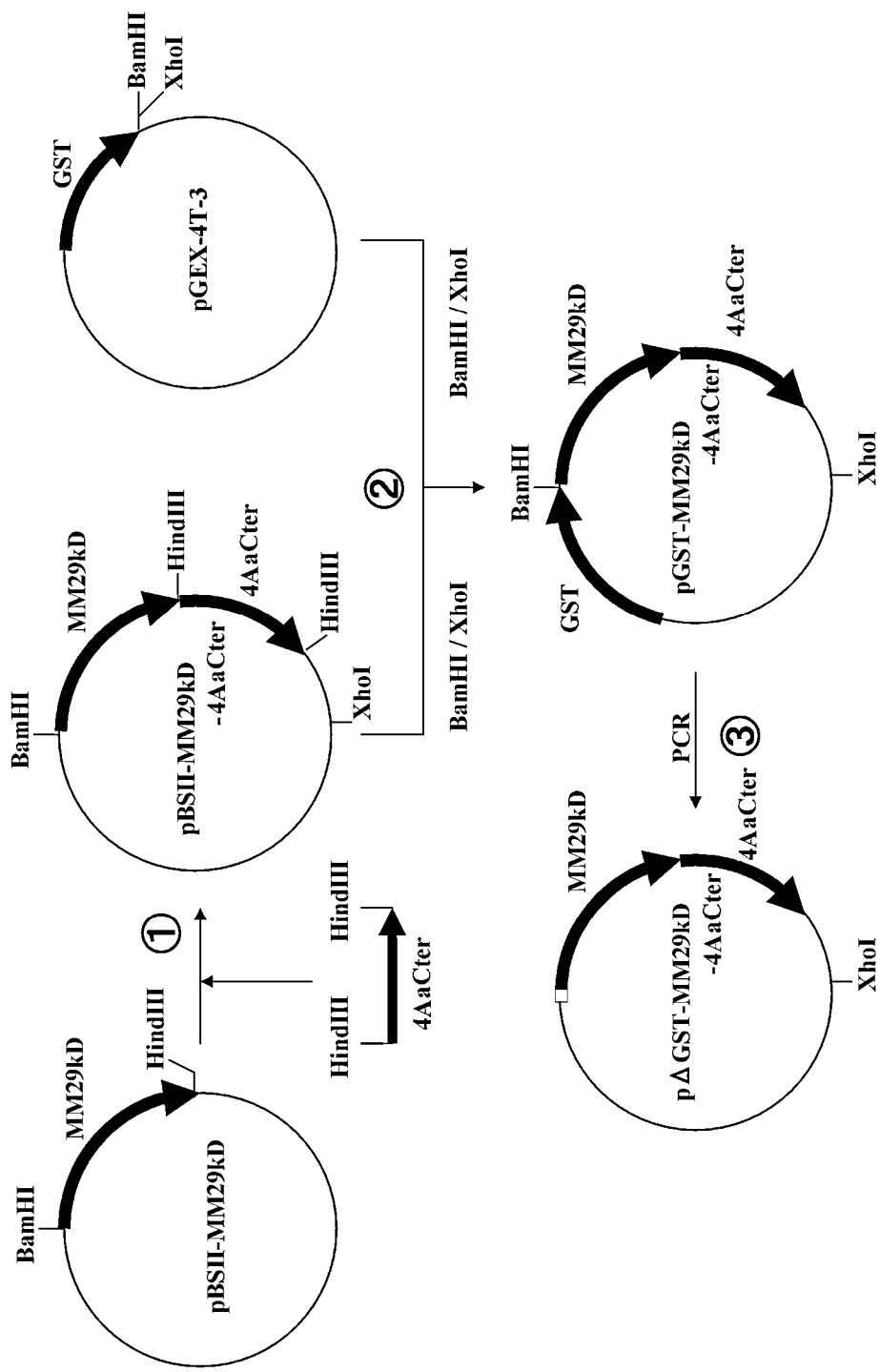
FIG. 15 is a schematic diagram illustrating the flow of construction of the expression vector for production of MM29 kD-4AaCter.

Production of Fusion Protein of Various Fragments of Cry4A and Glutathione-S-Transferase Study was made to identify where the indispensable region resides in 4AaCter for a fusion protein to form crystals. As shown in FIG. 9, various parts of the amino acid sequence Cry4Aa were amplified, and their fusion proteins with GST were produced according to a procedure similar to that followed in Example 1. Each of them was examined for their formation of crystals in the same manner as in Example 1. The fusion protein with 4AaCter(852-1180) was not found to form clear crystals, nor did the fusion protein with GST-4AaCter(696-799) exhibit formation of crystals. On the other hand, crystal formation was confirmed with GST-4AaCter (696-851) [amino acid sequence of the Cter(696-851) portion: SEQ ID NO:6] and with those fusion proteins prepared using gradually shortened peptide chains, i.e., GST-4AaCter (801-851), GST-4AaCter(801-834) [amino acid sequence of the 4AaCter(801-834) portion: SEQ ID NO:31], and GST-4AaCter(801-829) [amino acid sequence of the 4AaCter (801-829) portion: SEQ ID NO:7]. This indicates that in 4AaCter, the sequence essential for crystal formation is a polypeptide chain portion consisting of 29 amino acids, 801-829, equally included in these latter Cter portions.

Example 3

Production of Fusion Protein of 4AaCter(696-851) with MM29 kD

Figure 16:
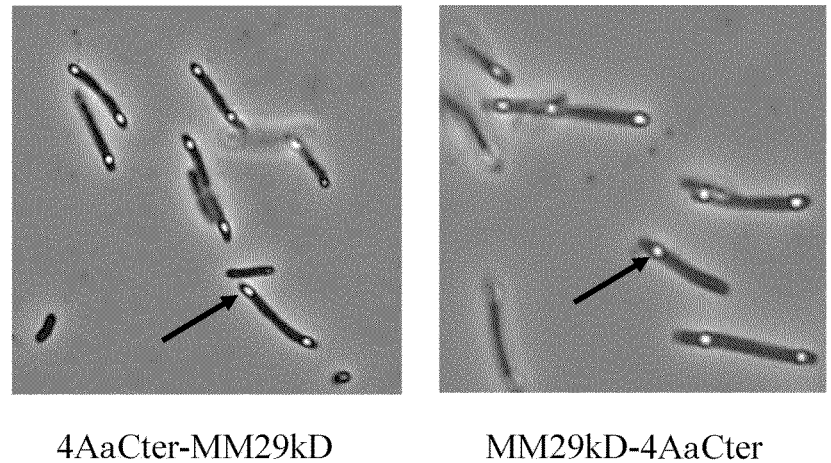
FIG. 16 presents photographs showing crystal formation in the *E. coli* cells which were transformed with pAGST-4AaCter-MM29 kD or pAGST-MM29 kD-4AaCter, respectively, and induced for their expression.

MM29 kD, a cytotoxic protein derived from *B. thuringiensis*, exhibits a potent toxicity to mammalian cells (esp. to leukemia and cancer cells). MM29 kD is produced and accumulated in *B. thuringiensis* cells in the form of a precursor consisting of 304 amino acids (whose nucleotide and amino acid sequences shown as SEQ ID NO:32 and SEQ ID NO:33, respectively), and converted to the active form through removal of 28 amino acids from the N-terminus and some from the C-terminus by proteinase K. Though it is not known as yet how many amino acids are removed from its C-terminus in nature, removal of 23 amino acids gives an active protein. And based on studies of its molecular size, it is considered that about 23 amino acids are removed also in nature. The nucleotide sequence of the active MM29 kD, which is formed by removal of N-terminal 28 amino acids and C-terminal 23 amino acids, is presented as SEQ ID NO:34, and the corresponding amino acid sequence as SEQ ID NO:35.

While it has so far been prepared through its expression in the form of a fusion protein with GST in *E. coli* cells, it has been difficult to obtain MM29 kD in high yield. Namely, MM29 kD is a protein which cannot be expressed easily. This is thought to be due to the adverse effects of MM29 kD, which accumulates in the soluble fraction, on the viability and reproduction of the *E. coli* cells. An attempt was made to let this protein accumulate in the form of crystals (i.e., in a manner that the soluble fraction is kept free of this protein) and thus obtain high yield while averting the adverse effects. For this purpose, fusion proteins were constructed in which 4AaCter was added in-frame to either the N- or C-terminus of MM29 kD, respectively, i.e., 4AaCter-MM29 kD and MM29 kD-4AaCter (FIG. 10).

1. Construction of Expression Vector for Production of Fusion Protein 4AaCter-MM29 kD (FIG. 11)

Using the total DNA from *B. thuringiensis* MM50G2 strain as a template and the following set of primers, PCR was performed to prepare the MM29 kD gene DNA having a BamHI site on the upstream end and an EcoRI site on the downstream end (FIG. 10).

```
(1) Primer Cytox-N-f-Bam:
                                        (SEQ ID NO: 36)
GTGGATCCGTTATTCAAGAATACCTTACGTTTAATG (2) Primer Cytox-r-999-Eco:
                                        (SEQ ID NO: 37)
AGGAATTCAAGCTTCTTGCTGTTCAGC
```

A commercially available protein expression vector pGEX-4T-3 was provided (FIG. 12). The nucleotide sequence of the multicloning region of this expression vector is presented as SEQ ID NO:38, and the amino acid sequence coded for by this as SEQ ID NO:39. One day mutagenesis using PCR was applied in a conventional manner to remove from the vector the entire open reading frame (ORF) of GST leaving behind its start codon "ATG" alone to prepare pΔGST-4T-3 (FIG. 11). The nucleotide sequence of pΔGST-4T-3, part of which is shown in FIG. 13, is presented as SEQ ID NO:40. And the forward primer and the reverse primer shown in FIG. 13 employed in this process are presented as SEQ ID NO:41 and SEQ ID NO:42, respectively. Using these primers, BamHI was inserted immediately after that start codon "ATG" left in pΔGST-4T-3.

Then, the above DNA fragment (which has a BamHI site on the upstream end and an EcoRI site on the downstream end) was inserted in a conventional manner into the BamHI/EcoRI site of pΔGST-4T-3 to form vector pΔGST-MM29 kD. A region of nucleotide sequence near the start codon "ATG" of GST and 5'-end of the above-mentioned DNA coding for MM29 kD is given in FIG. 14 and as SEQ ID NO:43.

The DNA fragment (BamHI)-4AaCter-(BamHI) was inserted into the BamHI site of pΔGST-MM29 kD prepared above to construct vector pΔGST-4AaCter-(MM29 kD).

Then, using this as a template, one day mutagenesis was performed to replace the nucleotide sequence "GCGGATCC", which connected between 4AaCter and MM29 kD, with "GCG". 4AaCter and MM29 kD thus were connected in-frame and gave pΔGST-4AaCter-MM29 kD (FIG. 11).

2. Construction of Expression Vector for Production of Fusion Protein MM29 kD-4AaCter (FIG. 15)

Using PCR, DNA fragment (BamHI)-MM29 kD-(HindIII) was prepared by adding a nucleotide sequence "GGATCC" to the 5' end of the DNA sequence coding for MM29 kD (active form) and a nucleotide "TGAATTC" to the 3' end, respectively. This process added to the 3' end of MM29 kD a stop codon "TGA", and provided a EcoRI site simultaneously. At the same time, a HindIII site was freshly created immediately upstream of this EcoRI site.

A PCR was performed using the DNA coding for 4AaCter. For this process, nucleotide sequences of the primers had been designed so that HindIII restriction sites might be added at either end of this DNA, and that in-frame connection to the terminal HindIII site might become possible (namely, so that "AAGCTTTA" might be added to the 5' end of the DNA coding for 4AaCter, and "AAGCTT" at the 3' end).

A recombinant vector pBSII-MM29 kD was prepared by inserting the above DNA fragment, (BamHI)-MM29 kD-(HindIII), into the BamHI/HindIII site of a commercially available cloning vector pBluescript II SK+ (pBSII, Stratagene, USA).

Then, by inserting (HindIII)-4AaCter-(HindIII) fragment into the HindIII site of the recombinant vector pBSII-MM29 kD (thus MM29 kD and 4AaCter linked in-frame), pBSII-MM29 kD-4AaCter was constructed.

By treating pBSII-MM29 kD-4AaCter with a BamHI/XhoI restriction enzyme, a BamHI/XhoI DNA fragment including the (BamHI)-MM29 kD-4AaCter-(HindIII) region was cut out, which then was inserted into the BamHI/XhoI site of pGEX-4T-3 to form pGST-MM29 kD-4AaCter.

One-day mutagenesis using PCR was applied using pGST-MM29 kD-4AaCter DNA as a template, the ORF of GST was removed up to the BamHI recognition site sequence leaving the first "ATG" (start codon) alone, and the tac-promoter upstream of GST and the start codon "ATG" was directly linked in-frame to the MM29 kD gene, to form pΔGST-MM29 kD-4AaCter (FIG. 15).

3. Transformation of Host *E. coli* Cells by Introduction of a Gene and Collection of Crystals

*E. coli* BL21 cells were transformed by introduction either of the pΔGST-4AaCter-MM29 kD or of the pΔGST-MM29 kD-4AaCter, which had been constructed above 1 and 2, respectively. Five mL of TB medium was inoculated with either of the transformant BL21 strain cells, and after addition of 10 μL of 50 mg/mL Amp, shake cultured at 37° C. for 12 hours (preculture). Fifty-mL TB medium was inoculated with 500 μL of the preculture, and 100 μL of 50 mg/mL Amp was added to this. Shake culture was done at 37° C. for 3 hours ($OD_{600}$=about 0.8). To this was added 50 μL of 100 mM IPTG, and culture was continued at 37° C. for 3 hours. Formation of crystals was confirmed in the *E. coli* cells transformed either with 4AaCter-MM29 kD or with MM29 kD-4AaCter (FIG. 16, arrowheads). The bacterial cells were collected and suspended in 20 mL of PBS [pH7.5] and centrifuged (10000 rpm, 4° C., 10 min: RS-18 IV/TOMY). The precipitate separated was suspended in ice-cooled sterilized water, then fractured by ultrasonication (for 5 min in total, repeating ON (10 sec) and OFF (10 sec)), and centrifuged (10000 rpm, 4° C., 10 min). The precipitate, after washed by centrifugation (not less than 3 times) with ice-cooled sterilized water, was suspended in 2 mL of 50 mM Tris-HCl [pH 7.4]. This suspension was subjected to sucrose density-gradient centrifugation, and the layer which contained crystals (white band) was collected and suspended in 20 mL of PBS [pH7.5]. This was centrifuged (12000 rpm, 4° C., 10 min) and the precipitate was further centrifuged in ice-cooled sterilized water (at least 3 times). The supernatant was fully removed, and the precipitate was suspended in 20 mL of ice-cooled sterilized water. After additional centrifugation (12000 rpm, 4° C., 10 min), precipitate was suspended in 2 mL of ice-cooled sterilized water, then distributed into sample tubes, and stored at −80° C.

4. Solubilization of Crystals

Figure 17:
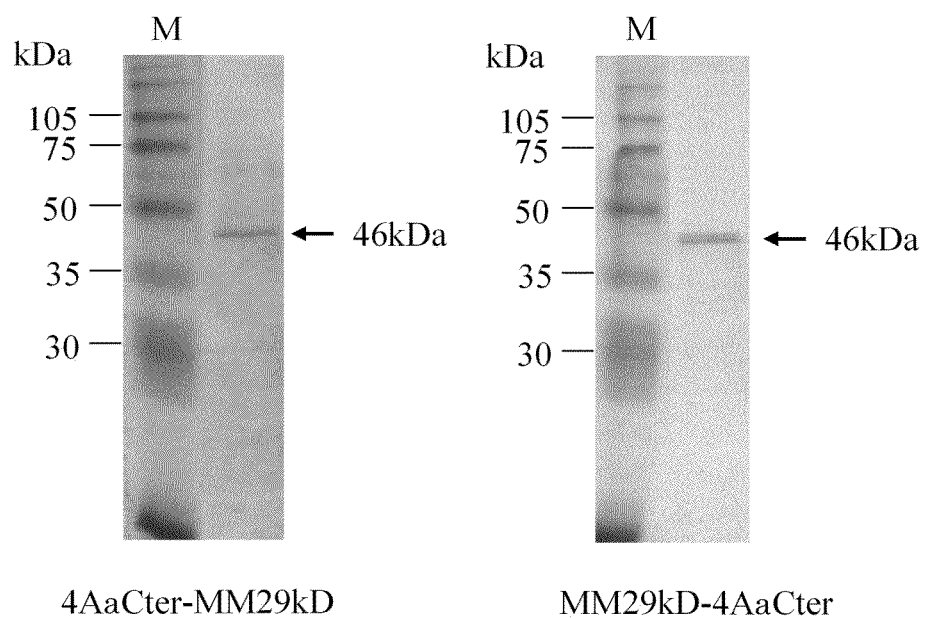
FIG. 17 present photographs showing the results of SDA-PAGE performed with 4AaCter-MM29 kD and MM29 kD-4AaCter.

The precipitate was suspended in a solubilization buffer (100 mM $Na_2CO_3$ [pH 10.5], 10 mM DTTz) to solubilize the crystals (37° C., 30 min) (crystals can be easily solubilized and collected at pH 10-12). After centrifugation (14000 rpm, 4° C., 10 min), the supernatant (4AaCter-MM29 kD of MM29 kD-4AaCter) was collected. This was separately purified by anionic column chromatography (HiTrap Q XL, GE Healthcare Bioscience). The proteins adsorbed by the column and then was eluted using 100 mM, 200 mM, and 300 mM NaCl stepwise. 4AaCter-MM29 kD and MM29 kD-4AaCter were found to be eluted with 300 mM NaCl. Examination using SDS-PAGE revealed that these standard samples had been purified to a single band (FIG. 17).

5. Release and Collection of MM29 kD from Fusion Protein

Then, to the supernatant containing 4AaCter-MM29 kD or MM29 kD-4AaCter was added proteinase K in a proper amount (1/10 of the amount of the protein in the supernatant) to remove the 4AaCter sequence upstream or downstream of MM29 kD (37° C., 1 hour). MM29 kD, which is rather resistant to decomposition with proteinase K, survives this treatment as the core polypeptide. The reaction was terminated by 0.1 M PMSF (phenylmethylsulfonium fluoride) which was added to a final concentration of 1 mM. The protein was purified again by anionic ion-exchanger chromatography. MM29 kD is not adsorbed by the column and flows through. Analysis of the purified MM29 kD by SDS-PAGE confirmed that either protein was purified to a single band.

6. Assessment of Cytotoxicity

Using the proteins, 4AaCter-MM29 kD, MM29 kD-4AaCter, and free MM29 kD, purified above, assessment was made for cytotoxicity (lethal activity) of the purified fusion proteins by MTT assay employing Jurkat cells, which originate from a leukemia cell, as a target. Briefly, the number of the Jurkat cells (purchased from Institute of Physical and Chemical Research) were counted using Burker Turk Deep (1/10 mm). The cells were diluted to the density of $5.0 \times 10^5$ cells/mL with a medium for measurement for assay (RPMI 1640 free of phenol red, Nissui). The cell culture was placed, 90 μL each, in a necessary number of wells of a 96-well plate. Ten μL each of the samples which had been diluted to proper concentrations with PBS [pH7.5] was added to each well, and incubation was made (37° C., 3 hrs). Five mg/mL MTT (3-[4,5-dimethylthiazol-2-yl]-2,5-diphenyltetrazolium bromide, Sigma, dissolved in the medium for measurement) then was added to each well, and incubation was made (37° C., 3 hrs). 100 μL of acidic isopropanol was added to each well, and after sufficient pipetting, OD (570 nm) was measured by a spectrophotometer to calculate survival rate of the cells. As a result, 4AaCter-MM29 kD exhibited an activity comparable to GST-MM29 kD, which had been used as the standard sample in the studies of MM29 kD. Compared to these, the activity of MM29 kD-4AaCter was found to be several times higher (Table 4). Free MM29 kD, prepared either from 4AaCter-MM29 kD or MM29 kD-4AaCter, exhibited its EC50 at 0.4-0.5 ng/mL (Table 4), which suggests that it is not that MM29 kD is irreversibly inactivated when it is joined by 4AaCter at its N-terminus, but probably is lowered in its apparent biological activity due to some steric hindrance. Besides, the yield of 4AaCter-MM29 kD and MM29 kD-4AaCter obtained above was 0.3-0.5 mg per 50 mL of culture, which was at least 6 times the yield of GST-MM29 kD (usually, about 50 μg per 50 mL of culture), which had so far been utilized to produce MM29 kD in *E. coli* as a host.

TABLE 4

Cytotoxicity of Fusion Protein to Jurkat Cells

| Protein | Cytotoxicity (EC50, ng/ml) |
|---|---|
| GST-MM29kD | 23.4 |
| 4AaCter-MM29kD | 24.6 |
| MM29kD-4AaCter | 4.7 |
| Free MM29kD | 0.4-0.5 |

Example 4

Production of Fusion Protein of Cter of Cry1Aa and Glutathione-S-Transferase

As it was confirmed as shown in Examples 1-3 that GST and MM29 kD can be produced in a large amount using *E. coli* in the form of their fusion proteins with various fragments of 4AaCter, an attempt then was made to produce fusion proteins with the Cter of other Cry proteins. Using 1AaCter, the Cter of Cry1Aa (insecticidal toxin specific to lepidopteran insects (butterflies and moths)), which exhibits an insecticidal spectrum utterly different from that of Cry4Aa (insecticidal toxin specific to dipteran insects (mosquitoes)), a large-scale expression of GST was tried as described below.

1. Preparation of a Gene Coding for GST-1AaCter(622-777) and Construction of an Expression Vector pGST-1AaCter Based on the result of alignment [using a software ClustalW] with the amino acid sequence of 4AaCter(696-851), a corresponding peptide, 1AaCter(622-777), was selected. To prepare a fusion protein with this peptide chain, a gene fragment containing the coding region for 1AaCter(622-777) (amino acid sequence set forth as SEQ ID NO:1) was amplified by PCR. This PCR was performed using DNAs extracted from *B. thuringiensis* subsp. *sotto* T84A1 strain as a template, together with the following primers, which are specific to 1AaCter:

```
(1) Primer 1Aa3-C1-f:
                              (SEQ ID NO: 44)
GGATCCGCGGTGAATGAGCTG
```

```
         -continued
(2) Primer 1Aa3-C1-r:
                                  (SEQ ID NO: 45)
     CTCGAGACCCACATTTACTGT
```

Figure 18:
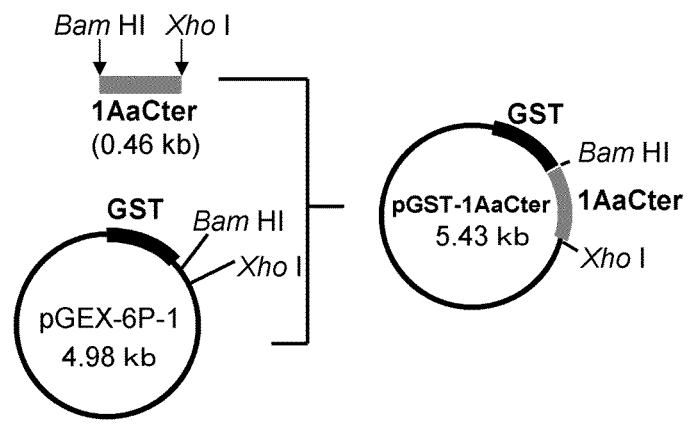
FIG. 18 is a schematic diagram illustrating the flow of construction of expression vector pGST-1AaCter.

The gene fragment (nucleotide sequence set forth as SEQ ID NO:46) which was thus amplified is provided with a BamHI site at its upstream end and a XhoI site at its downstream end, respectively. This fragment was inserted in-frame into the BamHI-XhoI site within the multicloning site which is downstream of the GST gene of the expression vector pGEX-6P-1, giving an expression vector, pGST-1AaCter (FIG. 18). pGST-1AaCter is designed to express the fusion protein of GST and 1AaCter (GST-1AaCter).

2. Transformation of *E. coli* Host by Introduction of the Gene

Figure 19:
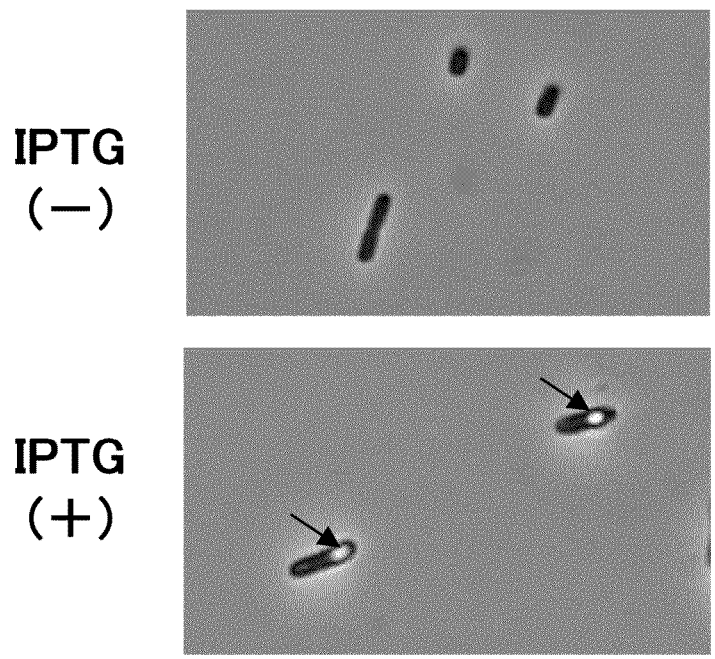
FIG. 19 presents photographs showing crystal formation in *E. coli* cells which were transformed with pGST-1AaCter and induced for expression of it.
Figure 20:
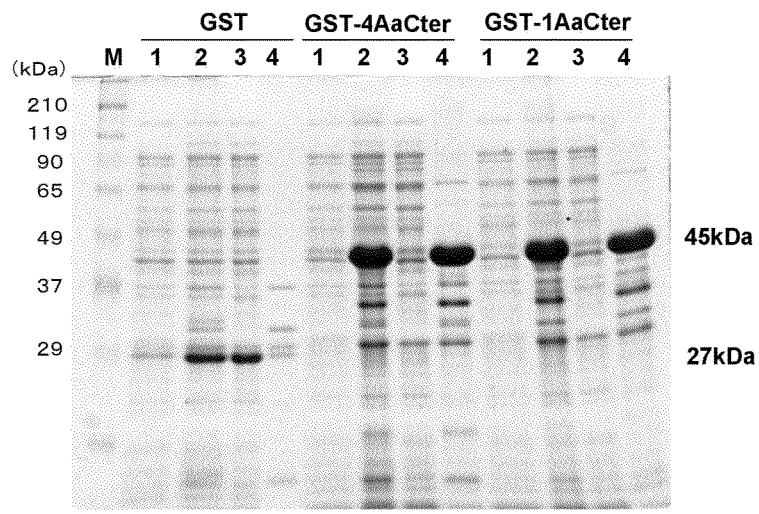
FIG. 20 presents photographs showing the result of SDS-PAGE demonstrating the insoluble-fraction localization of crystals obtained from the *E. coli* cells which were transformed with pGST-1AaCter and induced for its expression. In the figure, M: size marker, 1: IPTG(−) total proteins, 2: IPTG (+), 3: IPTG(+) centrifugation supernatant (soluble protein fraction), 4: IPTG(+) centrifugation precipitate (insoluble protein fraction).
Figure 21:
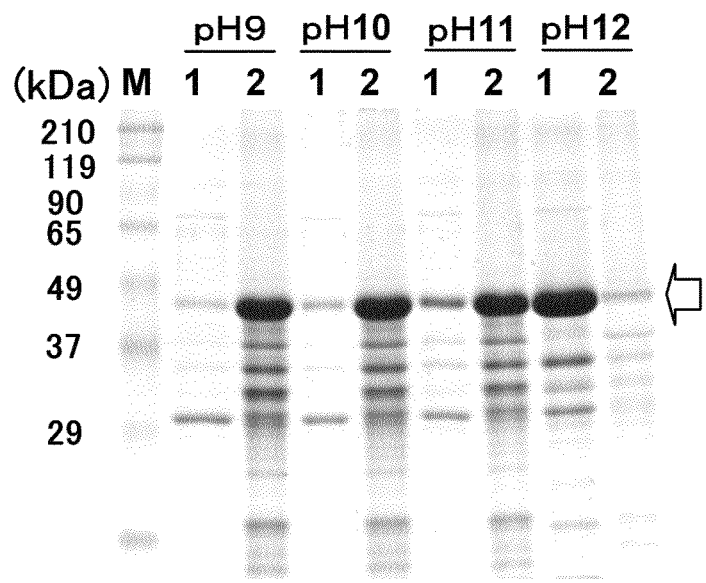
FIG. 21 presents photographs showing the result of SDA-PAGE carried out following alkaline solubilization of the crystals obtained from *E. coli* cells were transformed with pGST-1AaCter and induced for expression. In the figure, M: size marker, 1: centrifugation supernatant (soluble protein fraction), 2: centrifugation precipitate (insoluble protein fraction).

*E. coli* BL21 cells were used as the host. The cells were transformed by introduction of the above expression vector pGST-1AaCter in the same manner as in Examples 1 and 2, and following induction of expression, GST-1AaCter was expressed. Thus, formation of crystals was observed in the cells, as was the case with GST-4AaCter (FIG. 19, arrowheads). SDS-PAGE analysis of the supernatant (soluble protein fraction) and the precipitate (insoluble protein fraction) separated by centrifugation showed that GST-1AaCter, which was estimated to be about 45 kDa, was located mainly in the insoluble protein fraction (FIG. 20). The amount of expressed GST-1AcCter was estimated to be about 5 µg per 10 µg of *E. coli* total proteins, according to computer image analysis. While the GST-1AaCter crystals were scarcely soluble in alkaline buffer solutions with a pH of 9-11, they were solubilized in a buffer with a pH of 12 (FIG. 21). Measurement of GST activity was made by the CDNB assay and revealed their high activity comparable to that of the GST purified standard [purified from pGEX-6P-1-introduced *E. coli* cells through Glutathione Sepharose 4B (GE Healthcare)] (Table 5).

TABLE 5

GST activity of GST-1AaCter

| Protein | GST activity (µmol/min/nmol GST) |
|---|---|
| GST purified standard | 107.3 |
| GST-1AaCter | 99.8 |

Example 5

Preparation of Fusion Protein with Cter from Cry1Ac and Glutathione-S-Transferase Cry1Ac is an insecticidal toxin specific to lepidopteran insects (butterflies and moths) like Cry1Aa employed in Example 4. Cry1Ac, however, exhibits different characteristics from those of Cry1Aa, such as its N-acetylgalactosamine (GalNAc) recognizing lectin activity. An examination was carried out in the following manner to find whether a protein (GST) linked to the Cter (1AcCter) from this Cry1Ac protein would form crystals and accumulate in *E. coli* cells.

1. Preparation of Gene Coding for GST-1AcCter(624-779) and Construction of Expression Vector pGST-1AcCter Based on the result of alignment [using a software ClustalW] with the amino acid sequence of 4AaCter(696-851), a corresponding part, 1AcCter(624-779), was selected from the sequence of Cry1Ac1. In order to prepare a fusion protein with this, a gene fragment containing the coding region for 1AcCter(624-779) (amino acid sequence set forth as SEQ ID NO:4) was amplified by PCR. This PCR was performed using DNAs extracted from B. *thuringiensis* subsp. *kurstaki* HD73 strain as a template, together with the following primers, which are specific to 1AcCter(624-779):

```
(1) Primer 1Ac1-C1-f:
                                  (SEQ ID NO: 47)
     GGATCCGCGGTGAATGCGCTG (2) Primer 1Ac1-C1-r:
                                  (SEQ ID NO: 48)
     CTCGAGTGGCACATTTACTGT
```

The gene fragment (nucleotide sequence set forth as SEQ ID NO:49) which was thus amplified was provided with a BamHI site at its upstream end and a XhoI site at its downstream end, respectively. This fragment was inserted in-frame into the BamHI-XhoI site downstream of the GST gene of the expression vector pGEX-6P-1, which gave pGST-1AcCter an expression vector for a fusion protein of GST and 1AcCter (GST-1AcCter).

2. Transformation of *E. coli* host by Introduction of the Gene

Figure 22:
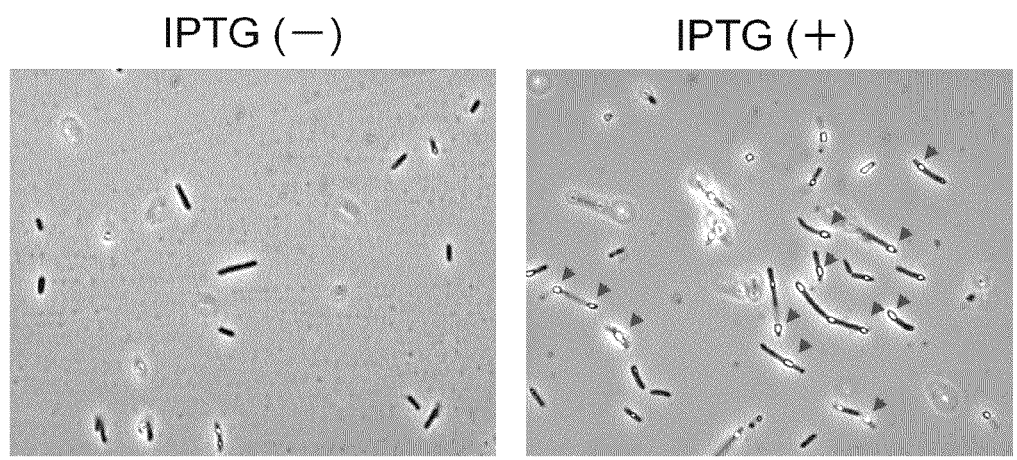
FIG. 22 presents photographs showing crystal formation in *E. coli* cells which were transformed with pGST-1AcCter and induced for expression.
Figure 23:
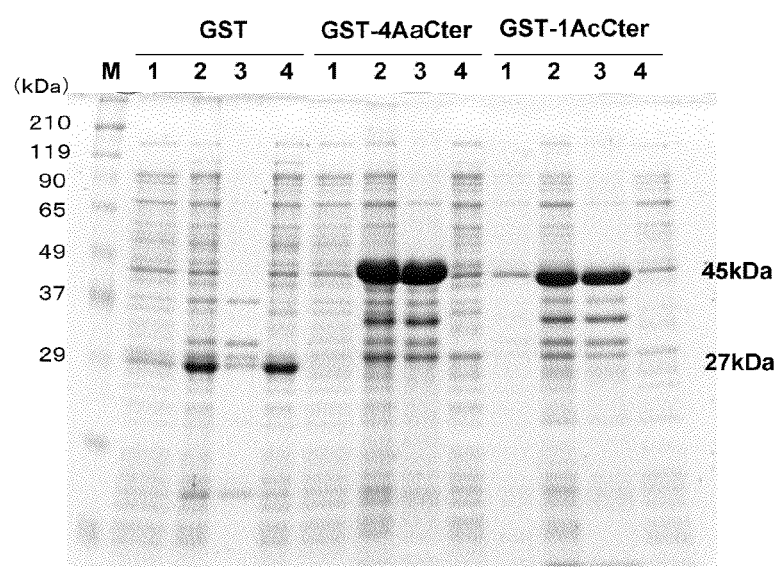
FIG. 23 present photographs showing the result of SDS-PAGE demonstrating the insoluble-fraction localization of crystals obtained from *E. coli* cells which were transformed with pGST-1AcCter and induced for expression. In the figure, M: size marker, 1: IPTG(−) total proteins, 2: IPTG(+) total proteins, 3: IPTG(+) entrifugation precipitate (insoluble protein fraction), 4: IPTG(+) centrifugation supernatant (soluble protein fraction).
Figure 24:
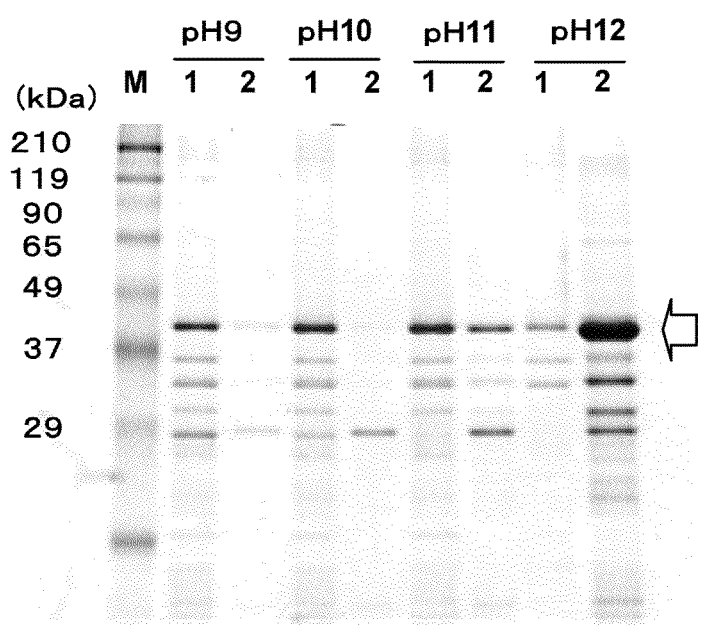
FIG. 24 presents photographs showing the results of SDA-PAGE following alkaline solubilization of crystals obtained from *E. coli* cells which were transformed with pGST-1Ac-Cter and induced for expression, indicating the result of solubility test of the crystals formed with 1AcCter. In the figure, M: size marker, 1: centrifugation precipitate (insoluble protein fraction), 2: centrifugation supernatant (soluble protein fraction).

Using *E. coli* BL21 cells in the same manner as in Example 1, CST-1AcCter was expressed. As a result, formation of crystals was observed in the cells, as were the cases with GST-4AaCter and GST-1AaCter (FIG. 22, arrowheads). SDS-PAGE analysis of the supernatant (soluble protein fraction) and the precipitate (insoluble protein fraction) separated by centrifugation showed that GST-1AcCter, which was estimated to be of about 45 kDa, was found localized mainly in the insoluble protein fraction (FIG. 23). The amount of expressed GST-1AcCter was about 5 µg per 10 µg of the *E. coli* total proteins, as estimated by computer image analysis. While the GST-1AcCter crystals were scarcely soluble in alkaline solutions with a pH of 9-11, they were solubilized in a buffer with a pH 12 (FIG. 24). Measurement of the activity of GST-1AcCter thus solubilized was made by the CDNB assay and revealed that its activity was comparable to that of the purified standard (Table 6).

TABLE 6

GST activity of GST-1AcCter

| Protein | GST activity (µmol/min/nmol GST) |
|---|---|
| GST purified standard | 107 |
| GST-1AcCter | 105 |

Example 6

Preparation of Fusion Protein with Cter from Cry8Ca

An attempt then was made to prepare a fusion protein with a Cter from Cry8Ca1. Based on the result of alignment [using a software ClustalW] with the amino acid sequence of 4AaCter(696-851), a corresponding sequence, 8CaCter(672-829), was selected. In order to prepare a fusion protein with this, a vector having a DNA in which a gene fragment coding for 8CaCter(Lys672-Pro829) (amino acid sequence set forth as SEQ ID NO:14) had been inserted in-frame downstream of a gene fragment coding for GST was introduced to *E. coli* BL21 strain cells to transform these, and the expression of the fusion protein was induced. As a result, formation of crystals was observed in the E. coli cells.

Example 7

Preparation of C-Reactive Protein (CRP) Utilizing 4AaCter

C-reactive protein (CRP), which occurs in the blood in response to an inflammation, is an inflammation marker, and its measurements in the blood: which is performed using an antibody reactive specifically to CRP (anti-CRP antibody), can be used as an index to the activity and severity, in follow-up observations and prognosis of an inflammatory diseases. There is a high demand for anti-CRP antibody, and so is the demand for CRP itself, which is the necessary immunogen in order to produce the antibody. However, as CRP collected and purified from the body contains a substantial amount of contaminants originating from its sources, an anti-CRP antibody prepared using it as the immunogen could react with other compounds occurring in the body, thereby affecting the measurement. For this reason, as well as for steady supply of the immunogen CRP, it has been desired that production of anti-CRP antibody is made using, as the immunogen, a recombinant CRP produced by microorganisms. Thus, an attempt was made to produce CRP utilizing 4AaCter.

<Construction of Expression Vector for Production of Fusion Protein>

Human CRP gene which had been prepared by gene synthesis in the following manner was inserted in-frame between the BamHI and XhoI sites of the above mentioned pΔGST-4T-3 to construct pΔGST-CRP.

Namely, the gene segment encoding human CRP was synthesized by recursive PCR performed with reference to a database (GenBank NM_00567). PCR was performed using a DNA fragment prepared by PCR using a pair of primers each of which had at an end a sequence which was complementary to the sequence at an end of the other: i.e., CRP__1f (SEQ ID NO:97)(6 nucleotides at the 5'-end of this form a BamHI site) and CRP__2r (SEQ ID NO:98); and fragments prepared by PCR using a series of primers each having at its ends sequences complementary to its flanking primers: i.e., CRP__3f (SEQ ID NO:99), CRP__4r (SEQ ID NO:100), CRP__5f (SEQ ID NO:101), CRP__6f (SEQ ID NO:102), CRP__7f (SEQ ID NO:103), CRP__8r (SEQ ID NO:104), CRP__9f (SEQ ID NO:105), CRP__10r (SEQ ID NO:106), CRP__11f (SEQ ID NO:107), CRP__12r (SEQ ID NO:108)(6 nucleotides at the 5'-end of this form a XhoI site), and thus a DNA coding for the full length CRP (SEQ ID NO:109)(respective 6 nucleotides at 5'- and 3'-ends form restriction sites required in subcloning) was prepared. In the amino acid sequence (SEQ ID NO:110) coded for by the DNA, the parts consisting of two amino acids at the N- and C-termini, respectively, are linker sequences which have been brought in as part of the restriction sites. The DNA (SEQ ID NO:109) coding for the full length human CRP was inserted in-frame into pΔGST-4T-3 which had been digested with BamHI and XhoI, to construct pΔGST-CRP.

Then a fragment coding for 4AaCter was inserted in-frame into the BamHI site of pΔGST-CRP to construct pΔGST-4AaCter-CRP. Namely, PCR was performed using the open reading frame of the above-mentioned cry4Aa-S2 gene as a template, and using primers B-Syn4A-C1-f (SEQ ID NO:111)(6 nucleotides at its 5'-end form a BamHI site) and B-Syn4A-C1-rn (SEQ ID NO:112)(6 nucleotides at its 5'-end form a BamHI site) to amplify the DNA fragment coding for 4AaCter(696-851). The fragment thus obtained is provided with BamHI sites at it both ends. The reaction solution and reaction conditions for this PCR were as follows.

<Reaction Solution>

| | |
|---|---|
| 10 × PCR buffer (for KOL plus) | 5.0 μL |
| 2 mM dNTP | 5.0 μL |
| 25 mM MgSO$_4$ | 2.4 μL |
| Primer B-Syn4A-C1-f (10 μM) | 1.5 μL |
| Primer B-Syn4A-C1-rn (10 μM) | 1.5 μL |
| Template DNA (25 ng) | 1.0 μL |
| Purified water (DDW) | 32.6 μL |
| DNA polymerase (KOD plus, TOYOBO) | 1.0 μL |
| Total volume | 50.0 μL |

<Reaction Condition>

The above reaction solution was set in a thermal cycler (Gene Amp PCR system 9700, PE Applied Biosystems) and reaction was allowed to proceed under the following condition: 94° C. for 2 min; (94° C. for 15 sec, then 55° C. for 30 sec, then 72° C. for 1 min)×25 cycles; 72° C. for 7 min; 4° C. for an indefinite period.

4AaCter(696-851) thus prepared was inserted into a plasmid obtained by digestion of pΔGST-CRP with BamHI to create pΔGST-4AaCter-CRP. pΔGST-4AaCter-CRP will express a fusion protein of 4AaCter and CRP (4AaCter-CRP).

<Expression of Fusion Protein>

Figure 25:
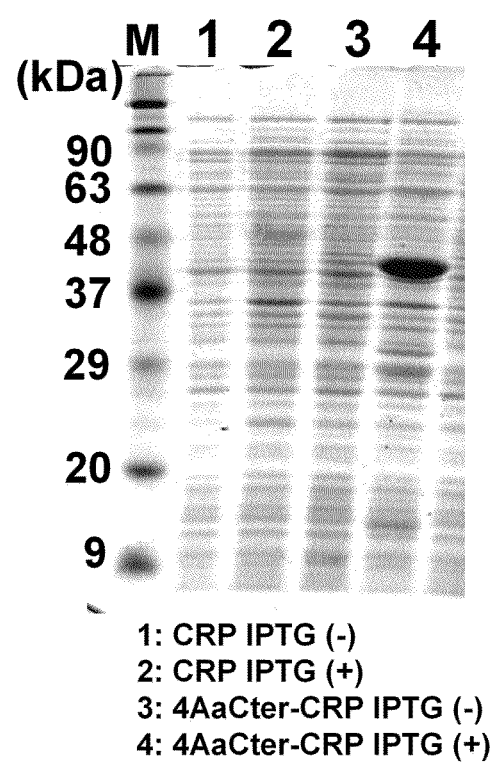
FIG. 25 is a photograph showing the result of SDS-PAGE for confirmation of expression of CRP and 4AaCter-CRP.

Thus created pΔGST-4AaCter-CRP was introduced into E. coli BL21 strain cells. The procedures of introduction of this expression vector and induction of expression of E. coli cells were the same as those described above with regard to the introduction of pGST-4AaCter into E. coli cells and induction of its expression. Expression of 4AaCter-CRP was confirmed as follows: the cells were collected and suspended in 10 mL PBS, and after subjected to sonication (ON for 20 sec, OFF for 10 sec), the buffer containing the fractured cells was run in SDS-PAGE together with human CRP (which had been obtained by inserting human CRP gene into a BamHI and XhoI-digested plasmid pΔGST-4T-3, and introducing the plasmid thus obtained into E. coli cells and inducing its expression). As a result, while a band of interest was detected at about 48 kDa with CRP fused to 4AaCter in comparison with the run of a sample taken before induction of expression, no band of interest was observed at about 29 kDa with CRP which had been expressed without fusion with 4AaCter (FIG. 25).

Figure 26:
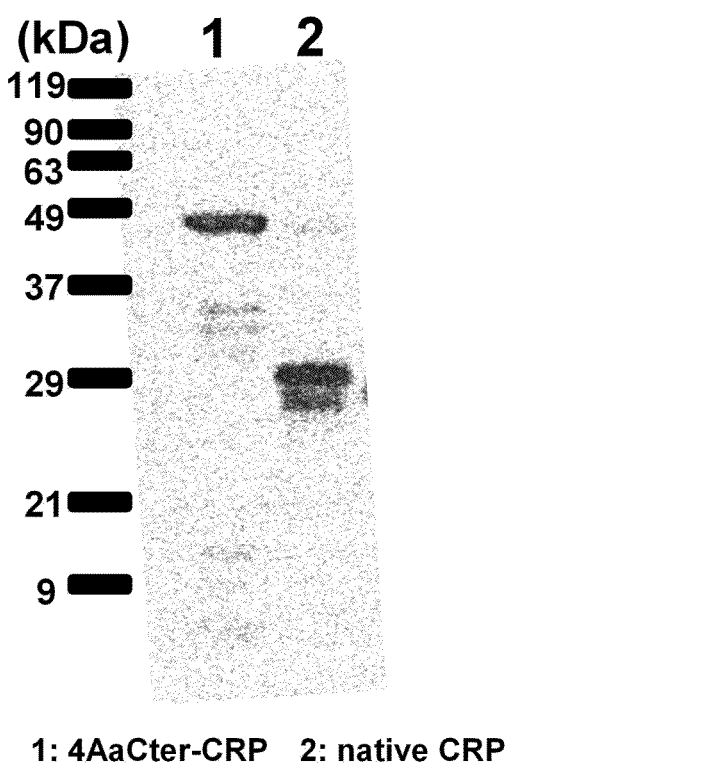
FIG. 26 is a photograph showing the result of Western blotting of 4AaCter-CRP and human-derived CRP.

Western blotting of this and human native CRP biological sample using anti-4AaCter-CRP goat antiserum confirmed that this antiserum was reactive to both 4AaCter-CRP and native CRP (FIG. 26). The above results thus indicate that expression of CRP is now available by fusing 4AaCter with CRP, and that an antibody reactive to native CRP can be obtained using 4AaCter-CRP as the immunogen.

<Method for Preparation of Anti-4AaCter-CRP Goat Antiserum>

A goat which had been kept for at least one week for habituation was immunized with 2 mg of 4AaCter-CRP mixed with Freund's complete adjuvant, 5 times at 2-week intervals, and blood was taken from the jugular vein. The blood thus obtained was kept at 37° C. for one hour and let stand at 4° C. for a day and a night. The supernatant obtained was centrifuged at 3000 rpm for 5 minutes, and the supernatant thus obtained was used as 4AaCter-CRP antiserum.

Example 8

Preparation of Anti-4AaCter Antiserum

Immunoassays using an antibody are often performed following expression processes of recombinant proteins, as a method to confirm whether the proteins expressed are the intended ones. However, it is time consuming and costly to provide antigens which are specific to the proteins of interest. For this reason, a method is employed in which a protein of interest is expressed in the form a fusion protein with some other known protein and the expression of the protein of interest is confirmed using an antibody specific to the known protein. Thus, an examination was carried out to ascertain whether protein expression can be confirmed using an anti-4AaCter antibody in the case of a 4AaCter fusion protein.

pΔGST-4AaCter was created by inserting in-frame a gene fragment coding for 4AaCter into the BamHI site of pΔGST, which had been made by removing the GST gene from pGEX4T-3. This vector, pΔGST-4AaCter, expresses 4AaCter in E. coli cells.

4AaCter was let express in E. coli BL21 cells, and after the cells were fractured, the precipitate that was fractionated by centrifugation was solubilized in an alkaline buffer with a pH of 12. Rabbits were immunized in a conventional manner with the solubilized 4AaCter, and anti-4AaCter antiserum was obtained. Namely, rabbits (New Zealand White) which had been kept for one week for habituation were immunized with 0.5 mg of 4AaCter mixed with Freund's complete adjuvant 5 times at two-week intervals, and blood was taken from the jugular vein. The blood thus obtained was kept at 37° C. for one hour and let stand at 4° C. for a day and a night. The supernatant thus obtained was centrifuged at 3000 rpm for 5 minutes, and the supernatant thus obtained was used as 4AaCter antiserum.

Figure 27:
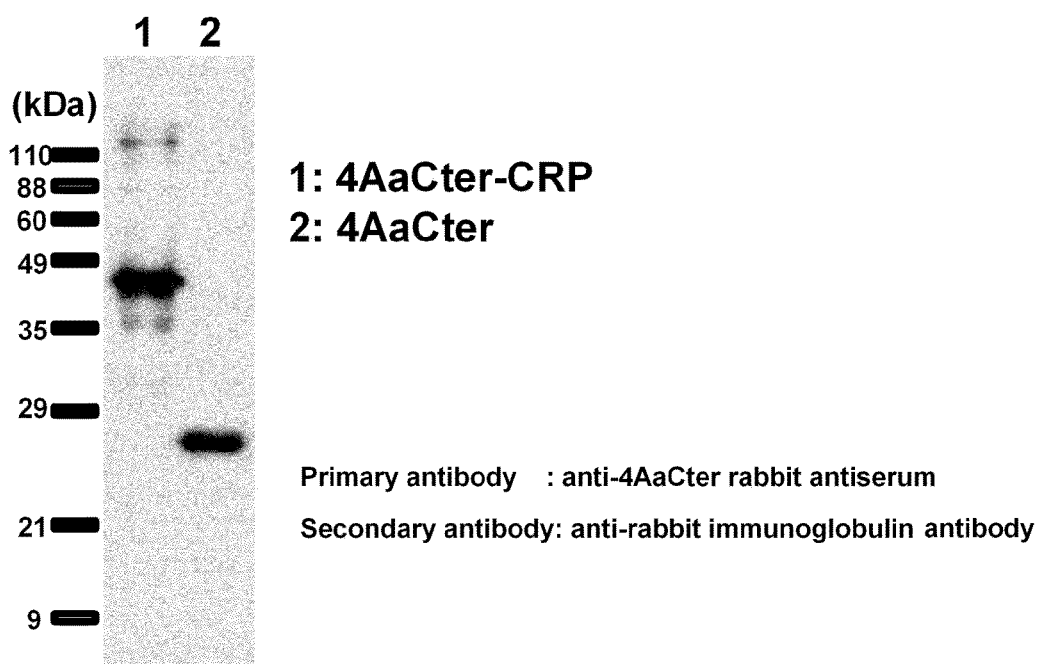
FIG. 27 is a photograph showing the result of Western blotting of 4AaCter and 4AaCter-CRP.

Western blotting of 4AaCter and 4AaCter-CRP using the 4AaCter antiserum obtained above confirmed that this antiserum was reactive to both 4AaCter and 4AaCter-CRP (FIG. 27). This result indicates that it is possible to generate an antiserum reactive to 4AaCter by using 4AaCter as the immunogen, and that the 4AaCter antiserum is also reactive to the 4AaCter fusion protein.

INDUSTRIAL APPLICABILITY

The present invention enables to produce a heterologous protein as a fusion protein with a Cter, in bacterial cells, such as E. coli cells, in a great amount in the form of insoluble crystals retaining the protein's activity, which crystals can be solubilized and recovered as an active protein. Thus, the present invention is utilized for production of heterologous proteins using bacteria, such as E. coli, as a host. Further, an antiserum which is created using a fusion protein of the present invention can be utilized in analysis of the original protein, the protein before fusion with a Cter, e.g., as an testing reagent.

[Sequence Listing]
GP124-PCT.ST25

We claim:

1. A method for production of a protein (A) in the form of a fusion protein, comprising the steps of
   (a) preparing a DNA which codes for a fusion protein comprising the peptide chain forming the protein (A) and a second peptide chain (B), wherein
   the N-terminus of protein (A) is fused to the C-terminus of peptide (B) either directly or via a spacer; or
   the C-terminus of protein (A) is fused to the N-terminus of peptide (B) either directly or via a spacer, wherein the peptide chain (B) consists of a part of the amino acid sequence that starts with Ile696 and ends with Glu1180 of SEQ ID NO: 89, and
   the part comprises the sequence set forth in SEQ ID NO: 6,
   (b) introducing the DNA into a host bacterium, and
   (c) expressing the fusion protein in the host bacterium.

2. The method of claim 1, wherein in step (a), a DNA which codes for an amino acid sequence comprising a spacer that can be specifically cleaved by a proteolytic enzyme is interposed between the DNA coding for the protein (A) and the DNA coding for the peptide chain (B).

3. The method of claim 1 comprising a further step of fracturing the host bacterium to collect the fusion protein.

4. The method of claim 3 comprising a further step of purifying the collected fusion protein through solubilization of the fusion protein in an alkaline aqueous solution.

5. A method for production of a protein (A) comprising the steps of
  (a) preparing a DNA which codes for a fusion protein comprising the peptide chain forming the protein (A) and a second peptide chain (B), wherein
  the N-terminus of protein (A) is fused to the C-terminus of peptide (B) either directly or via a spacer; or
  the C-terminus of protein (A) is fused to the N-terminus of peptide (B) either directly or via a spacer, wherein the peptide chain (B) consists of a part of the amino acid sequence that starts with Ile696 and ends with Glu1180 of SEQ ID NO: 89, and
  the part includes the sequence set forth in SEQ ID NO: 6,
  (b) introducing the DNA into a host bacterium,
  (c) expressing the fusion protein in the host bacterium,
  (d) fracturing the host bacterium to collect the fusion protein,
  (e) purifying the collected fusion protein through solubilization of the fusion protein in an alkaline aqueous solution, and
  (f) removing the peptide chain (B) from the fusion protein.

6. The method of claim 5, wherein the peptide chain (B) is removed by treating the fusion protein with a proteolytic enzyme which acts on a specific cleavage site located in a spacer situated between the peptide chain forming the protein (A) and peptide chain (B).

7. A fusion protein produced by the method of claim 3.

8. A fusion protein produced by the method of according to claim 1.

9. A fusion protein produced by the method of according to claim 5.

* * * * *

UNITED STATES PATENT AND TRADEMARK OFFICE
CERTIFICATE OF CORRECTION

PATENT NO. : 8,865,428 B2
APPLICATION NO. : 13/056944
DATED : October 21, 2014
INVENTOR(S) : Sakai et al.

Page 1 of 1

It is certified that error appears in the above-identified patent and that said Letters Patent is hereby corrected as shown below:

In the Claims

Column 338, line 14 reads "8. A fusion protein produced by the method of according to"
should read -- 8. A fusion protein produced by the method of --

Column 338, line 16 reads "9. A fusion protein produced by the method of according to"
should read -- 9. A fusion protein produced by the method of --

Signed and Sealed this
Seventeenth Day of March, 2015

Michelle K. Lee
*Director of the United States Patent and Trademark Office*